(12) United States Patent
Snow

(10) Patent No.: US 12,220,251 B2
(45) Date of Patent: *Feb. 11, 2025

(54) SENSORY STIMULATION OR MONITORING APPARATUS FOR THE BACK OF NECK

(71) Applicant: Copa Animal Health, LLC, Medina, MN (US)

(72) Inventor: Buddy L. Snow, Medina, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 16/915,275

(22) Filed: Jun. 29, 2020

(65) Prior Publication Data

US 2021/0338969 A1   Nov. 4, 2021

Related U.S. Application Data

(63) Continuation-in-part of application No. PCT/US2015/021286, filed on Mar. 18, 2015.

(Continued)

(51) Int. Cl.
*A61H 23/00* (2006.01)
*A61B 5/00* (2006.01)
(Continued)

(52) U.S. Cl.
CPC ........... *A61B 5/4836* (2013.01); *A61H 23/00* (2013.01); *A61H 23/008* (2013.01); *A61H 23/02* (2013.01);
(Continued)

(58) Field of Classification Search
CPC .. A61M 2021/0022; A61M 2021/0027; A61M 2021/005; A61M 21/02;
(Continued)

(56) References Cited

U.S. PATENT DOCUMENTS 2,249,572 A   7/1941   Lieber
5,457,751 A   10/1995  Such
(Continued)

FOREIGN PATENT DOCUMENTS

EP    1931170     11/2008
JP    2007235922   9/2007
(Continued)

OTHER PUBLICATIONS

International Search Report and Written Opinion for International application No. PCT/US2015/021286 mailed Aug. 17, 2015 (16 pages).

*Primary Examiner* — Christine H Matthews
(74) *Attorney, Agent, or Firm* — Jose W. Jimenez; JIMENEZ LAW FIRM

(57) ABSTRACT

Described herein are wearable sensory stimulation and monitoring devices that can be worn around the back of the neck along and in contact with the spine. Apparatuses described herein stimulate one or more senses including auditory, tactile or olfactory. Apparatuses are also described that allow for sensing and monitoring of physiologic parameters such as heart rate, blood pressure and movement. The device also has features that allow for easy attachment or integration to articles worn on the head such as augmented reality and virtual reality accessories to provide visual stimulation and entertainment.

12 Claims, 53 Drawing Sheets

Related U.S. Application Data

(60) Provisional application No. 61/955,384, filed on Mar. 19, 2014.

(51) Int. Cl.
*A61H 23/02* (2006.01)
*A61M 21/00* (2006.01)
*A61M 21/02* (2006.01)
*A61N 1/36* (2006.01)
*A63B 71/06* (2006.01)
*G06F 3/01* (2006.01)
*H04R 1/02* (2006.01)
*H04R 5/033* (2006.01)

(52) U.S. Cl.
CPC ..... *A61H 23/0218* (2013.01); *A61H 23/0236* (2013.01); *A61M 21/02* (2013.01); *A61H 2201/0157* (2013.01); *A61H 2201/16* (2013.01); *A61H 2201/1602* (2013.01); *A61H 2201/1604* (2013.01); *A61H 2201/1607* (2013.01); *A61H 2201/1609* (2013.01); *A61H 2201/1611* (2013.01); *A61H 2201/165* (2013.01); *A61H 2205/02* (2013.01); *A61H 2205/04* (2013.01); *A61M 2021/0022* (2013.01); *A61M 2021/0027* (2013.01); *A61M 2021/005* (2013.01); *A61M 2209/088* (2013.01); *A61M 2210/1003* (2013.01); *A61N 1/36014* (2013.01); *A63B 2071/0625* (2013.01); *G06F 3/011* (2013.01); *H04R 1/025* (2013.01); *H04R 5/0335* (2013.01); *H04R 2460/13* (2013.01)

(58) Field of Classification Search
CPC .... A61M 2210/1003; A61M 2209/088; A61H 2205/02; A61H 2205/04
See application file for complete search history.

(56) References Cited

U.S. PATENT DOCUMENTS

| | | | |
|---|---|---|---|
| 6,233,345 | B1 | 5/2001 | Urwyler |
| 6,483,925 | B1 | 11/2002 | Shen et al. |
| 6,603,863 | B1 | 8/2003 | Nagayoshi |
| 6,792,122 | B1 | 9/2004 | Okada et al. |
| 6,944,309 | B2 | 9/2005 | Terai et al. |
| 7,848,512 | B2 | 12/2010 | Eldracher |
| 8,139,803 | B2 | 3/2012 | Afshar |
| 8,761,428 | B2 | 6/2014 | Amae |
| 8,767,996 | B1 | 7/2014 | Lin et al. |
| 9,055,795 | B2 | 6/2015 | Larkin |
| 10,695,263 | B2 * | 6/2020 | Snow ............... A61M 21/02 |
| 2007/0038164 | A1 * | 2/2007 | Afshar ............... H04R 1/02 601/47 |
| 2009/0154755 | A1 | 6/2009 | Yamagishi et al. |
| 2009/0185699 | A1 | 7/2009 | Kim |
| 2009/0318198 | A1 | 12/2009 | Carroll |
| 2011/0160811 | A1 * | 6/2011 | Walker ............. A61N 1/0464 607/2 |
| 2011/0250958 | A1 | 10/2011 | Aarts et al. |
| 2012/0035513 | A1 | 2/2012 | Afshar |
| 2012/0253236 | A1 | 10/2012 | Snow |
| 2013/0017520 | A1 * | 1/2013 | Yoo ................. H04R 25/606 434/247 |
| 2013/0115579 | A1 | 5/2013 | Taghavi |
| 2013/0343591 | A1 * | 12/2013 | Brunner ............ H04R 1/1091 381/371 |

FOREIGN PATENT DOCUMENTS

| | | |
|---|---|---|
| WO | 2009076250 | 6/2009 |
| WO | 2013122870 | 8/2013 |
| WO | 2017009017 | 1/2017 |

\* cited by examiner

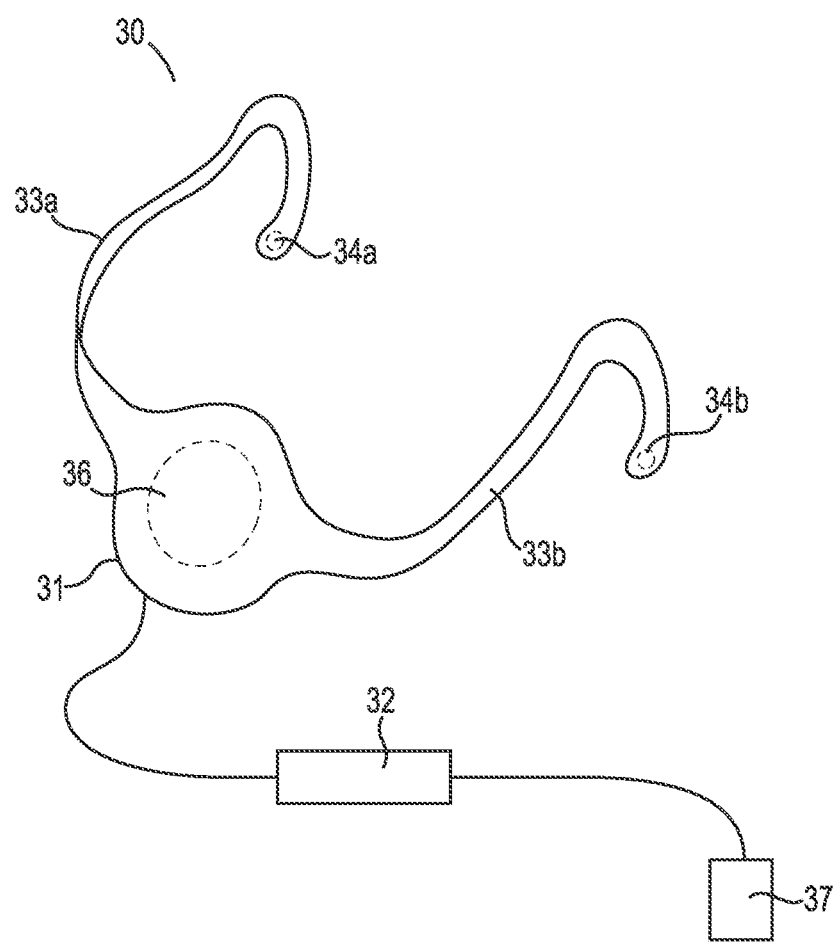

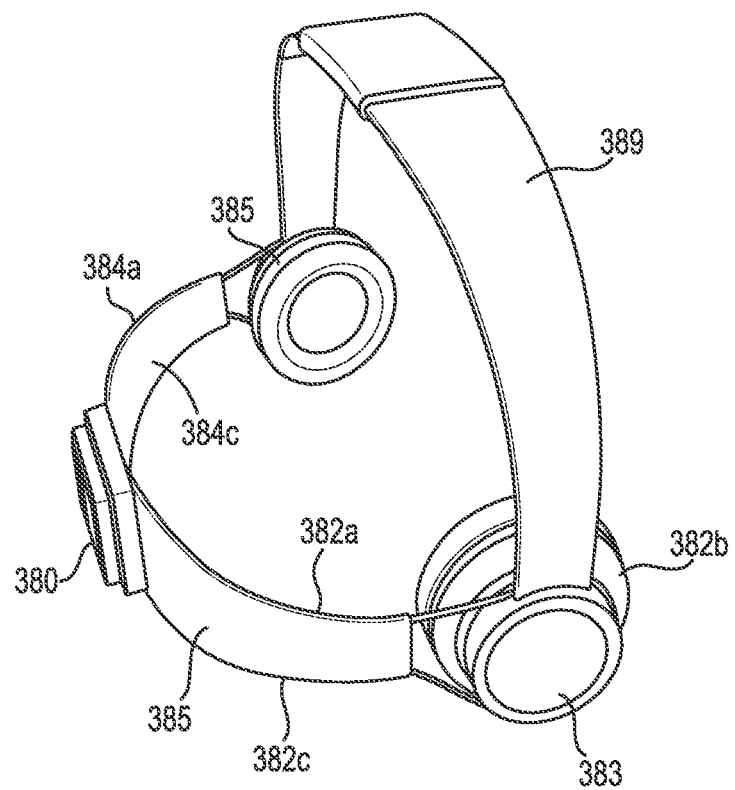

SENSORY STIMULATION OR MONITORING APPARATUS FOR THE BACK OF NECK

CLAIM OF PRIORITY

This application is a continuation-in-part of International Application No. PCT/US2015/021286, filed on Mar. 18, 2015, which claims priority to U.S. Provisional Patent Application No. 61/955,384, filed Mar. 19, 2014, this application is also a continuation-in-part of US 2017/0135896 filed on Sep. 19, 2016 and having Ser. No. 15/269,655, the entire contents of which are all incorporated herein by reference in their entireties.

FIELD OF THE INVENTION

The present invention relates generally to wearable sensory stimulation apparatuses worn on the head and neck.

BACKGROUND OF THE INVENTION

The human brain is multi-sensory and receives stimulation from the outside world via sound, touch, smell, vision and taste. Commercially available options for delivering and receiving stimulation include headphones or ear buds that deliver audio to the ear, as well as monitoring and sensing apparatuses worn on various parts of the body. Known apparatuses have limitations in their design, function and performance.

SUMMARY OF THE INVENTION

The various embodiments of the invention relate to apparatuses that improve upon existing sensory stimulation devices such as headphones, ear buds and other wearable headset devices by adding a transduction component to the device, such as vibration speakers, haptic exciters, electrical stimulation, olfactory release, or similar transduction members. The various devices taught herein also include monitoring sensors located on the back of the neck and the spine. These apparatuses can be used to improve audio output performance at lower frequencies, and therefore lower volumes. In an example embodiment, the apparatus is used to train, teach, improve, and recover from athletic performance or activity. In other embodiments, the apparatus is used for entertainment or communication purposes. Alternative embodiments are also used to monitor and diagnose physiological processes, and even deliver forms of sensory stimulation for health, healing or improve coordination purposes.

The teachings herein improve the performance and experience of existing headphones, ear buds, headsets and other wearable audio delivery devices by adding transduction components such as vibration speakers or similar haptic delivery methods to the system, and placing these components on the back of the neck and/or upper spine of the user. The vibration transduction components allow for better delivery of lower frequencies, especially when in direct contact with the user. This improvement allows lower frequencies to be optimally played, heard and felt through the peripheral sensory nerve pathway, in conjunction with the existing auditory channel, thus more closely resembling larger room speaker output experiences. The wearable audio delivery devices may also be waterproof, adjustable, remote controlled, lightweight, foldable, noise cancellation capable and the like.

By activating neurologic pathways along the spine, especially cranial nerves, using sound, vibration and music therapy, the user can also receive health benefits. This application provides the embodiments that can be used to monitor, assess and deliver various forms of vibration therapy to individuals, as well as methods to help coach, train, and recover for improved athletic performance. Additionally, embodiments describe apparatuses that can be used to treat conditions such as tinnitus, Alzheimer's, Parkinson's, autism, or similar brain-related conditions.

It would be preferable to place a plurality of sensing components on the back of the neck to assess the health condition of the individual. Brain stem activity, heart rate, oxygenation, pulse, movement and other processes may be monitored effectively on the back of the neck. Also, when used in conjunction with the above transduction components, various forms of vibration therapy can be administered, either on the neck, wrist, back, or other points on the body to achieve neurologic stimulation.

It is taught herein to have a training device for athletic performance such as for golf, baseball, tennis, or other sports. The device can be worn around the neck and over the ears to deliver specific instruction before, during and after the activity. When accompanied by a vibration speaker or similar transducer, the device can stimulate the spine for improved neurologic outcomes. In one example embodiment, the device includes instruction methods, such as swing tempo for golfers, which are loaded on the device and delivered to help train, teach, heal and recover during and after athletic performance or activity.

Embodiments of the invention set forth a wearable audio delivery apparatus configured for use with a speaker set that is placed in or about the ears, with the apparatus including (a) a housing having at least one vibration speaker or vibration transduction component, the housing configured to be positioned on the back of the neck and on the spine, and (b) right and left attachment members with a proximal portion directly or indirectly connected to the housing, and the attachment members each having a distal portion configured for removable attachment to the ears or to speaker enclosures of a speaker set that is placed about the ears.

Embodiments of the invention also set forth a wearable audio delivery apparatus that include (a) a speaker set that is placed in or about the ears, (b) a housing having at least one vibration speaker or vibration transduction component, the housing configured to be positioned on the back of the neck and on the spine, and (c) right and left attachment members each comprising a proximal portion directly or indirectly connected to the housing, and a distal portion attached to a portion of a speaker set that is placed in or about the ears, wherein the attachment members are flexible, stretchable, or both flexible and stretchable.

Embodiments of the invention also set forth a wearable monitoring apparatus that includes (a) a housing having a sensing feature, the housing configured to be positioned on the back of the neck and on the spine, and (b) right and left attachment members directly or indirectly connected to the housing, wherein the attachment members allow the housing to be stably immobilized on the head of a user or to be attached to a headpiece. In a related example embodiment and platform, there is provided mobile content delivery systems that allow people to engage with various forms of recorded, digital content while being mobile and wanting to experience the content via as many sensory stimuli as possible. This example embodiment delivers music, gaming, video, therapeutic, or other forms of digital content to entertain, improve or enhance a person's life. Specifically, these related embodiments encompass various forms of wearable headsets that deliver various forms of multi-sensory stimulation content to users. These mobile headsets deliver content such as audio, video, virtual reality (VR), augmented reality (AR) and mixed reality (MR), allowing the user to hear, feel, see and smell the content. Content can be streamed, uploaded or connected directly to the headsets or components via methods such as smartphones, tablets, hard drives, cables and other connection methods. The drawback with existing video headsets is they only deliver one or two sensory stimulation methods, primarily visual and sometimes audio. These existing headsets limit the experience and mobility options consumers have with the digital content. One of the additional characteristics of this embodiment is that it allows the audio signal to be split, filtered, amplified and delivered to multiple speakers and similar audio outputs to provide the user with a more realistic, surround sound experience.

In one of various example embodiments, there is provided headphones with a modular attachment system, along with methods how to attach various components to the headphones. The modular headphone system incorporates methods of component attachment using a variety of fixtures that are part of or in addition to the headphone or the headphone ear cup molds. These fixtures, or methods of attachment, allow for components to be held securely in place on or around the head including, but not limited to, on the neck, over the eyes, on the face, from the ear cups, around the forehead, extending from or on top of the head. The fixtures can be fixed into the headphones or can be interchanged to allow for other fixtures. One representative embodiment use would be to allow a user to experience digital content in a new way. A user could play a video on their smartphone or other device, put on our headphones to listen to the audio, attach a subwoofer to the headphone fixture so it rests on the back of the neck to add tactile sensation, and then insert their smartphone into a virtual reality attachment that plugs into the headphone attachment fixture on the front of the ear cup and plays video in front of the user's eyes.

Another representative embodiment use would be for an air traveler who wants to connect a thermal node around their neck to help relax and sooth, and insert an eye covering shade into the headphones to block out lights and noises. Still another representative embodiment would be for a user to attach a heart rate or blood pressure monitoring device to the headphone to monitor conditions that could then be transmitted to external users such as physicians. Another representative embodiment would be to attach or insert a mechanism to the headphone or headphone ear cup that projects images, videos, virtual or augmented reality images, or the like in front of the user for entertainment, wellness or for training. Still another representative embodiment would be a user who wants to personalize their headphones by adding a decorative attachment to the ear cups. The attached or connected components can be new forms of stimulation to the user, as well as various types of other accessories. These components can be connected to headphones using flexible, rigid or semi-rigid attachment members that secure to the headphones and ear cups through various types of fixtures or accessories. Additionally, these attached components can also be directly or wirelessly connected to external devices such as power supplies, content delivery systems, entertainment systems, training apparatuses, fitness machines or diagnostic equipment. One of the main benefits of this invention is to create new methods so various forms of recorded digital content, such as movies, fitness or wellness training, sports events, travel, music concerts, amusement parks, or the like, can be delivered through our modular headphones so users can have multi-sensory stimulation experiences without needing to travel to places for entertainment or healthcare needs.

Articles and types of manufacture, materials, features and advantages of the various embodiments of the invention will become apparent to someone in the art having ordinary skill. It is intended that all such articles included within this description be within the scope of the present invention, and thus protected by the associated claims.

BRIEF DESCRIPTION OF THE DRAWINGS

Other important advantages of the invention will be apparent from the following detailed description of the invention taken in connection with the accompanying drawings.

FIG. 3 illustrates a wearable audio and vibrational delivery or monitoring device that includes vibration speakers or similar transduction members into headphones that go around the back of the head to the ears;

FIGS. 17A-17D are front, side and perspective views of embodiments of an attachable audio delivery device with housing for placement on the back of the neck, the device attached to speaker enclosures of a headphone set.

FIG. 53 illustrates same with various receptacles for various attachments to be disposed on a user's neck, ear and face while FIG. 54 illustrates same with attachable components for wired and wireless connection to other external devices.

DETAILED DESCRIPTION OF THE INVENTION

Figure 1A:
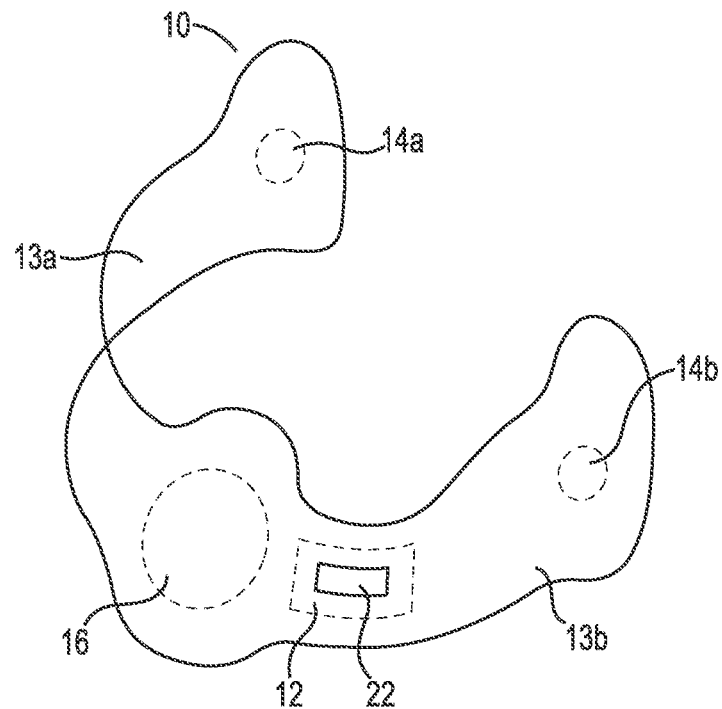
FIGS. 1A-1B illustrate perspective views and a side view of a wearable audio and vibrational delivery or monitoring device that incorporates vibration speakers, other transduction components, and physiological sensors that is placed on the back of the neck.

The detailed description that follows below is intended to provide illustration to the principles of the invention. This description is not provided to limit the possibilities of the invention described herein, but rather to explain and teach the principles in such a way that a person of ordinary skill in the art could apply them to practice not only to the embodiments described herein, but also to other embodiments that could come into mind when applying the principles. The intention is to not limit the disclosures and claims listed herein, but to also include all similar embodiments.

The various embodiments described herein detail improvements to currently available devices, such as headphones, ear buds, headsets, headbands, glasses, and the like, that are worn by humans to deliver sound. By including additional speakers or other haptic transducers to these devices, and placing them around the back of the neck along and in contact with the spine, allows lower frequencies to be played more effectively, and can be heard and felt at the same time, thus improving audio output performance. Musicians, disc jockeys and audiophiles will be able to enhance the audio output. In a related embodiment, videos gamers will also enjoy an enhanced experience with the improved audio device taught herein. Features such as waterproof, adjustable, remote control, volume control, lightweight, foldable, noise cancellation and the like may also be included.

Additionally, since the neck is an ideal location to assess the health of a human, it is also envisioned that physiological health monitoring sensors may be incorporated into the systems, thus allowing users to track brain activity, movement, heart rate, blood pressure, glucose output and similar bodily functions. In an example embodiment, the device is capable of delivering this information to a user's computer or smartphone. These assessments could be used in conjunction with the delivery of therapy through transduction members also placed within the wearable devices on the back of the neck and used to stimulate the nervous system throughout the body.

Also, it is taught herein that the device is capable of incorporating teaching, training, and recovery regimens into the delivery device and worn on the back of the neck. This placement keeps the unit out of the way, allows for focus since it covers the ears, and delivers therapy along the spine before, during, and after performance needs. The device may be used for athletic activities, such as golf, baseball, tennis, bicycling, and other sports. When combined with the various forms of vibration delivery, improvements such as balance, stability, hand/eye coordination, muscle firing, and other neurologic processes are expected.

Additionally, placing optional sensing mechanisms within one or more embodiments allows the accurate assessment of physiological processes such as heart rate, blood flow, blood pressure, brain stem activity, and user activity. This monitoring functionality is used to not only assess health and deliver that output to the user, but also can be connected to wearable forms of delivering therapy through the transduction components. Example benefits of this embodiment allow for users to wear the headphones to assess conditions associated with aging, such as balance or stability issues, anxiety, fatigue, lack of mobility or pain, and deliver a sensory therapy to help correct or address these symptoms.

Also, throughout the disclosure various embodiments are described that include a vibratory or audio transducer component(s) placed inside of a housing, which is configured for placement on back of the neck. It is envisioned that the vibratory or audio transducer component in any of the disclosed embodiments could be supplemented with or replaced by other non-audio or non-vibrational stimulation components to provide a stimulatory effect to a user to achieve a desired outcome.

Exemplary non-audio or non-vibrational stimulation components include but are not limited to electrical stimulation, transcutaneous electrical nerve stimulation (TENS), extracorporeal shock wave therapy (ESWT), olfactory or pheromone stimulation.

Figure 6:
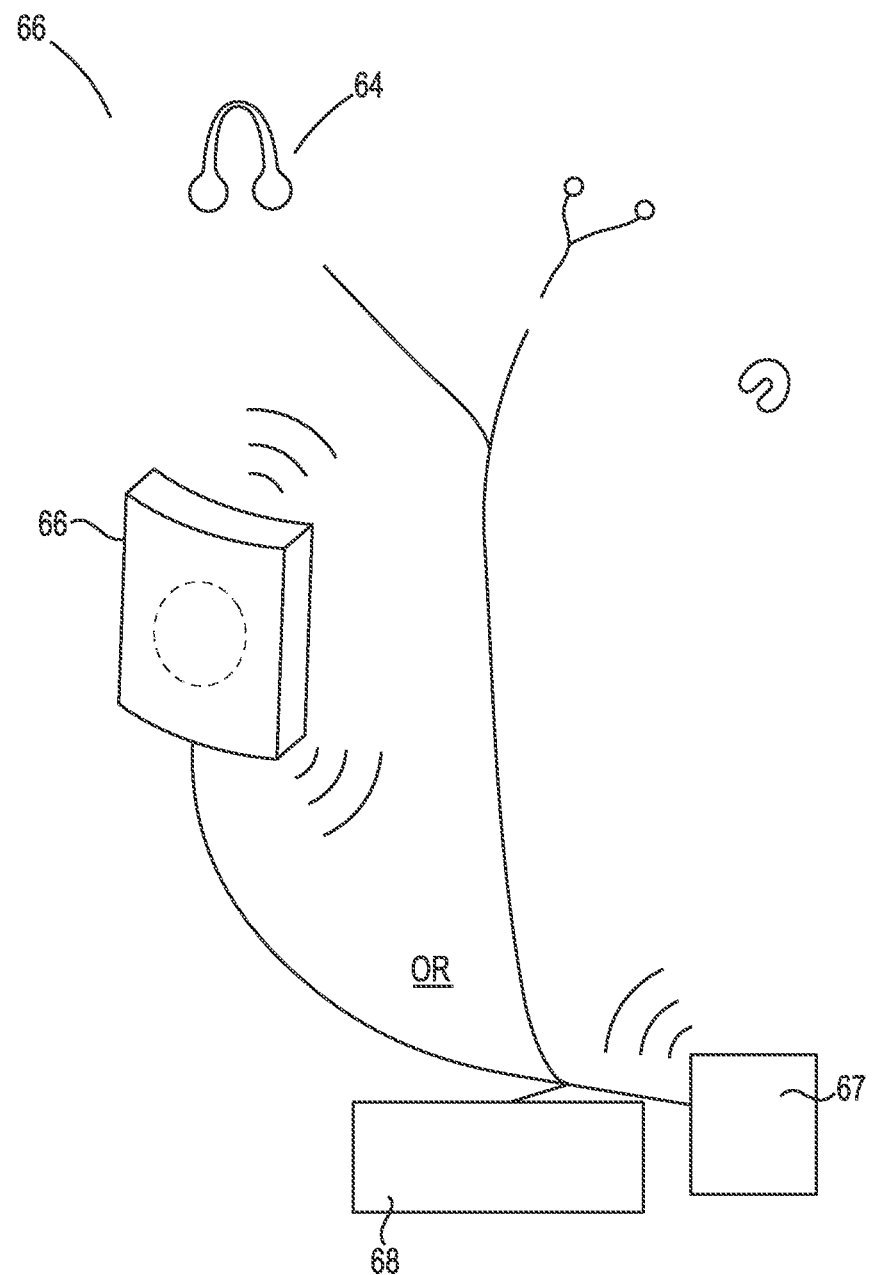
FIG. 6 illustrates a wearable audio and vibrational delivery or monitoring system that includes vibration speakers or transduction members on the back of the neck and is attached with or without wires to headphones to an audio output device, headphones and earbuds.

FIG. 6 illustrates a system 60 with components for wearable audio delivery and/or monitoring that can include a vibration speaker 66 or similar transduction members, and/or monitoring sensors, configured for placement on the back of the neck. The vibration speaker 66 can be attached either with or without wires (wirelessly) to headphones 64 to an audio output device 67, headphones and ear buds. The wearable audio delivery and monitoring device 60 can include a splitter jack 68 that allows the device to be connected to both the ear buds 30 and vibrational speakers 20.

In some embodiments the vibration transduction component that provides lower frequency output is an "add-on" component, meaning that is provided apart, i.e., as a separate component, from a headphone or earbud speaker set that the user may already possess. In this embodiment, the audio delivery apparatus can be referred to as configured for the "removable attachment" to the ears, or to speaker enclosures of a speaker set that is placed about the ears. In order to explain aspects of the invention, features of commercially available over the ear-type headphones and earbud-type headphones, and which can be used with an "attachable" audio delivery apparatus including vibration speaker or vibration transduction component, are described.

Commercially available "over the ear" headphones (herein referred to as "headphones") generally include a pair of small loudspeakers within an enclosure or housing that is held in place over a user's ears. Typically, the speaker enclosures are attached to a band that goes over the user's head and that provides a slight inward force to press the enclosures up against the user's ears, which aid in providing stability during use. Speaker enclosures generally include padding, such as a foam material covering all or a portion (such as about the periphery) of the inner (user) side of the enclosure to improve the comfort of the headphones. Typically, the band over the top of the user's head is adjustable to provide desired placement of the speaker enclosures. Commercially available speaker enclosures of headphones are of various shapes and sizes. Common shapes for speaker enclosures include oval, circular, and oblong shapes. The size of such enclosures can be somewhat small, such as less than the size of the outer ear of a user or can be rather large and have a periphery that is larger than the outer ear. For example, the periphery of a speaker enclosure of a headphone may be in the range of about 10 cm to about 30 cm, or about 15 cm to about 25 cm.

Other commercially available speaker sets for use on the head include earphones (referred to herein as "earbuds") and in-ear headphones (also referred to as "in-ear monitors," (IEMs) or "canal phones"). Earbuds are very small speaker enclosures that are configured to fit within the outer ear, and which face but are not inserted into the ear canal. Earbuds typically include a soft firm material, such as a foam pad, on the ear-canal facing surface to provide comfort. In-ear headphones have a speaker enclosure that is configured to extend into the ear canal. In-ear headphones can be generic, or custom fitted, and made from materials such as silicone rubber, elastomers, and foam. Speakers found within headphones, earbuds, and in-ear headphones are electroacoustic transducers which convert an electrical signal to a corresponding audio wave which provides a sound in the user's ear. Typical speakers within headphones, earbuds, and in-ear headphones provide an audio signal generally over a broad frequency range, for example in the range of about 20 Hz (very low bass tones) to about 20,000 Hz (the highest treble), which represent the lower and upper ends, respectively, of what the human ear can detect. However, unlike low frequency speaker systems, the output of commercial headphones, earbuds, and in-ear headphones is desirably equally distributed over the broad frequency range.

In contrast to speakers found within headphones, earbuds, and in-ear headphones the vibration speaker or vibration transduction component of the current disclosure can provide a low frequency output to create vibration on the back of the neck and over the spine. The vibration speaker or vibration transduction component can be used with the attachment embodiments and integrated embodiments of the invention. In some respects, the apparatus can be described by parameters of the low frequency output. For example, most (greater than 50%, greater than 60%, greater than 70%, greater than 80%, greater than 90%, greater than 95%, greater than 99%) of the output of vibration transduction component can be below 250 Hz, below 200 Hz, below 150 Hz, below 125 Hz, or below 100 Hz, such as in the range of about 20 Hz to about 200_Hz, or about 20 Hz to about 100 Hz.

In some embodiments the vibration transduction component can produce infrasonic waves (i.e., acoustic waves having a frequency below 20 Hz, versus "sonic" having a frequency of 20 to about 20,000 Hz). Devices such as tactile transducers and specialized transducers referred to as linear actuators can produce infrasonic waves. The vibration transduction component capable of producing infrasonic waves can include an electromagnetic motor, with a new magnet structure with a vented center pole to allow air to move in and out more efficiently.

An exemplary electromechanical transducer which can be used in association with the audio output apparatus of the current disclosure is described in EP2779696A1, which is incorporated herein by reference. In one aspect, the apparatus has a housing that has electromechanical transducer that transduces an electric signal into mechanical vibration, the transducer including a structural unit with at least the following integrated components: at least one pair of magnets, a yoke conducting a magnetic flux generated by the magnets, and a coil supplied with the electric signal. The transducer also includes an armature having an inner portion passing through an internal space of the structural unit and first and second outer portions protruding on both sides from the inner portion. The armature constitutes a magnetic circuit with the structural unit via two regions through which components of the magnetic flux flow in directions opposite to each other in the inner portion. The transducer also includes a first elastic member connecting between the first outer portion of the armature and the structural unit; and a second elastic member connecting between the second outer portion of the armature and the structural unit.

In some embodiments, the vibration transduction component provides both infrasonic and sonic frequencies. For example, most vibration transduction component can produce predominantly (greater than 50%, greater than 60%, etc.) infrasonic frequencies and sonic frequencies of below 100 Hz. The vibration transduction component can be partially or fully enclosed within a housing. Generally, the housing is configured to be placed on the back of the neck, over the uppermost portion of the spine. In particular the housing can be configured for placement below the occipital ridge of the skull, over the cerebellum, where the spinal cord meets the brain. In position, the housing will be proximal to cervical vertebra 1-3.

Figure 24:
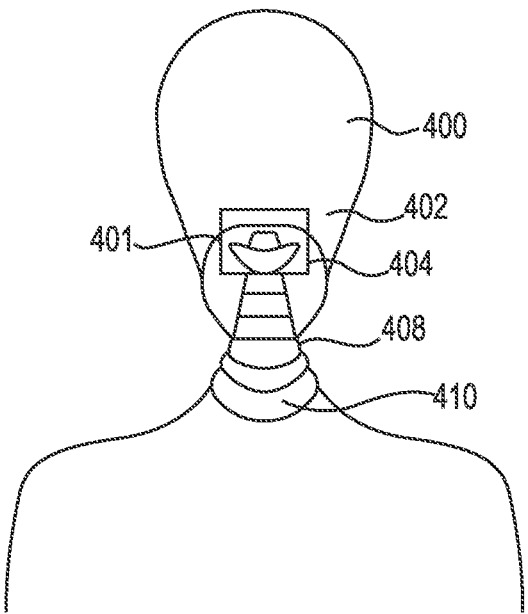
FIG. 24 illustrates anatomical features of the upper body relevant for placement of an audio delivery device or device having a sensing mechanism.
Figure 25:
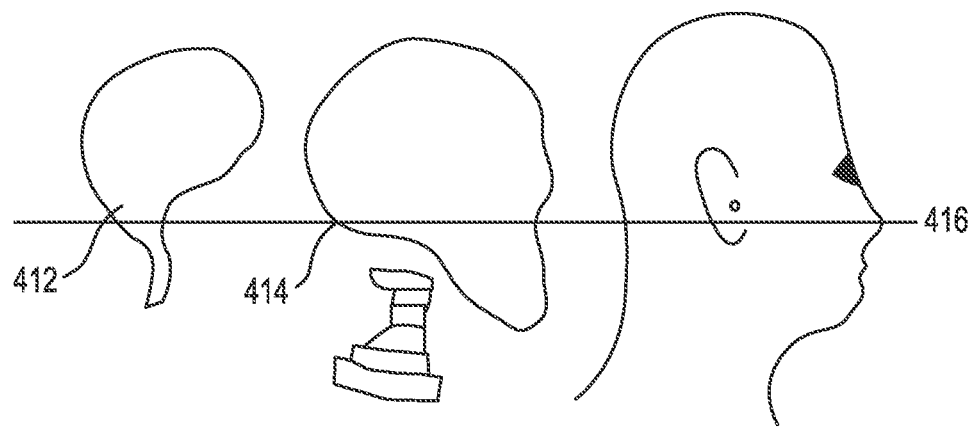
FIG. 25 illustrates anatomical features of the upper body including relevant for placement of an audio delivery device or device having a sensing mechanism.

Reference is made to FIG. 24 illustrating relevant anatomical features of the upper body including skull 400, occipital ridge 402, cervical spine 1-3 404, spine 408, and central nervous system 410. In modes of practice, the target area for placement of the device with the vibration transduction component is represented by circle 401, where the device is placed. FIG. 25 provide illustrations of portions of the head, showing the cerebellum 412, the location where the skull curves down to the spine 414, and line 416 representing the transverse plane for device placement, which allows easy access to audible, tactile, and olfactory receptors.

The advantage of placing vibration speakers or similar delivery transducers on the back of the neck is the direct stimulation into the brain since they are engineered to deliver lower audio and vibration frequencies. This also allows the ear speakers to be optimized to play higher frequencies. An additional benefit of this placement for audio information and sound delivery is for the hearing-impaired population that can feel vibration but may not be able to hear clearly. Other uses include assistance in training, post-operative recovery or rehabilitation. Still another use may be situations such as movie theatres, concerts, or similar settings where surround sound output performance may be delivered individually and personally through worn headsets.

In some cases, the housing can be described in terms of height, width, and thickness ranges. In many configurations, the housing can have a width and height that is greater than its thickness, which can provide the housing with an overall "flat" shape. When in position the height dimension can be defined by upper and lower portions, or edges, which is towards that top of the user's head and towards the user's back, respectively. The width dimension can be defined by left and right portions or edges. The thickness can be defined by a body-facing surface, which is configured to be placed against the skin of a user's neck, and an outer surface, facing away from the neck.

Figure 10:
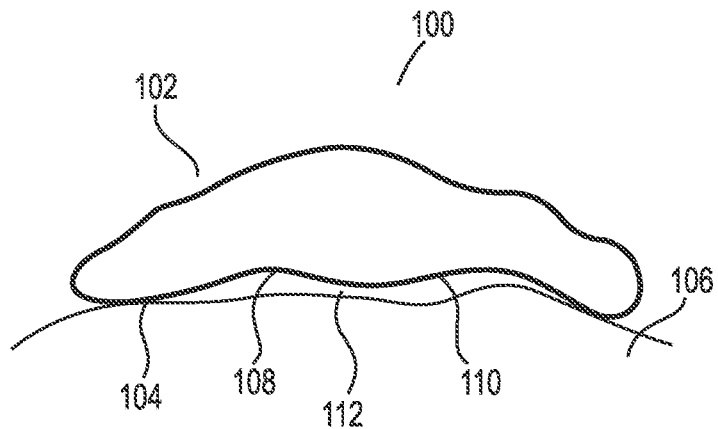
FIG. 10 illustrates a top view of a housing for a vibration speaker or transduction member placed on the back of the neck.

One or more surfaces of the housing can have curvature. For example, the inner surface of the housing can include one or more curved surfaces. The curved surface can include one or more convex and concave shape(s) providing one or more bulges or one or more indentations on the body facing on the surface. FIG. 10 is a top view of an exemplary housing 100 construction, with outward facing surface 102, and body facing surface 104 (an area of the neck 106 is also shown). The indentations 108 and 110 and bulge 112 can match the contour of the neck.

In exemplary embodiments, the housing has a height in the range of about 6.5 cm to about 3.5 cm, or about 5.5 cm to about 4.5 cm; a width in the range of about 10 cm to about 5 cm, or about 8.5 cm to about 6.5_cm; and a thickness in the range of about 2 cm to about 0.5 cm, or about 1.5 cm to about 1 cm. As viewed from the outer face or surface, the housing can have a square, rectangular, oval, or circular shape. An exemplary weight for the housing, including the vibration component therein, is in the range of about 30 to about 55 grams, or about 35 to 45 grams. Exemplary housing materials include plastics and metals and combinations thereof.

Figure 11:
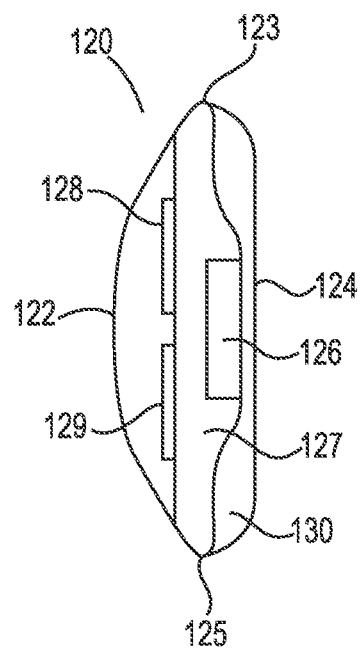
FIG. 11 illustrates a cross-sectional side view of a housing for a vibration speaker or transduction member.

FIG. 11 shows a cross sectional side view of an exemplary housing 120 construction, with outward-facing surface 122, and body-facing surface 124. The outward-facing surface 122 can be curved outwards from the top 123 to the bottom 125 of the housing. A vibration component 126, such as a speaker cone or transduction member, can be secured within the housing. The vibration component can be adjacent to an open area in the housing (e.g., space 127) in which acoustic waves can be generated. The acoustic waves, in turn, are absorbed by the body-facing surface of the housing, which can have a rigid or flexible construction, and cause the vibration of this portion of the housing. The housing can also include one or more areas (e.g., 128, 129) for placement of components useful for operation of the vibration component, such as a battery, a splitter, a short range wireless receiver (e.g., Bluetooth) device, a microprocessor board, and a sensor. Areas for the placement of these features can be located between the outwards-facing surface and the vibration component or open area in the housing.

In embodiments of the disclosure, the attachment member is configured to allow for removable attachment of the apparatus to the ears or to speaker enclosures of a speaker set that is placed about the ears. In embodiments of the disclosure, the attachment member is formed of a cord, a strip of material, a band of material, a mesh, etc. The attachment member can have one or more of the following properties: flexibility, stretchability, elasticity, compliance, durability, and strength. Preferably, the attachment member is flexible, stretchable, or both flexible and stretchable. In this regard, the attachment member can be described as "non-rigid" of made from a "non-hardened material." Use of a flexible and/or stretchable attachment member such as an elastic cord attachment member can provide advantages during use. For example, unlike a hardened plastic material, a flexible and stretchable attachment member can provide better isolation of the low frequency vibrations from the vibration component to the back of the neck. Unlike a hardened material, the flexible and/or stretchable attachment member poorly conducts the vibration from the housing, and therefore provides better response at the point of contact, and prevents low frequency vibrational "bleed through" to the speakers around or in the ears.

The attachment member that is flexible and stretchable can include one or more elastomers. An elastomer is a material that can exhibit a rapid and large reversible strain in response to a stress. Exemplary elastomers include natural rubber (cis-1,4-isoprene polymer), styrene-butadiene rubber, butyl rubber, ethylene propylene diene monomer (EPDM) rubber, polychloroprene, polysulfide, polyurethane elastomers, acrylonitrile butadiene rubber, and silicone rubber. The attachment member that is flexible and stretchable can optionally be described in terms of its "stretchability." For smaller and moderate forces applied to a stretchable material such as an elastomeric cord, a spring constant of a cord can be expressed. A spring constant (k), as measured in N/m, can be calculated by the force applied to the cord over the change in length of the cord.

If the attachment member is in the form of a cord, the cord can have a certain cross-sectional shape, such as a circular shape. However, the cord may also have an oval or polygonal shape (e.g., square, rectangular, etc.) The size of the cord can be expressed as its cross-sectional area, which in some embodiments can be in the range of about 1 mm$^2$ to about 120 mm$^2$, or about 7 mm$^2$ to about 40 mm$^2$. For example, an exemplary cord has a diameter in the range of about 3 mm to about 8 mm. The attachment member, such as an elastomeric cord, can have an inner elastic material and a fabric outer layer coated around an outer periphery of the elastic inner tube. The fabric outer layer can provide improved comfort for a user.

The housing can also include one or more features that facilitate attachment of the right and left attachment members to the housing. For example, the housing can include one or more apertures or channels through which the attachment member can pass. The attachment member, such as a cord, can be movable through the aperture or channel. Generally, the size of the aperture or channel will be at least as large as the largest cross-sectional dimension of the attachment member, such as a cord. Using this arrangement, the attachment member such as a flexible cord, can be moved through the aperture to adjust the length of the attachment member that is to be looped around the ears or around a speaker enclosure of headphones. In this regard, the apparatus can include a tensioning member that allows the attachment member to be secured in relation to the housing, so that a desired length of cord can extend from the housing for attachment to the ears or a speaker enclosure of headphones. The tensioning member can be one that is integrated in or attached to the housing, such as a clip or a clamp. Alternatively, the tensioning member can be independent from the housing, such as one that is movable over the cord. For example, the tensioning member can be a small clamp having an opening through which the cord can move, which can be immobilized on the cord in a clamped state, and which can contact the housing to provide a stop to the movement of the cord.

In some embodiments the housing includes two or more apertures through which the attachment members can be moved through. The housing can include additional apertures, such as a total of 3, 4, 5, 6, etc. according to the design of the apparatus. In some embodiments, the apertures can be located at the periphery of the housing. For example, the housing can have a rectangular or oval shape (e.g., the housing having a width that is greater than its height), where at least one aperture is located on each side of the housing. If each side of the housing has two apertures (for a total of four apertures) the apertures may be referred to as upper and lower apertures.

Figure 12A:
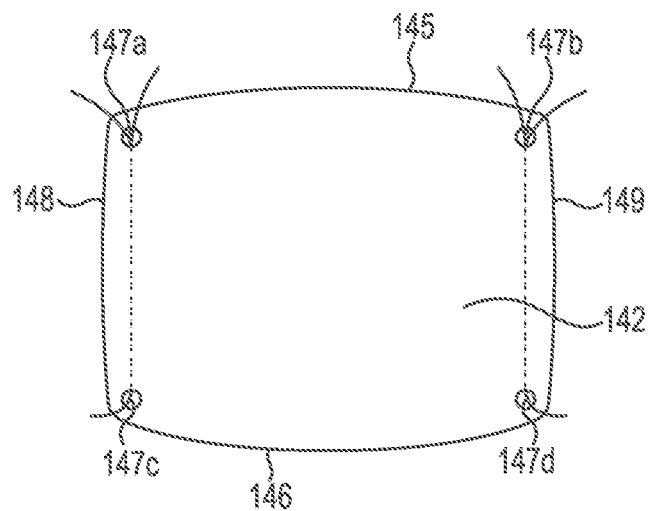
FIGS. 12A and 12B illustrate rear and cross-sectional top views of an embodiment of housing for a vibration speaker or transduction member
Figure 12B:
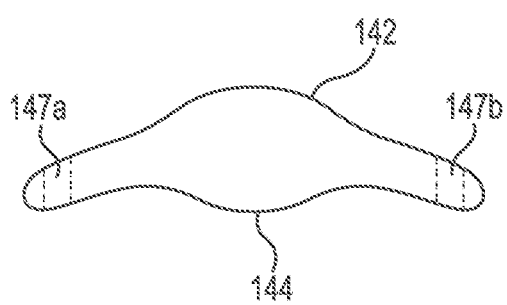

As an example, FIG. 12A shows a view of the outward-facing surface 142, with upper 145, lower 146, left 148, and right 149 sides, defining upper right, upper left, lower right, and lower left corners of the housing. In each corner there is an aperture, for a total of four apertures (147*a*, 147*b*, 147*c*, and 147*d*). As shown in FIG. 12B, which is a top cross-sectional view of the housing, each aperture (top apertures 147*a* and 147*b* are shown) extends from the outward-facing surface 142 to the body-facing surface 144. From the outward-facing surface 142 to the body-facing surface 144 the apertures can be about 2 cm to about 0.5 cm, or about 1.5 cm to about 1 cm.

There are various ways to connect an attachment member to the housing having apertures as shown in FIGS. 12A and 12B. For example, an attachment member that is a cord can enter aperture 147*b* from the outward-facing surface 142, continue along the body-facing surface 144 parallel to right side 149 and then exit through aperture 147*d*. The length of cord that extends away from apertures 147*b* and 147*d* can form a continuous loop from the right side of the housing and along the right side of the head, where the proximal end of the loop can attach to the ear or to a speaker enclosure of a headphone. A corresponding arrangement can be provided on the left side of the housing.

In other modes of attaching, the cord may also enter aperture 147*b* from the outward-facing surface 142, continue along the body-facing surface 144 parallel to top side 145 and then exit through aperture 147*a*. The length of cord that extends away from aperture 147*a* can extend distally to form a continuous loop from the left side of the housing and along the left side of the head, and then return in to aperture 147*c* from the outward-facing surface 142, continue along the body-facing surface 144 parallel to bottom side 146 and then exit through aperture 147*a*. The length of cord that extends away from aperture 147*d* can extend distally to form a continuous loop from the right side of the housing and along the right side of the head, and then return into aperture 147*d*.

In other modes of attaching, the cord may enter any aperture from the body-facing surface 144 and then continue along the outward-facing surface 142, parallel to either the top or bottom (145, 146) or left or right (148, 149) sides. In some embodiments the housing includes at least one channel (e.g., tunnel) through which the cord is movable wherein the at least one channel is integrated in the housing. For example, the housing can include one or more channels along any part of the periphery of the housing. Alternatively, one or more channels can be present across all or a portion of the outer surface of the housing, across all or a portion of the inner surface of the housing, or through the central portion of the housing. The channel can have entry and exit points for the cord, and therefore can be of a predetermined length, such about 0.5 cm or greater, or 1 cm or greater. The length of a channel can be as great as the entire periphery of the housing, or the length of the upper or lower portions of the housing. The housing can include, or be associated with, one or more attachment member tensioning feature(s) such as illustrated in FIGS. 13A-15B. The tensioning features can provide a mechanism for adjustment (lengthening or shortening) of the attachment member such as a cord so the user can achieve a desired tension between the housing and the ears or the speaker enclosures of headphones.

Figure 13A:
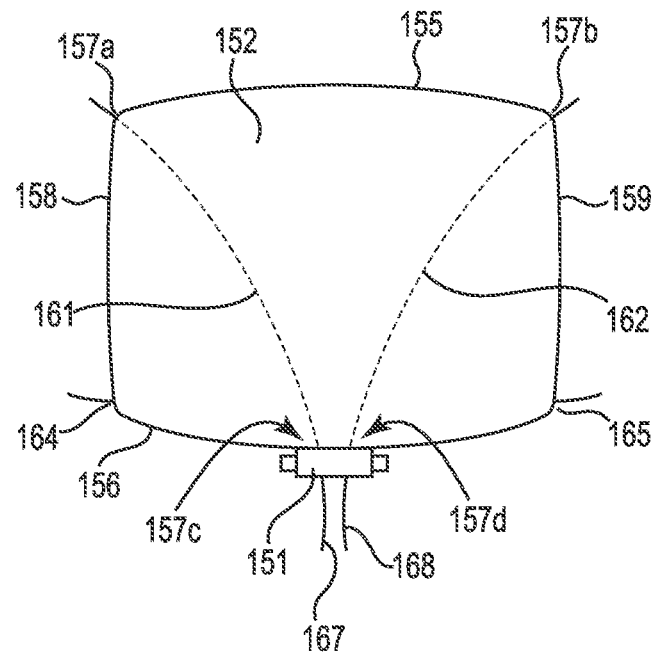
FIGS. 13A and 13B illustrate rear and bottom views of an embodiment of housing for a vibration speaker or transduction member
Figure 13B:
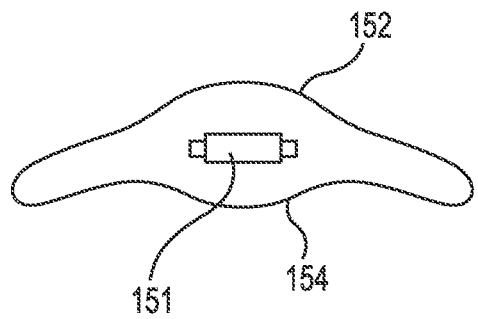

As an example, FIG. 13A shows a view of a housing with outward-facing surface 152, with upper 155, lower 156, left 158, and right 159 sides. Within the housing are two channels (161 and 162, shown as dashed lines) sized to accommodate the attachment member (e.g., cord). Channel 161 can have an entry/exit point 157a on the left side 158 of the housing, near the upper side 155; likewise, channel 162 can have an entry/exit point 157b on the right side 159 of the housing, near the upper side 155. Channels 161 and 162 extend from 157a and 157b towards lower side 156, and towards the middle of the housing, and have an exit points 157c and 157d, respectively. Ends of the cord (167 and 168) are shown extending out of channels 161 and 162 from the bottom side 156. The cord can continue out of channels 161 and 162 (via entry/exit points 157c and 157d) and form loops from the left and right sides of the housing, and along the left and right sides of the head respectively, and then return to points 164 and 165 on the left 158 and right 159 sides of the housing, near the lower side 156, where the cord may be fixed to the housing. The length of the loops may be adjusted by feeding a length of cord through the channels. Further, the cord can be secured using a depressible clamping member 151, which can include openings for each cord, and which can clamp the cord in place using a spring mechanism. FIG. 13B shows a view of a housing from the lower side, with outward-facing surface 152 and body-facing surface 154.

Figure 14A:
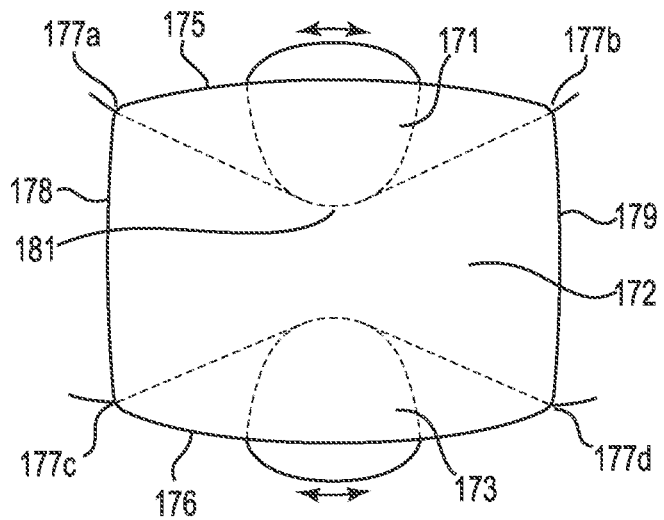
FIGS. 14A and 14B illustrate rear and top views of an embodiment of housing for a vibration speaker or transduction member
Figure 14B:
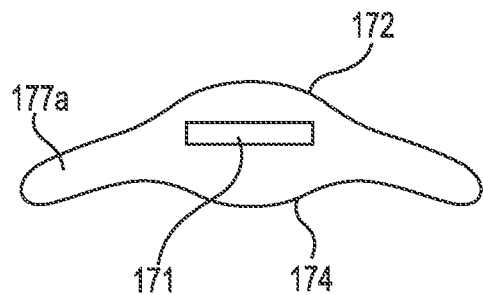

In some embodiments, the housing includes one movable member(s), such as a member that is rotatable in place, or movable in relation to the housing, which allows the extension and/or retraction of a length of cord from the housing. As an example, FIG. 14a shows a view of a housing with outward-facing surface 172, with upper 175, lower 176, left 178, and right 179 sides. Within the housing is an upper space that allows passage of the cord from an entry/exit point 177a on the left side 178 of the housing, near the upper side 175, to an entry/exit point 177b on the right side 178 of the housing, near the upper side 175. The housing also includes a movable member 171, such as a disc or dial that is rotatably immobilized by a portion of the housing. A portion of the movable member 171 can protrude from the upper side 175 of the housing 172, so that it can be manipulated by a user. Within the housing, the movable member 171 can contact a portion of the cord, for example, the rotatable member can be attached to the cord. Upon rotation of the movable member 171, the cord is pulled further into the housing, causing shortening of its length, and therefore shortening of the length of the loop from the either or both side(s) of the housing. The movable member 171 can also be rotated in the opposite direction so length of the cord is released from the housing, causing lengthening of the loop from the either or both side(s) of the housing. The lower portion of the housing can have a mirror arrangement of features, including entry/exit points 177c and 177d and movable member 173, which function to shorten and lengthen the cord in the same manner. FIG. 14B shows a view of the housing from the upper surface showing movable member 171.

Alternatively, the movable member 171 can be pushed towards the center of the housing to cause shortening of the attachment member such as a cord. For example, movable member 171 is in contact with attachment member at point 181 within the housing, and movement of the member 171 towards the center of the housing draws length of the cord within the housing to shorten its overall length outside of the housing. Member 171 can be movable within a slot formed in the housing. The lower portion of the housing can have a mirror arrangement of features, including entry/exit points 177c and 177d and movable member 173, which function to shorten and lengthen the cord in the same manner.

Figure 15A:
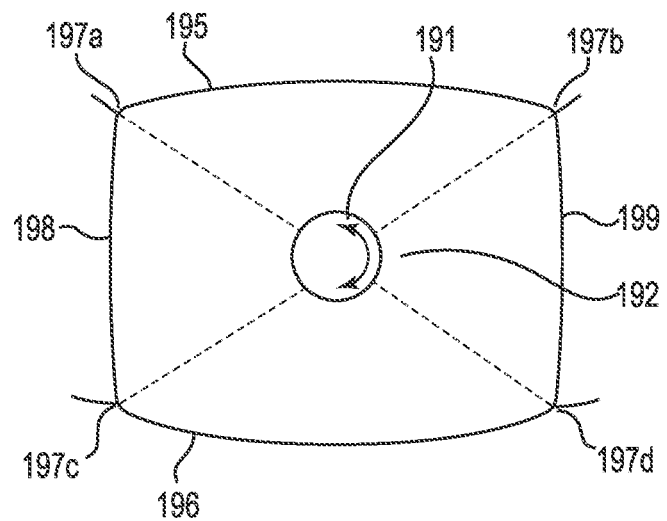
FIGS. 15A and 15B illustrate rear and top views of an embodiment of housing for a vibration speaker or transduction member
Figure 15B:
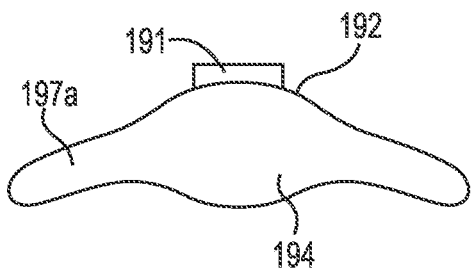

As another example of a tensioning member, FIG. 15A shows a view of a housing with outward-facing surface 192, with upper 195, lower 196, left 198, and right 199 sides. Within the housing is an upper space that allows passage of the cord from an entry/exit point 197a on the left side 198 of the housing to an entry/exit point 197b on the right side 198 of the housing. Also, within the housing is a lower space that allows passage of the cord from an entry/exit point 197c on the left side 198 of the housing to an entry/exit point 197d on the right side 198 of the housing. The housing also includes a rotatable member 191, such as a disc or dial that is rotatably immobilized by a portion of the housing, near the center of the housing. Within the housing, the cords can be attached to the rotatable member 191 and can contact a portion of the cord. Upon rotation of the rotatable member 191, the cord is pulled further into the housing, causing shortening of its length, and therefore shortening of the length of the loop from the either or both side(s) of the housing. The rotatable member 191 can also be rotated in the opposite direction so length of the cord is released from the housing, causing lengthening of the loop from the either or both side(s) of the housing. The lower portion of the housing can have a mirror arrangement of features, including entry/exit points 177c and 177d and rotatable member 173, which function to shorten and lengthen the cord in the same manner. Alternatively, length of the cord can be adjusted using two entry/exit points instead of four. For example, the length of the cord can be adjusted through any two entry points on the left 198, right 199, upper 195, or lower 196 sides.

In other embodiments, the attachment apparatus includes a tensioning member that is attachable to the speaker enclosure or band of a headphone set. For example, as another example of a tensioning member, FIGS. 19A-19B illustrate a housing 240 which can be positioned on the back of the neck of a user, over the uppermost portion of the spine, and two cord loops (242a-c, 244a-c) and extending from the sides of the housing towards and around attachment discs (245, 247) which include a tensioning mechanism to cause shortening or lengthening of the cord. The tensioning mechanism can include a dial that is attached to a portion of the cord to draw in or release the cord when the dial is turned in a clockwise or counterclockwise direction, respectively. The attachment discs (245, 247) can be attached to the outer surface of the headphone band 249 or speaker enclosures (241,243) through an adhesive or an attachment mechanism, such as a suction cup. Reference is made to FIG. 18C, illustrating use of an adhesive to attach an attachment disc with tensioning mechanism.

The housing can also include a port for an electrical connection, or electrical connections (e.g., wire) leading from the housing, to a charging outlet, headphone, smartphone, or similar peripheral device. The electrical connection can provide power and/or signal to the internal components. In other arrangements the apparatus can include a Bluetooth receiver, such as located within the housing, to provide signal to the low frequency vibration component. In this arrangement, the housing may also include a power source to drive the vibration component along with the signal. The power source could be provided by a disposable battery that is placed within the housing, or a rechargeable battery could be permanently built into the housing.

The attachment member can be in the form of a cord that is attached directly or indirectly connected to the housing. The portion of the cord that is attached to the housing is referred to as the proximal portion, and the portion of the cord that is configured for removable attachment to the ears or to speaker enclosures of a speaker set that is placed about the ears is referred to as the distal portion. The distal portion of the cord can be in the form of a loop of a size that fits around the front of the ear; for example, the proximal portion of the loop portion is configured to contact a user between the upper helix of the ear and the skull and then down underneath the ear lobe. In this portion of the loop, the cord includes a material which stiffens the cord, or makes it less flexible and more rigid, and conformable to the shape of this portion of the ear. Therefore, the cord may have a flexibility that differs along its length, being more flexible at the proximal portion near the housing, and less flexible at the distal portion.

Figure 16A:
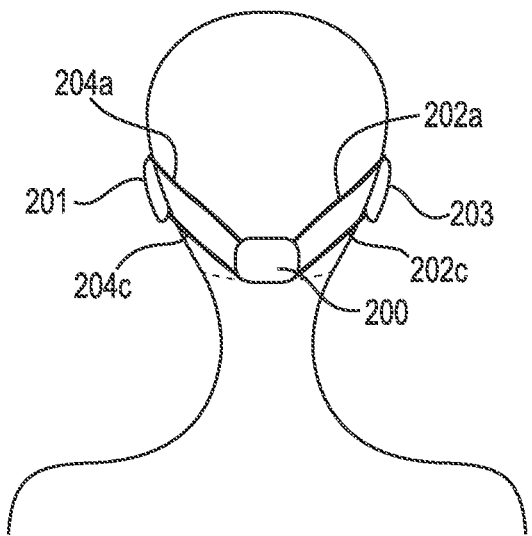
FIGS. 16A and 16B illustrate an attachable audio delivery device with housing for placement on the back of the neck, as shown attached to a user's head (back view and side view).
Figure 16B:
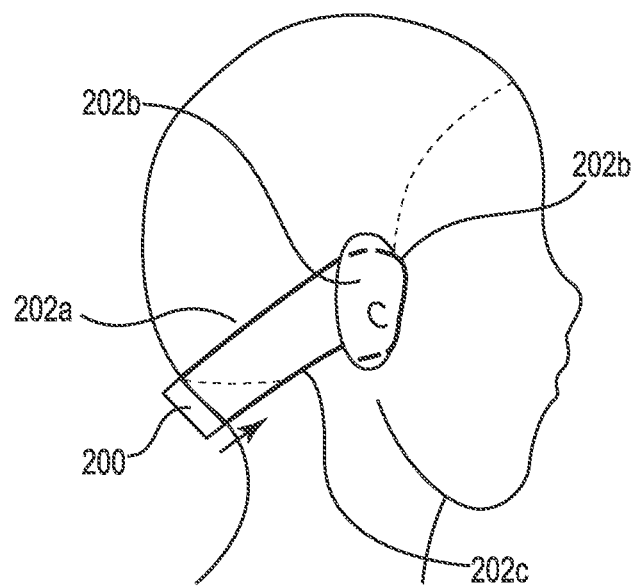
Figure 16C:
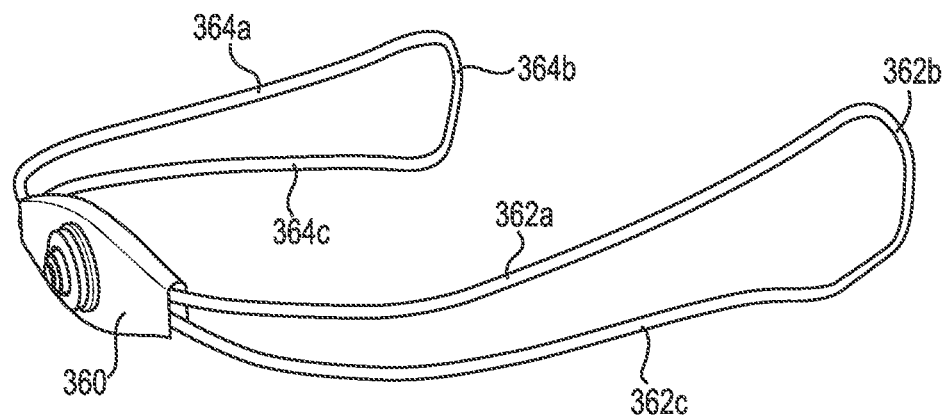
FIGS. 16C and 16D illustrate embodiments of an attachable audio delivery device with housing for placement on the back of the neck.
Figure 16D:
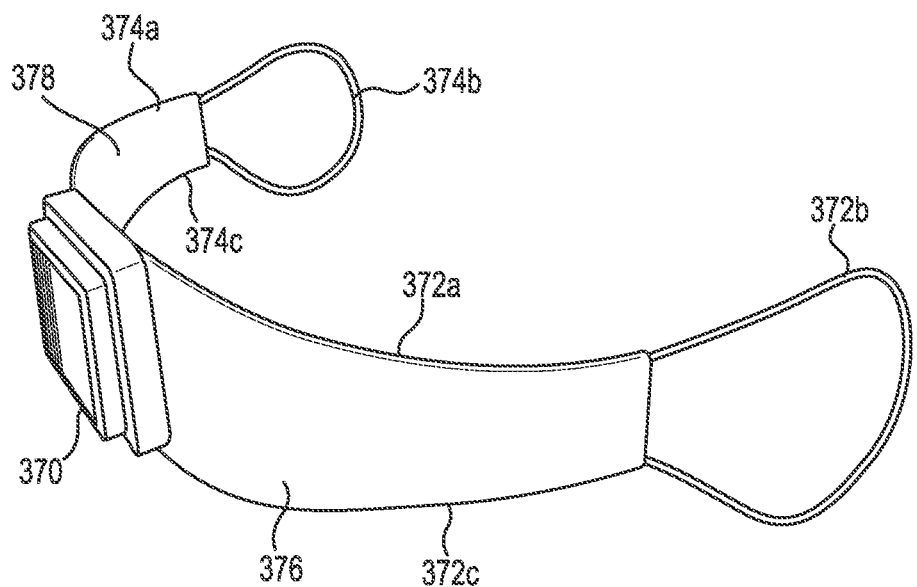

FIGS. 16A and 16B are illustrations of an attachment audio delivery device in accordance with one embodiment of the invention. The apparatus has a housing 200 which is positioned on the back of the neck of a user, over the uppermost portion of the spine, and two cord loops extending from the sides of the housing towards the ears (201, 203) of the user. The right loop has right upper portion 202a, right lower portion 202c, and a right loop distal portion 202b configured to go around the top, front, and bottom of the right ear 203. The left loop correspondingly has left upper portion 204a, left lower portion 204c, and a left loop distal portion 204b (not shown) configured to go around the top, front, and bottom of the left ear 201. The distal portion of the loop around the ear (202b, 204b) can be of the same material and construction portions 202a and 202c, and 204a and 204c, or can be of a different material and/or construction. If of a different material and/or construction, the distal portion of the loop around the ear (202b, 204b) can have one or more of the following properties to facilitate placement around the ear: increased rigidity of the cord, a different texture or material on the outside of the cord, and/or a different shape and/or thickness of the cord.

Similar to the device shown in FIGS. 16A and 16B, the device of 16C includes housing 360 for the vibration component, with right and left loops (362a-c, 364a-c) configured to go around the ears or speaker enclosures at their distal ends. The device of 16D includes housing 370 for the vibration component, with right and left loops (372a-c, 374a-c) configured to go around the ears or speaker enclo-sures at their distal ends, and a material, such as a fabric or plastic between the upper and lower portions of the loops (372a and c, and 374a and c).

Figure 17A:
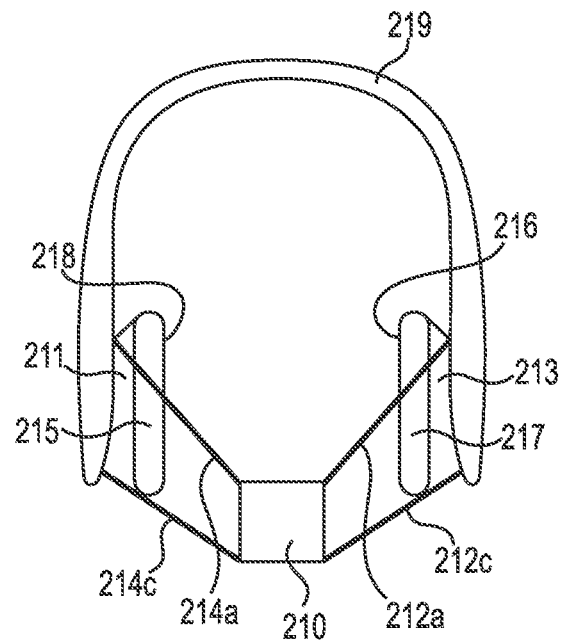
Figure 17B:
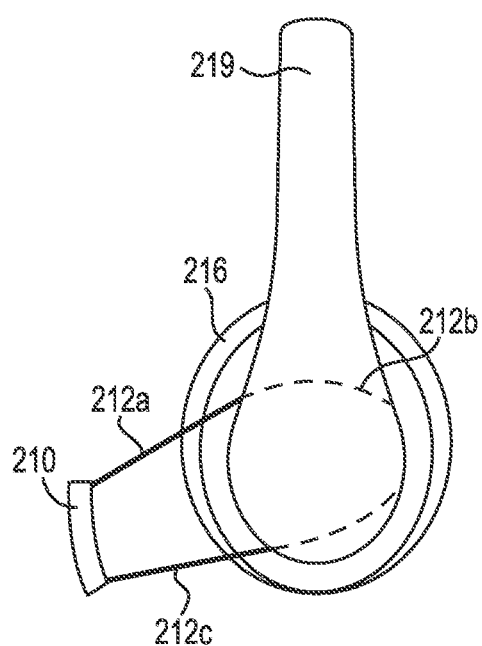
Figure 17C:
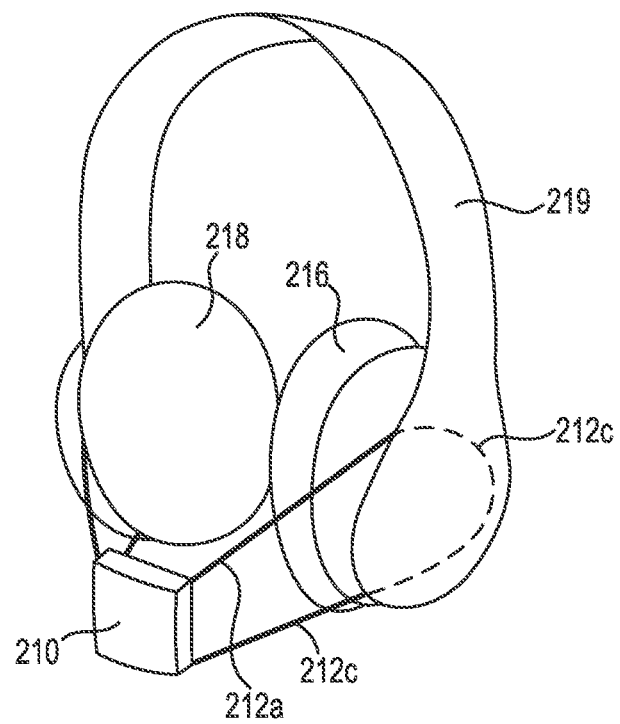

FIGS. 17A-17C are illustrations of an attachment audio delivery device in accordance with one embodiment of the invention, attached to a headphone set. The apparatus has a housing 210 which is positioned on the back of the neck of a user, over the uppermost portion of the spine, and two cord loops (212a-c, 214a-c) and extending from the sides of the housing towards and around rigid speaker enclosures (211, 213) of a headphone set. The rigid speaker enclosures (211, 213) can be between ear padding for the headphones and a headphone band 219. The right loop has right upper portion 212a, right lower portion 212c, which do not contact the speaker enclosure of the headset. The right loop also has portion 212b, which is configured to contact the speaker enclosure on it upper, forward, and bottom portions. The distal portion of the loops (212b, 214b) around the rigid speaker enclosures can have one or more of the following properties to facilitate its placement around the enclosures: increased rigidity of the cord, a different texture or material on the outside of the cord, and/or a different shape and/or thickness of the cord.

Similar to the device of FIGS. 17A-17C, the device of FIG. 17D includes housing 380 for the vibration component, with right and left loops (382a-c, 384a-c) configured to go around speaker enclosures (383, 385) at their distal ends, and a material, such as a fabric or plastic between the upper and lower portions of the loops (382a and c, and 384a and c).

Figure 18A:
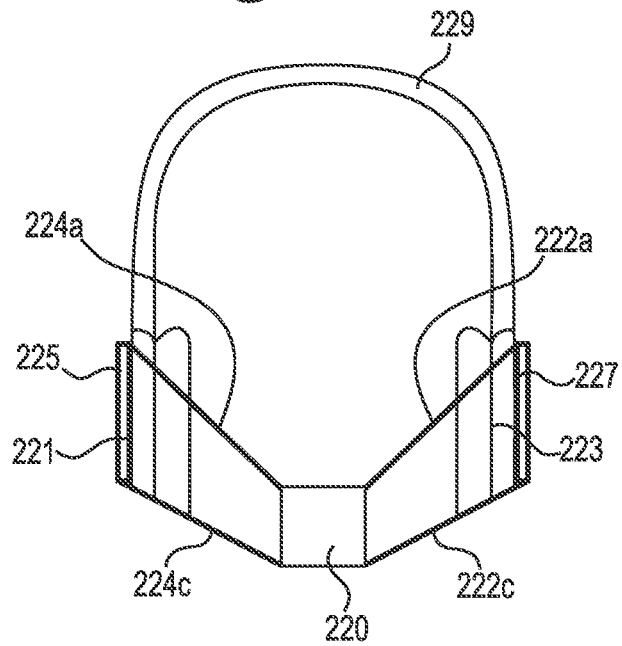
FIGS. 18A-18E are front, perspective and side views of embodiments of an attachable audio delivery device with housing for placement on the back of the neck, the device attached to a headphone set. [0034A]
Figure 18B:
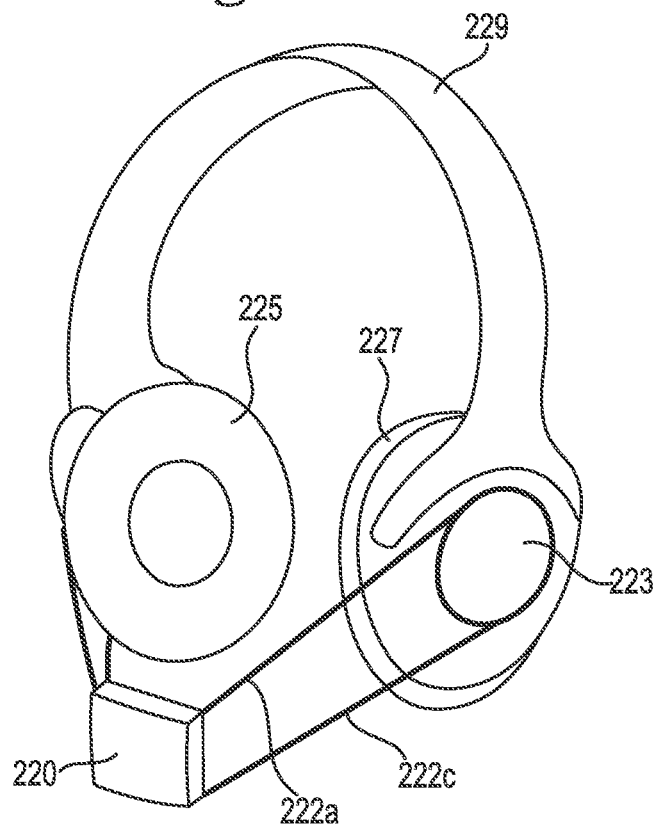
Figure 18C:
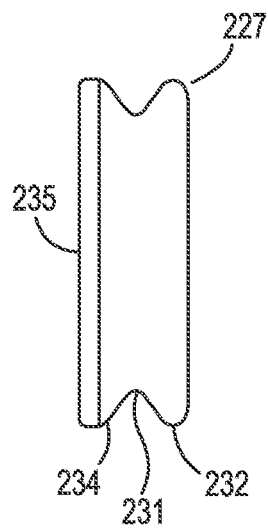
Figure 18D:
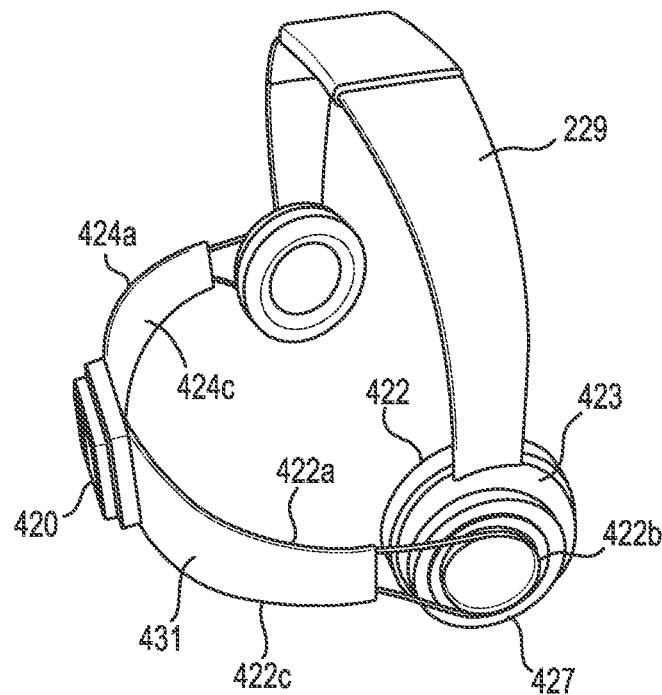
Figure 18E:
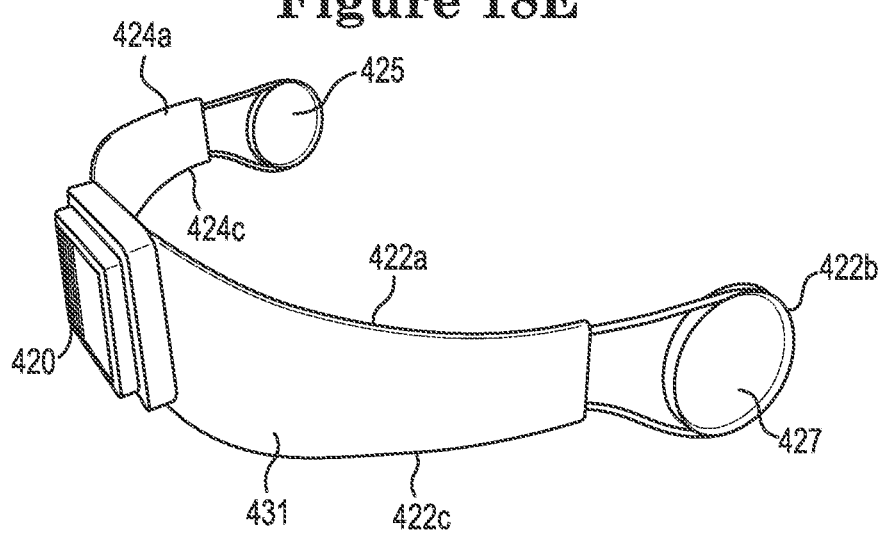
Figure 19A:
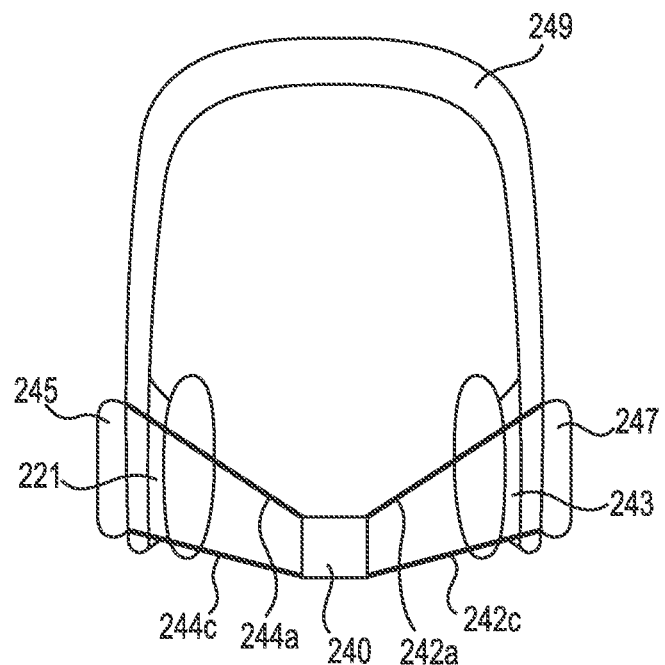
FIGS. 19A-19B are front and side views of another embodiment of an attachable audio delivery device with housing for placement on the back of the neck attached to a headphone set.
Figure 19B:
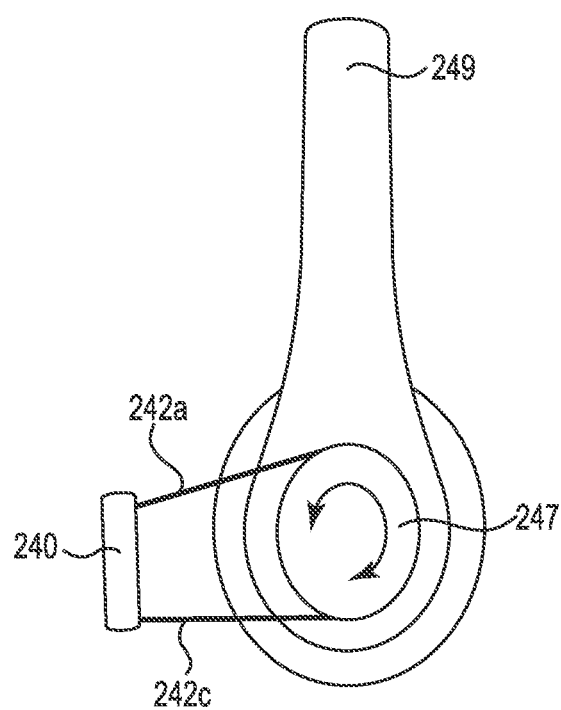

FIGS. 18A-18C are illustrations of an attachment audio delivery device in accordance with another embodiment of the invention, attached to a headphone set. The apparatus has a housing 210 which is positioned on the back of the neck of a user, over the uppermost portion of the spine, and two cord loops (222a-c, 224a-c) and extending from the sides of the housing towards and around attachment discs (225, 227). The attachment discs (225, 227) are attached to the outer surface of the speaker enclosures (221, 223) through an adhesive or an attachment mechanism, such as a suction cup. For example, with reference to FIG. 18C, the attachment disc 227 can have a speaker-facing face 235 with an adhesive that can contact the outward-facing face of the speaker enclosure 223. An adhesive lining can be peeled away to expose the adhesive so a user can apply the disc 227 to a speaker enclosure. The disc 227 can also include a groove 231 around all or part of the circumference of the disc, defined by two ridges (234, 232). The attachment member can be looped around disc 227 and held within the groove 231.

Figure 9A:
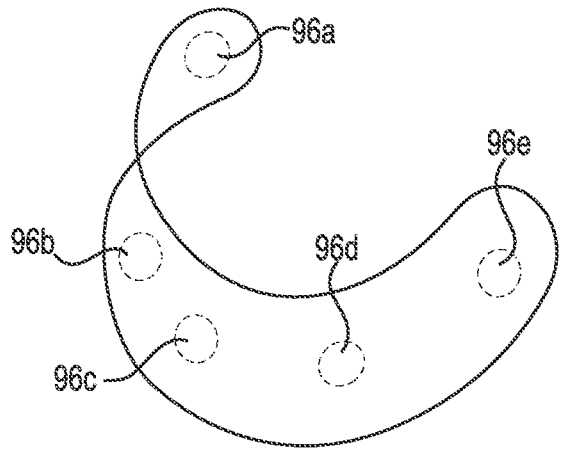
FIGS. 9A-9B illustrate perspective and side views of a wearable monitoring device that contains physiological sensors and therapeutic delivery components.
Figure 9B:
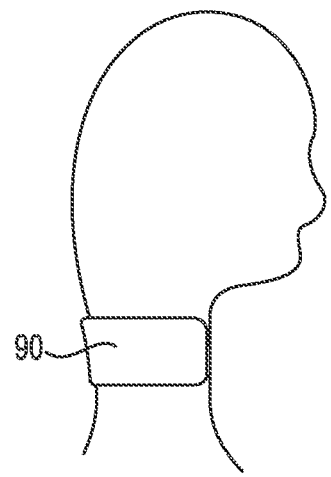

FIGS. 9A and 9B illustrate a wearable audio delivery and monitoring device 90 that is placed around the back of neck, and not over the ears, and contains one or more speakers, physiological sensors and/or therapeutic delivery components 96. Output information may be transmitted to a user's computer or smartphone so the user can utilize the information to increase performance. In related embodiments, due to the close proximity or contact with the user's skin, the devices taught herein include sensors that detect body temperature, humidity levels, chemical levels emitted by the body and detectable at skin level and other physiological functions that are detectable noninvasively and can be used to assess the health of the user.

In yet other embodiments, the disclosure provides an integrated audio delivery apparatus. The term "integrated" refers to arrangements where the housing including the vibration transduction component configured for placement at the back on the neck is non-removably attached to speaker components configured for use in or about the ear, such as headphones and earbuds. In some embodiments, the integrated audio delivery apparatus includes a housing including a vibration speaker or vibration transduction component configured to be placed on the back of the neck and over the spine, right and left ear bud or headphone speaker enclosures for the ear, and right and left attachment members connecting the housing to the right and left ear bud or headphone speaker enclosures.

Figure 1B:
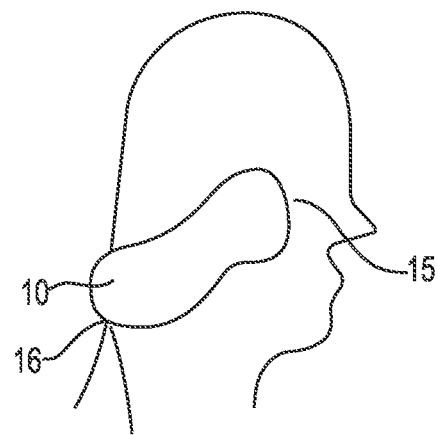

In one embodiment of an integrated apparatus is illustrated in FIGS. 1A and 1B. FIGS. 1A and 1B illustrate a wearable audio delivery and/or monitoring device 10, such as over-the-ear headphones, that incorporate vibration speakers or similar transduction members, as well as physiological sensors 16. The device is designed to be placed on the back of the neck and extends to the ears. This wearable device can be connected to an output device by a cable, wire, or wireless methods. Other items such as a control board, audio file, amplifier, equalizer, battery, wireless or similar components 12 can be incorporated into the device, and can include controls 22 for power, volume selection, LED, and charger. The over-the-ear speakers 14a and 14b can be similar to existing commercially available over-the-ear devices, and delivery methods. Arms (13a, 13b) can extend between the speakers (14a, 14b) and a housing 31. The clamp and compression attachment method of FIGS. 1A and 1B can be similar to behind the neck earmuffs that include a tension member capable of rolling up when not in use and providing tension against the head when in use. This allows for the device to be held in place on the back of the neck and does not require an over the top head-band component.

Figure 1C:
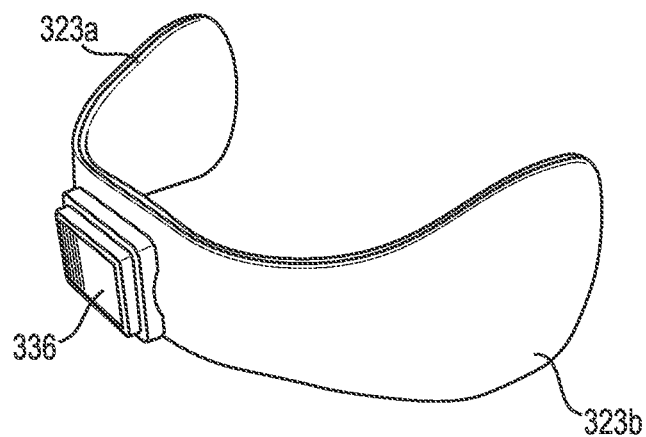
FIGS. 1C-1D illustrate perspective view of a wearable audio and vibrational delivery device that includes a vibration speaker and arms that extend over the ears but in FIG. 1D the arms are attached to over the ear speakers.
Figure 1D:
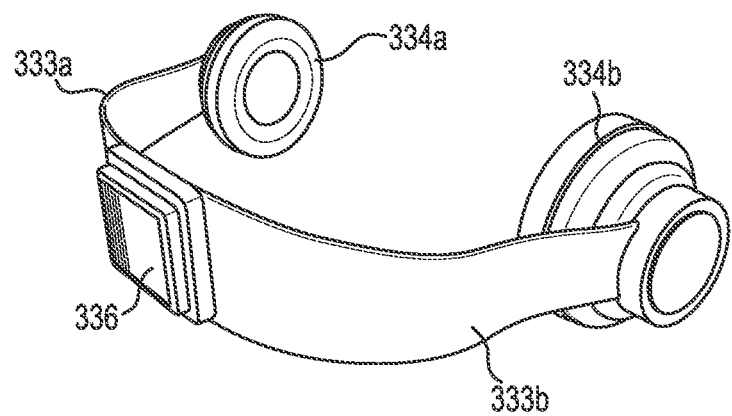

In related embodiments, the devices illustrated in FIGS. 1C and 1D can also include portions that similar to behind the neck earmuffs that include a tension member. For example, in FIG. 1C the apparatus includes a vibration speaker 326 and arms (323a, 323b) that extend over the ears, but that do not necessarily include in-ear or over-the-ear speakers. In FIG. 1D the apparatus includes a vibration speaker 336 and arms (333a, 333b) that extend over the ears attached to over the ear speakers (334a, 334b).

Figure 2A:
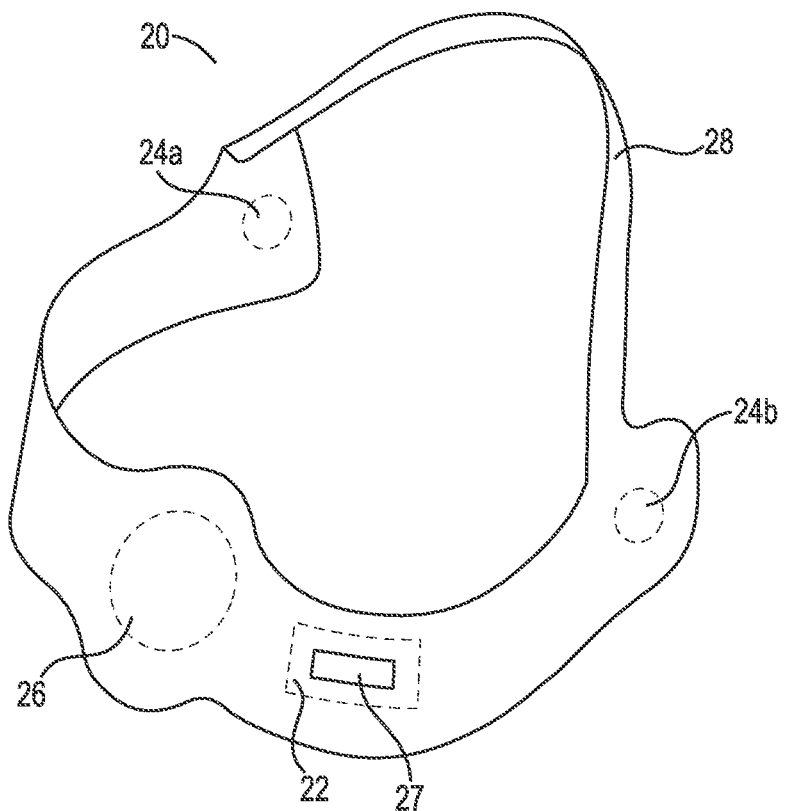
FIGS. 2A-2B illustrate perspective and side views of a wearable audio and vibrational delivery or monitoring device that includes an adjustable headband embodiment that is placed over the head.
Figure 2B:
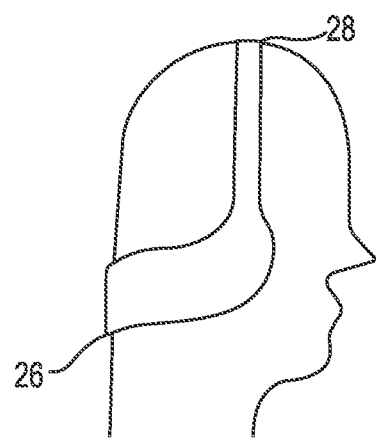

In further detail, FIG. 2 illustrates a wearable audio delivery and/or monitoring device 20 with features and functionalities similar to the device of FIG. 1. In this embodiment, the wearable audio delivery and/or monitoring device 20 includes an over the head member 28 to help keep the device in place. The device 20 can also include vibration speakers or similar transduction members, or physiological sensors 26; a control board, audio file, amplifier, equalizer, battery, wireless or similar components 22; controls 22 for power, volume selection, LED, and charger; and over-the-ear speakers 24a and 24b.

Referring now to FIG. 3, shown is an integrated wearable audio delivery and/or monitoring device 30 that incorporates vibration speakers 36 or similar transduction members, and/or monitoring sensors, into headphones that go around the back of the head and to the ears, is described. The device 30 can include attachment arms (33a, 33b) between the earphones (34a, 34b) and a housing 31 around the vibration speakers 36 or similar transduction members, and/or monitoring sensors. In an example embodiment, the control board 32 and other components can be placed in a separate housing and connected to an audio output device 37, thus decreasing the weight and size of the wearable audio delivery and monitoring device 30.

Figure 4:
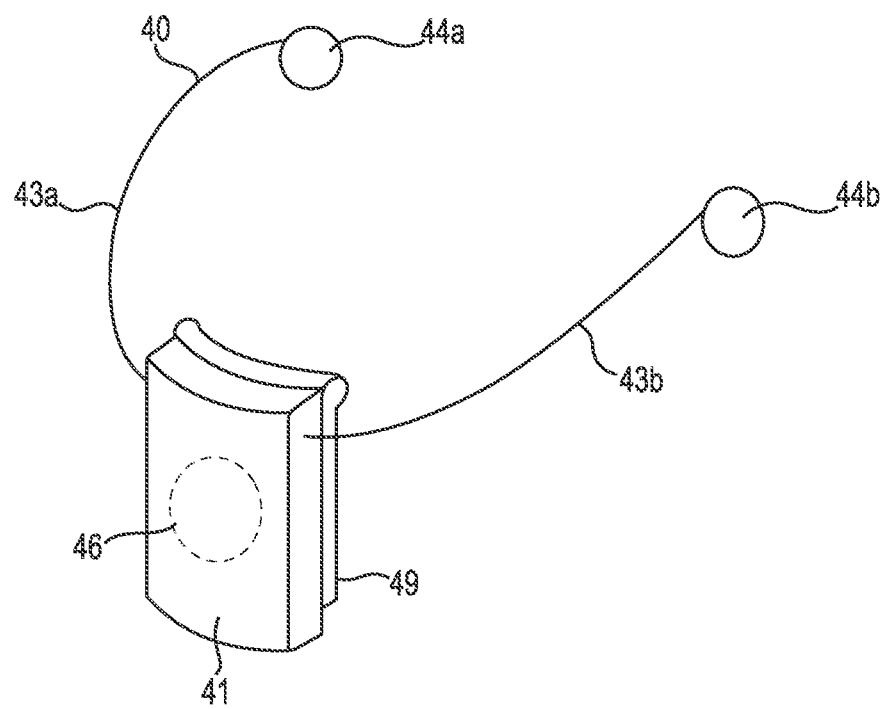
FIG. 4 illustrates a wearable audio and vibrational delivery or monitoring device that includes a system of attaching vibration speakers or similar transduction members via a wired or wireless connection, in or over the ear buds, and placed on the back of the neck.

Referring to FIG. 4, show is a wearable audio delivery and/or monitoring device 40 that incorporates a system of attaching vibration speakers 46 or similar transduction members, and/or sensors configured for placement on the back of the neck, and also including in or over the ear buds (44a, 44b), which can be connected to the audio output through wired or wireless features. The vibration speakers 46 or similar transduction member may be within a device housing 41, which can be attached directly to the collar, hatband or inside a pouch located in the collar with the use of a clip 49 or similar mechanism.

Figure 5:
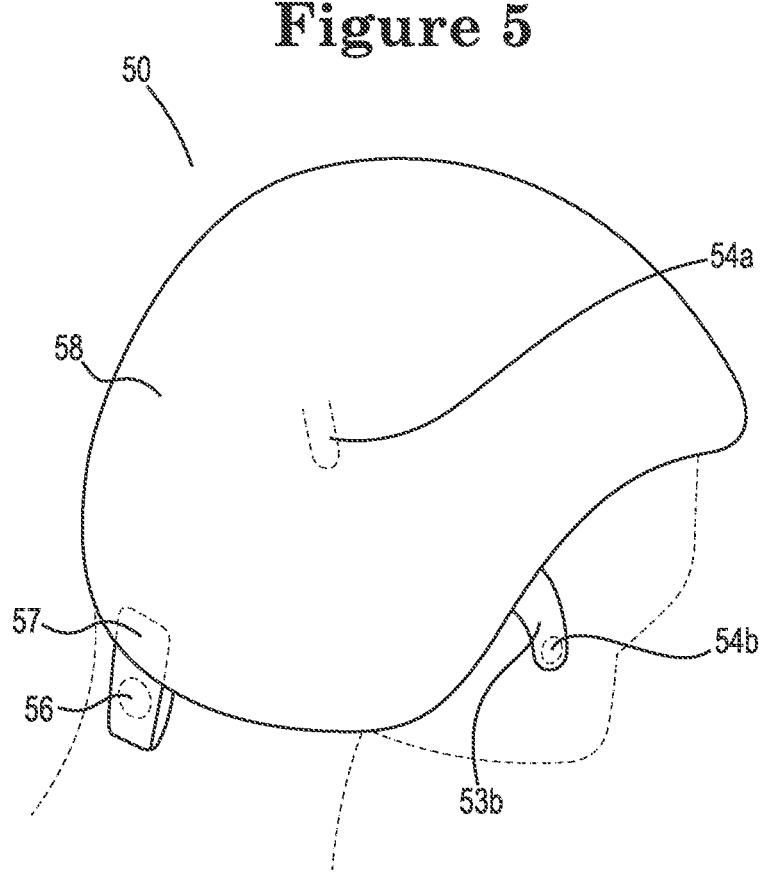
FIG. 5 illustrates a wearable audio and vibrational delivery or monitoring device that includes vibration speakers or transduction members on the back of the neck and into an audio system built inside a helmet.

FIG. 5 shows a wearable audio delivery and monitoring device 50 that incorporates a vibration speaker 56 or similar transduction members, and/or health monitoring sensors, placed on the back of the neck and associated with the back of a helmet or hat 58, such as by attachment tab 57. Ear buds (54a, 54b), can be connected to the audio output through wired or wireless features, and optionally attached to the side of the helmet or hat 58 with attachment tab 53b (attachment tab 53a not shown). The helmet or hat 58 may be worn during activities requiring a helmet such as skiing, snowboarding, hockey, or other similar activities.

Figure 7A:
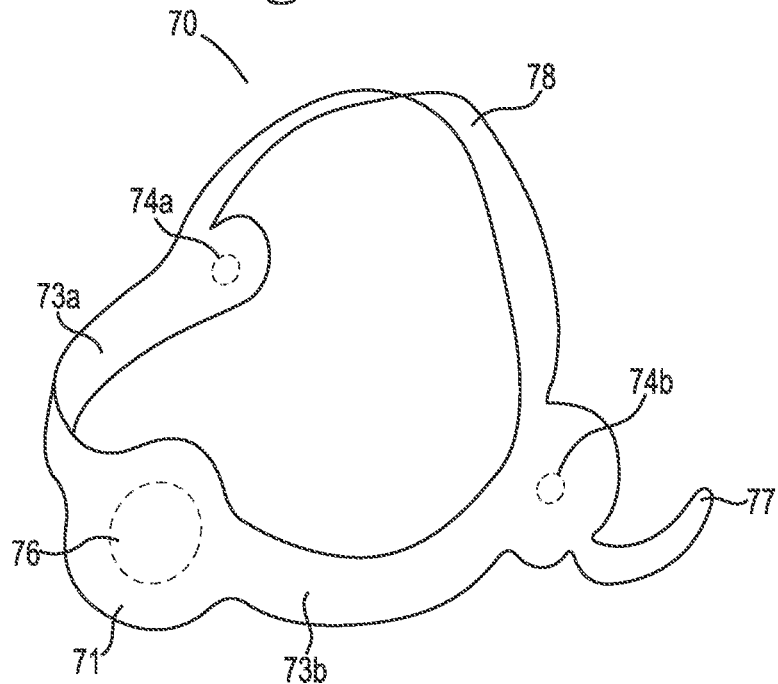
FIGS. 7A-7B illustrate perspective views of a wearable audio and vibrational delivery or monitoring device that includes vibration speakers or similar transduction members on the back of the neck.

Referring now to FIG. 7A, a wearable audio delivery and/or monitoring device 70 includes vibration speakers 76 or similar transduction members located on the back of the neck, is described. The device 70 also includes an over the head member 78 to help keep the device in place, in or over-the-ear speakers 74a and 74b, and attachment arms (73a, 73b) between the earphones and a housing 71 around the vibration speaker 76. In an example embodiment, the wearable audio delivery and monitoring device 70 includes a microphone 77 to communicate with others, such as those used in gaming. In an example embodiment, wearable audio delivery and monitoring device 70 is capable of connecting to a gaming system such as Xbox®, PS3®, games on a smartphone or handheld device, or any other similar device. The audio sensory information and vibrational energy generated by signals from the game may be delivered to the user through wearable audio delivery and monitoring device 70. In an alternative embodiment, users using electronic devices to practice flying or driving may wear a wearable audio delivery and monitoring device 70. In still another alternative embodiment, users can communicate with professionals such as doctors to receive and deliver diagnoses and therapies.

Figure 7B:
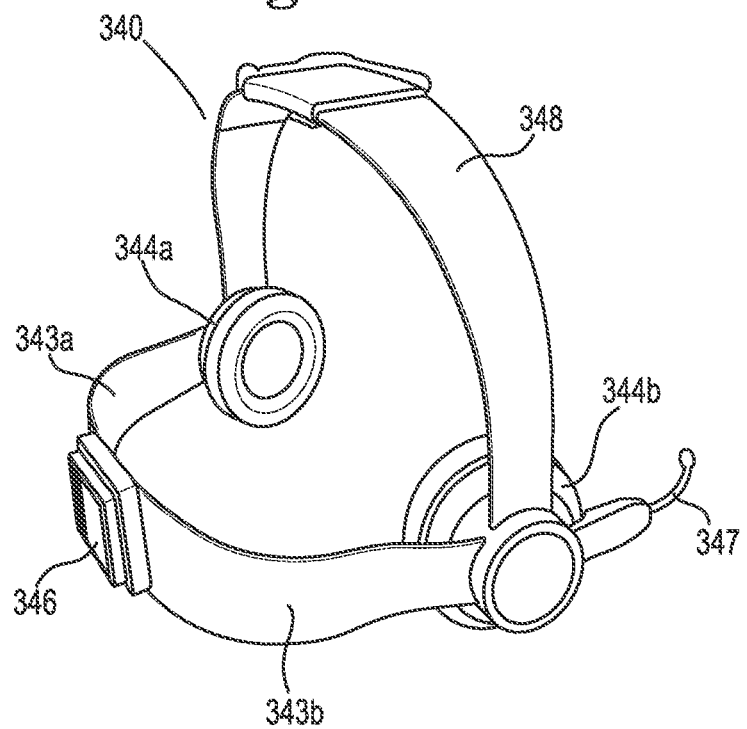

Similar to FIG. 7A, of device 340 of FIG. 7B includes a vibration speaker 346 or similar transduction members located on the back of the neck, headband 348 to help keep the device in place, over-the-ear speakers 344a and 344b, and attachment arms (343a, 343b) between the earphones and a housing 71 around the vibration speaker 76.

Figure 8A:
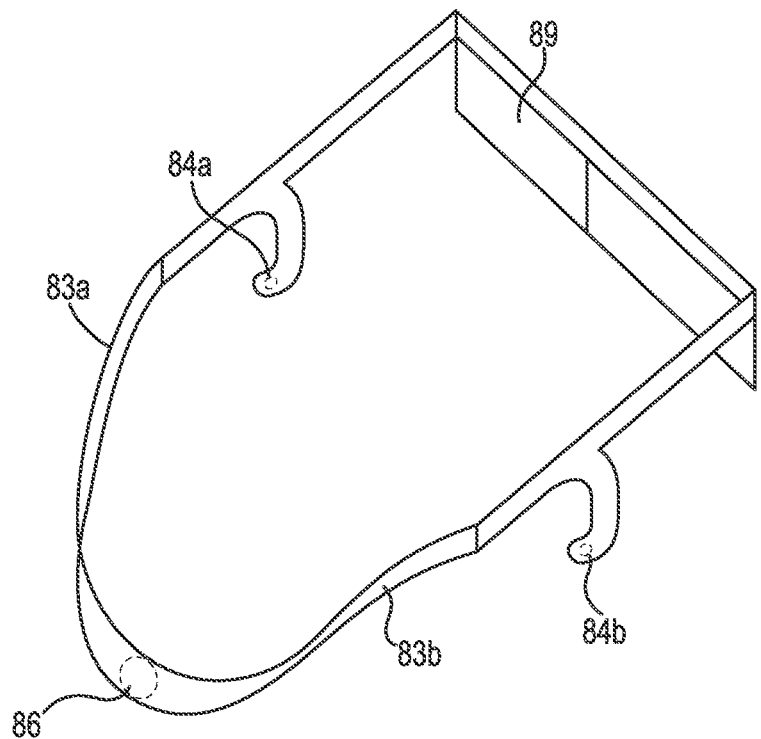
FIGS. 8A-8C illustrate perspective views and a side view of a wearable audio and vibrational delivery or monitoring device that works in conjunction with glasses or goggles or other headgear.
Figure 8B:
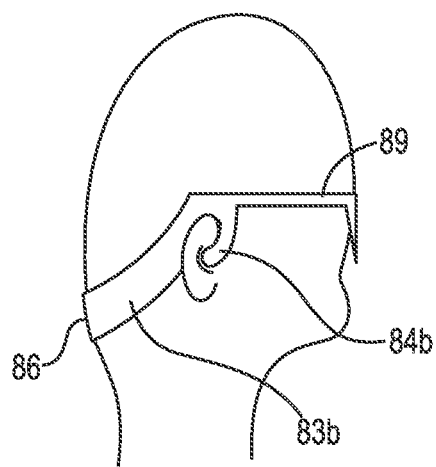
Figure 8C:
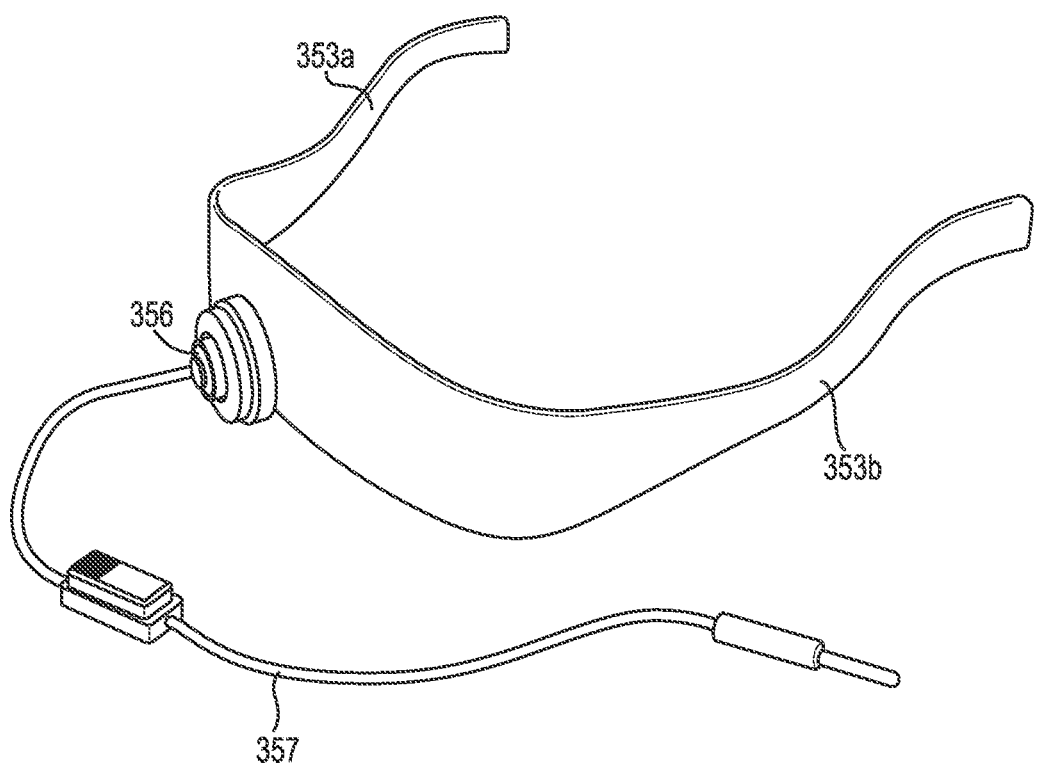

FIGS. 8A-C illustrate a wearable audio delivery and monitoring device 80 that is attached, incorporated into or in conjunction with wearing glasses 89, headsets such as for virtual reality experiences or eye covering. This embodiment holds the speakers (84a, 84b) over or near the ears, and allows for vibration speakers, sensors, or similar transduction member 86 to be attached around the back of the head. The device includes sleeves (83a, 83b) in which distal portion of the eyeglass temples (i.e., temple tips) can be placed. The sleeves can be made of an elastomeric material. The wearable glasses 89 may be glasses without corrective lenses, glasses with corrective lenses, or other lenses known in the art. An additional benefit of this embodiment could be used in conjunction with travel masks or eye covers where the vibratory members can enhance relaxation, relieve anxiety and calmness. FIG. 8C illustrates a device having transduction member 356, input cord 357, and sleeves (353a, 353b), which is not attached to eyeglasses.

Figure 20A:
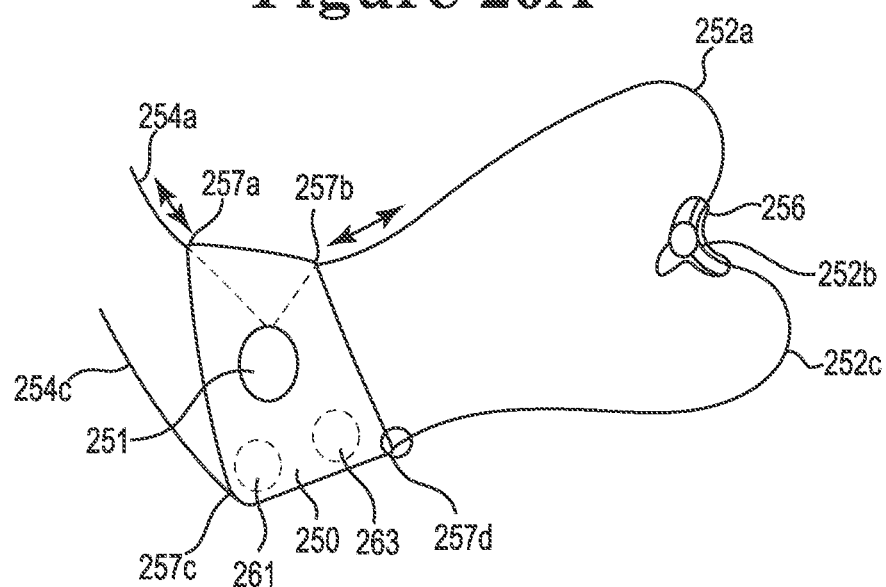
FIG. 20A is an illustration of an integrated audio delivery device including a housing for placement on the back of the neck and earbuds.
Figure 20B:
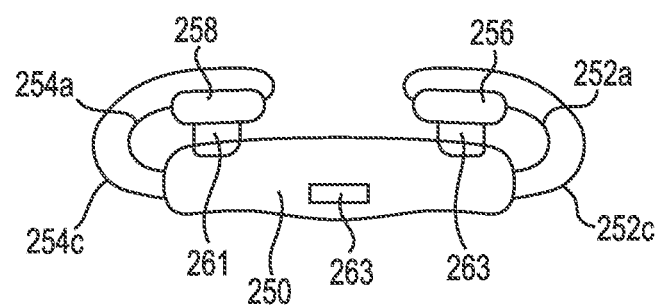
FIG. 20B is an illustration of the device in a storage configuration for battery recharging.
Figure 23:
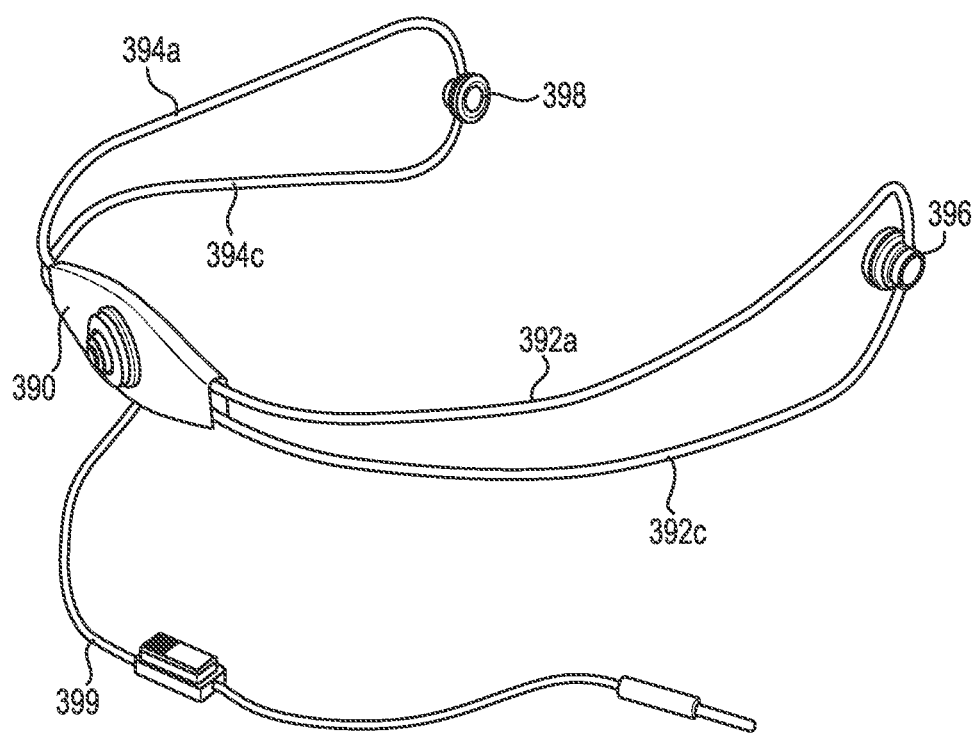
FIG. 23 is an illustration of an integrated audio delivery device including a housing for placement on the back of the neck and earbuds.

Another embodiment of an integrated apparatus is illustrated in FIGS. 20A-20B. The integrated apparatus has a housing 250 which is configured to be positioned on the back of the neck of a user, over the uppermost portion of the spine, and two cord loops (252a-c, 254a-c) extending from the sides of the housing towards the ears of the user. The right loop has right upper portion 252a, right lower portion 252c, and a right loop distal portion 252b attached or associated with an ear bud 256, which is configured to be placed within the user's right ear. A corresponding arrangement is on the left side of the apparatus (left with left upper portion 252a, left lower portion 252c, etc.). Within the housing is an upper space that allows passage of the cord from an entry/exit point 257a on the left side of the housing to an entry/exit point 257b on the right side of the housing. The lower portion of the housing can have a mirror arrangement of features, including entry/exit points 257c and 257d, or the cord can be affixed at these corners. The housing 250 can also include a rotatable member 251, such as a disc or dial that is rotatably immobilized by a portion of the housing, near the center of the housing, which, upon its rotation, can cause the cord to be pulled into the housing, or released from the housing when turned the other way. The length of the cord can be adjusted using two entry/exit points or four entry/exit points. Similar to the device of FIG. 20A, the device of FIG. 23 includes a housing 390 with vibration speaker or similar transduction members configured to be located on the back of the neck, and two cord loops (392a-c, 394a-c) extending from the sides of the housing towards the ears of the user, and ear buds (396, 398).

The earbuds as shown in the integrated apparatus of FIGS. 20A-20B can receive signal via wired or wireless components. If a wire is used to provide signal, the wire (not shown in FIGS. 20A-20C) can run along the length of the upper portion (e.g., 252a) or lower portion (e.g., 252c) of the loop of cord, towards and into the housing 250. Using a loop of cord that is flexible and stretchable, the extra length of wire can be bunched and attached to the cord at intervals along the cords length to accommodate for the stretching of the cord when it is pulled towards the ears. If a wireless component (e.g., Bluetooth) is used to provide signal, the receiver can be located as a part of the earbud assembly 256. The earbud assembly can also include a small battery, which can be disposable or rechargeable. If the battery is rechargeable, the housing 251 can include one or more induction components (261, 263) so the batteries of the ear buds can be charged when not in use. For example, with reference to FIG. 20B, the cord loops (252a-c, 254a-c), can be retracted into the housing 250 and the earbuds (256, 258) can be placed proximal to the induction components (261, 263) to charge the batteries in the earbud assemblies.

Figure 21:
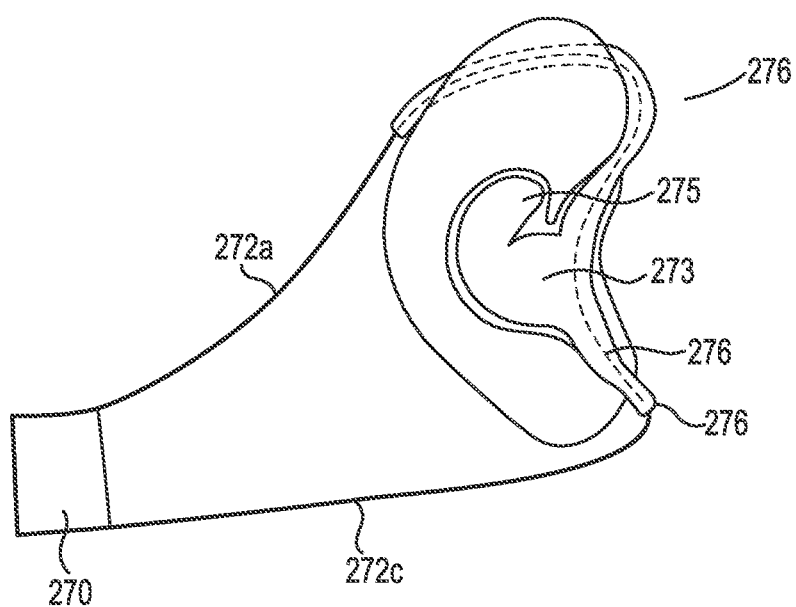
FIG. 21 is an illustration of an earbud construction for an integrated audio delivery device.

In some embodiments, an earbud member comprises features as illustrated in FIG. 21. Earbud assembly 276 includes a central portion 273 that is positioned over the ear canal and that houses an earbud speaker, and optionally battery and receiver (Bluetooth) components. Upper central portion 275 can have a shape that conforms to a portion of the concha. The earbud assembly 276 also includes a channel portion configured to accommodate a portion of the attachment member, such as a cord. For example, the channel portion can be in the form of a curved tube having a first upper portion 281 that is configured to be placed between the upper helix 288 of the ear and the head, a second upper portion 283, configured to curve downward toward the tragus of the ear, a middle portion 285 that is connected to the central portion 273 of the earbud member and configured to reside over the tragus of the ear, and a lower portion configured to be adjacent to the earlobe 286. The earbud assembly also has an upper opening 278 in which the upper portion 272a of the loop of cord enters/exits, and a lower opening 279 which the upper portion 272c of the loop of cord enters/exits. The earbud member 276 can be made from a semi-flexible semi-rigid material, such as poly(ethylene), poly (vinyl chloride) (PVC), and poly(urethane).

Figure 22A:
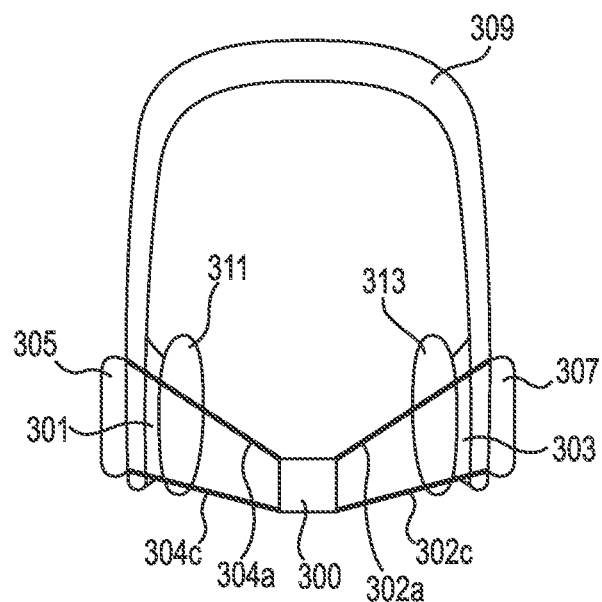
FIGS. 22A-22D are views of an integrated audio delivery device with housing for placement on the back of the neck with a headphone set.
Figure 22B:
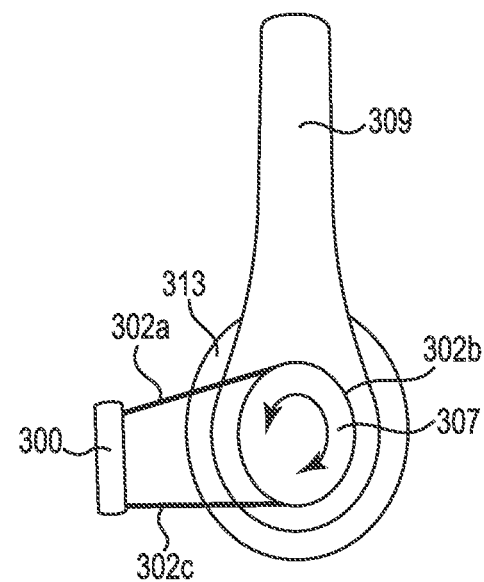

Another embodiment of an integrated apparatus is illustrated in FIGS. 22A-22D. The integrated apparatus has a housing 300 which is configured to be positioned on the back of the neck of a user, over the uppermost portion of the spine. Two cord loops (302a-c, 304a-c) extend from the sides of the housing and attach to rotatable members (305, 307), such as discs or dials, are associated with the outer surface of the headphone band 309. (Alternatively, the rotatable members (305, 307) are associated with the outer surface of the speaker enclosures (301, 303)). The right loop has right upper portion 302a, right lower portion 302c, and a right loop distal portion 302b affixed to rotatable members 305. A corresponding arrangement is on the left side of the apparatus (left with left upper portion 302a, left lower portion 302c, etc.). Referring to FIGS. 22A and 22B, in use, the user can place the housing 300 on the back of the neck and the speaker enclosures (301, 303) with soft pads (311, 313) about the ears. For example, the housing 300 with two cord loops (302a-c, 304a-c) can be at an angle in the range of about 80° to about 140°, or about 950 to about 125° to the headphone band 309.

Figure 22C:
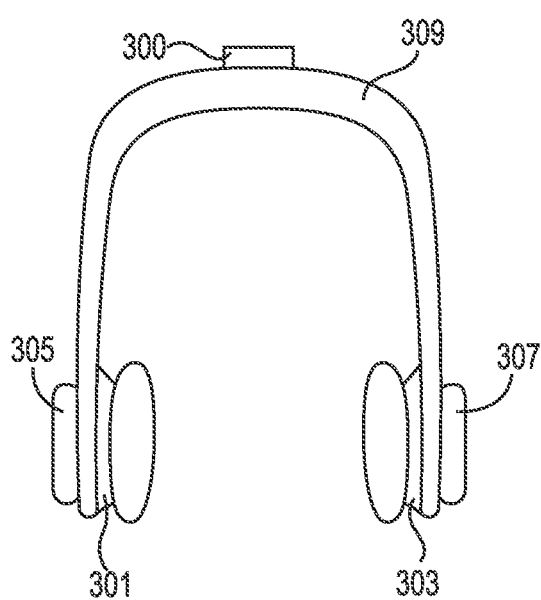
Figure 22D:
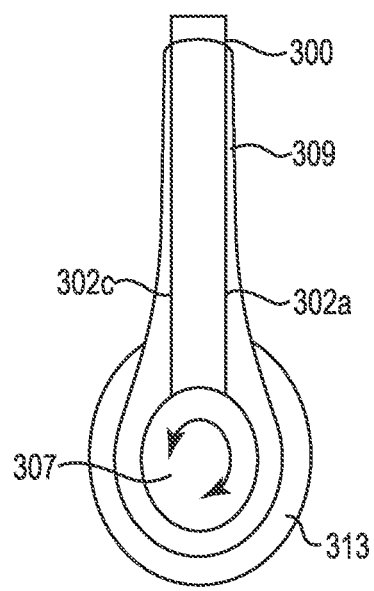

Referring to FIGS. 22C and 22D, when the vibration transduction component in the housing is not in use the user can rotate the rotatable members (305, 307) so the two cord loops (302a-c, 304a-c) are swung upwards and aligned with the headphone band 309, and so to place the housing on the outside surface of the headphone band 309. If needed, the cord loops (302a-c, 304a-c) can be loosened or tightened at the housing to provide a desired tension at the back of the neck in use, and over the top of the headphone band 309 during storage.

The various embodiments described herein improve upon existing audio and video content delivery headsets such as headphones, virtual reality, augmented reality or other such headsets that are used when playing games, listening to music or watching videos. By including a vibratory content delivery method that is held in place on the spine, the user's mobile audio experience is enhanced. Additionally, by including a place and method to release olfactory stimulation over or near the nose, we help to create a multi-sensory experience to consumers wherever they are. In a related embodiment, it is also taught herein that various forms of content, such as audio, video, vibratory, and olfactory sensory stimulation, can be created and delivered through the described embodiments to teach, improve, entertain and heal an individual. As an example, an included embodiment illustrates where a medical professional could record and deliver multi-sensory content to help a patient with a specific condition. As another example, a parent could use recorded multi-sensory content to help their child with conditions.

Referring now to FIGS. 26-36, FIG. 26 illustrates a mobile content delivery headset such as a virtual or augmented reality headset that delivers recorded content that can be seen, heard, felt and smelled. The headset receives recorded content and delivers video through a face or eyepiece or viewing display 600. Auditory content is delivered through various types of speakers or transducers that are attached or integrated into the headset system and worn over, on or near ears 601, as well as through a tactile transducer that is placed over a spine 602. It is envisioned that other auditory delivery methods such as bone conduction could be incorporated into the headset as well. An over-the-head strap 603 that holds the eyepiece 600 in place is shown. Additionally, itis envisioned that olfactory receptacles could be included in the eyepiece or system and when activated, could release smells in conjunction with the content over or near a user's nose.

Figure 26:
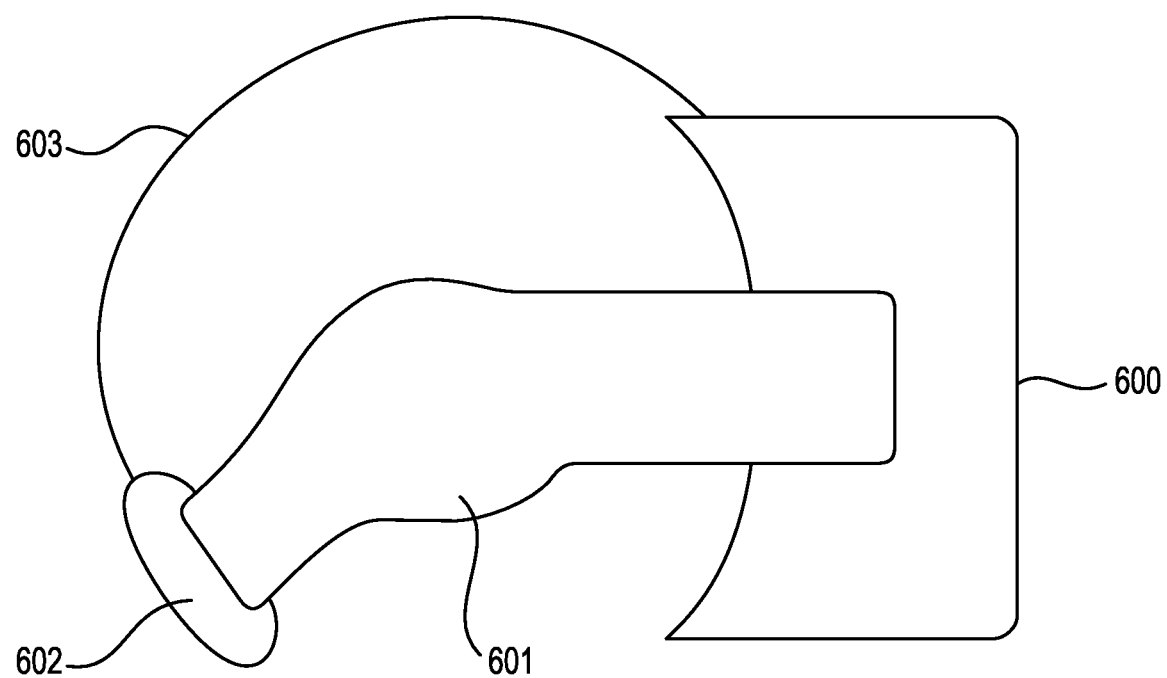
FIG. 26 illustrates a side view of a mobile content delivery headset.
Figure 27:
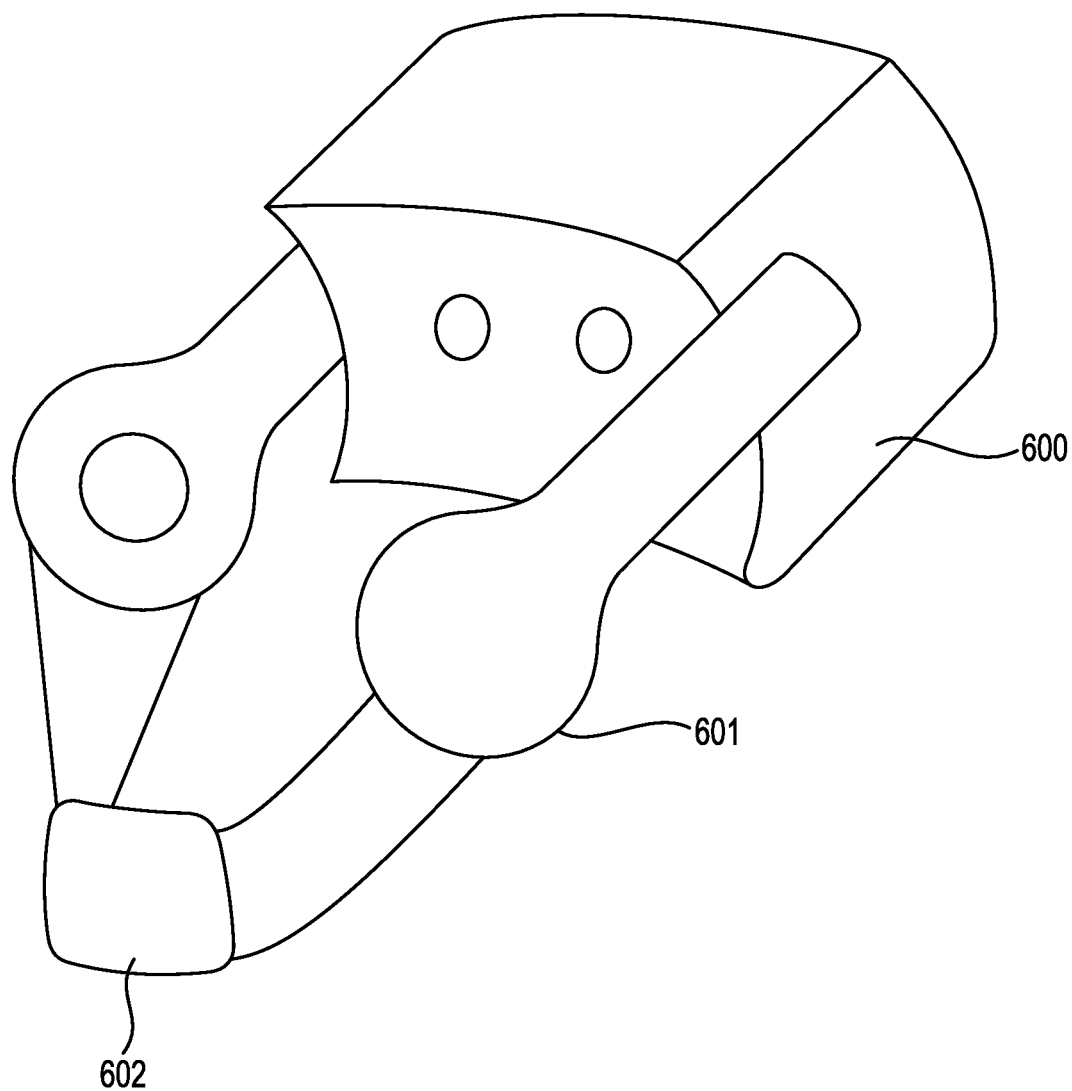
FIG. 27 illustrates a perspective view of a mobile content delivery headset.

Referring now to FIG. 27, and similar to FIG. 26, there is illustrated an example embodiment of a mobile content delivery headset such as a virtual, mixed or augmented reality headset with included visual 600, auditory 601 and tactile 602 sensory stimulation components.

Figure 28:
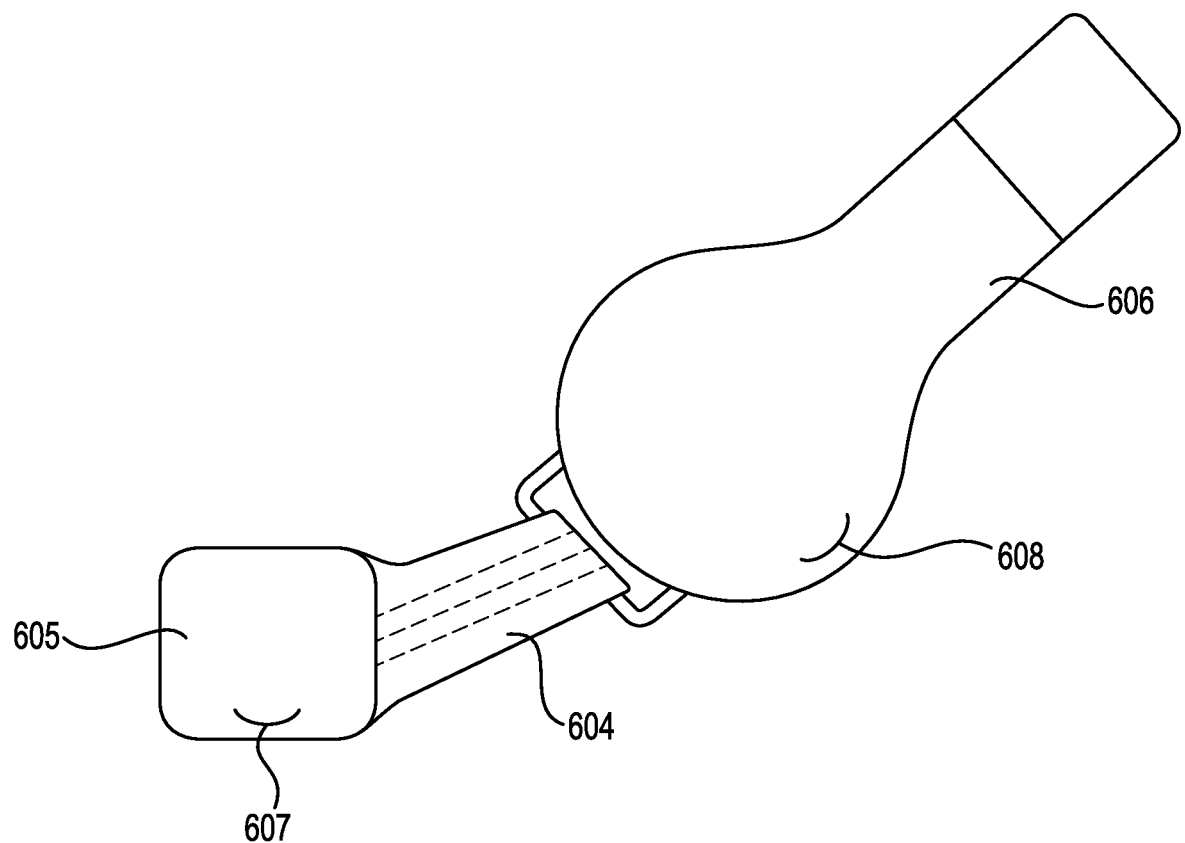
FIG. 28 illustrates a side view with details of a component attached to a mobile content delivery headset arm.

FIG. 28 illustrates an example embodiment of an adjustable connection assembly or system 604 for attaching a tactile transducer component 605 to an adjustable audio delivery arm 606 of a mobile content delivery headset. The adjustable audio delivery arm could have similar features as over the head headphones, and could be made from such materials as plastic, rubber or similar stretchable materials. The adjustable connection assembly could be made from adjustable and pliable materials such as elastic or similar. This embodiment allows the transducer to be held in place on the back of the neck and top of the spine. Additionally, it allows the transducer to move freely and deliver tactile vibrations to the user. Also shown are manual controls, such as for volume, for both the transducer component 607 and the speaker on the ears 608. This manual adjustability of each component allows the user to customize the user's audio experience.

Figure 29:
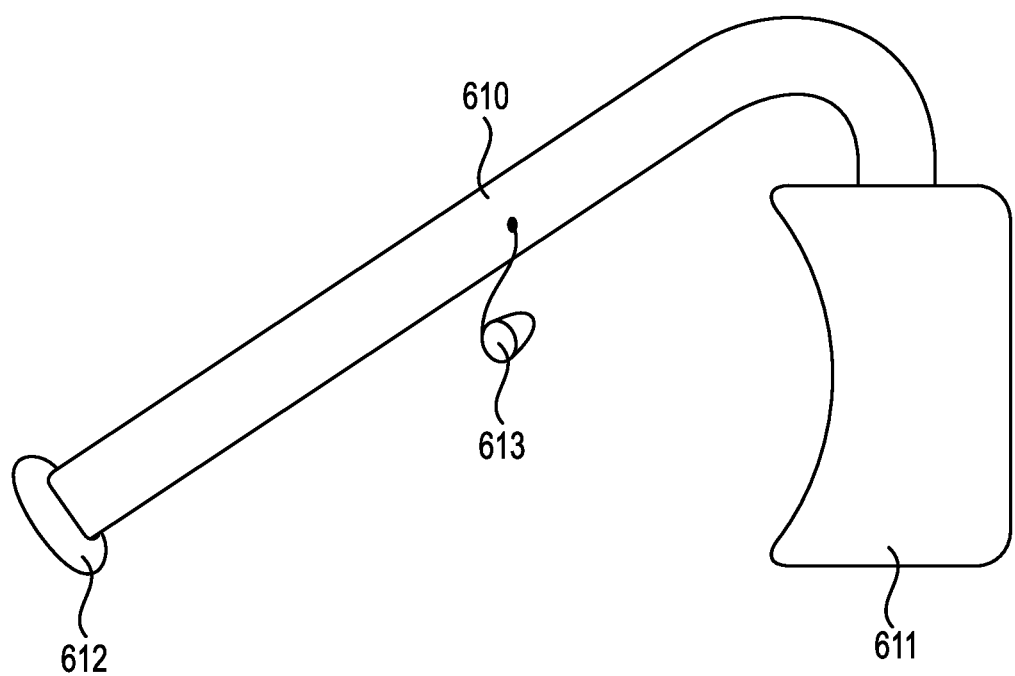
FIG. 29 illustrates a side view of another mobile content delivery headset with a different shape.

Referring now to FIG. 29, this figure illustrates a side view of a mobile content delivery system with a different shape. Rather than attaching the audio arm and earpieces 610, an in-ear earphone set 613 is provided adjacent the user's ears and to the side of the video eyepiece 611. This description illustrates how the earpieces can attach to the top of the eyepiece that hangs from the forehead and over the eyes. The benefit of this product feature allows the tactile transducer component 612 to be held in place on a user's spine without bending the audio arms.

Figure 30:
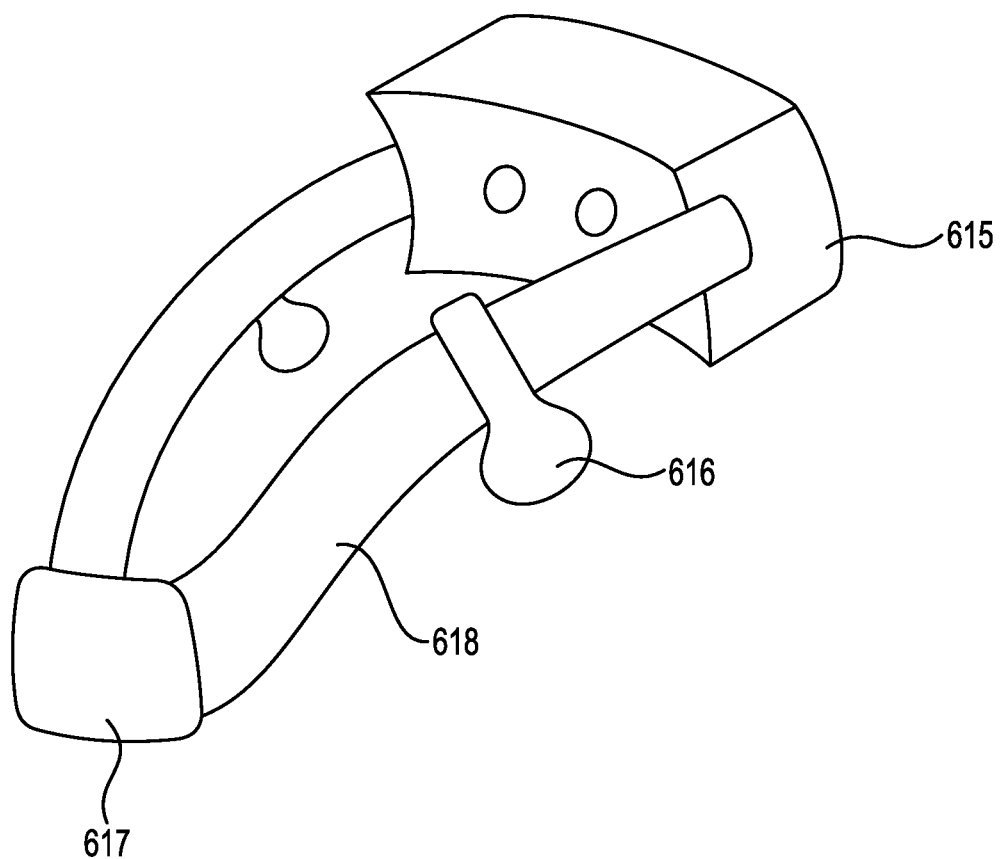
FIG. 30 illustrates a perspective view of a mobile content delivery headset that has a conforming shape to a user's head and speakers adjacent a user's ears.

FIG. 30 illustrates a mobile content delivery system that is a fully integrated system with video 615, audio 616 and tactile 617 delivery components. Construction materials are envisioned to be similar to other types of wearable electronics products. The benefit of this system is the lightweight, all-inclusive, comfortable design that molds to the user's head. Additionally, the arms have a conforming bended shape behind the ears 618 to allow the tactile transducer to be held in place on the spine.

Figure 31:
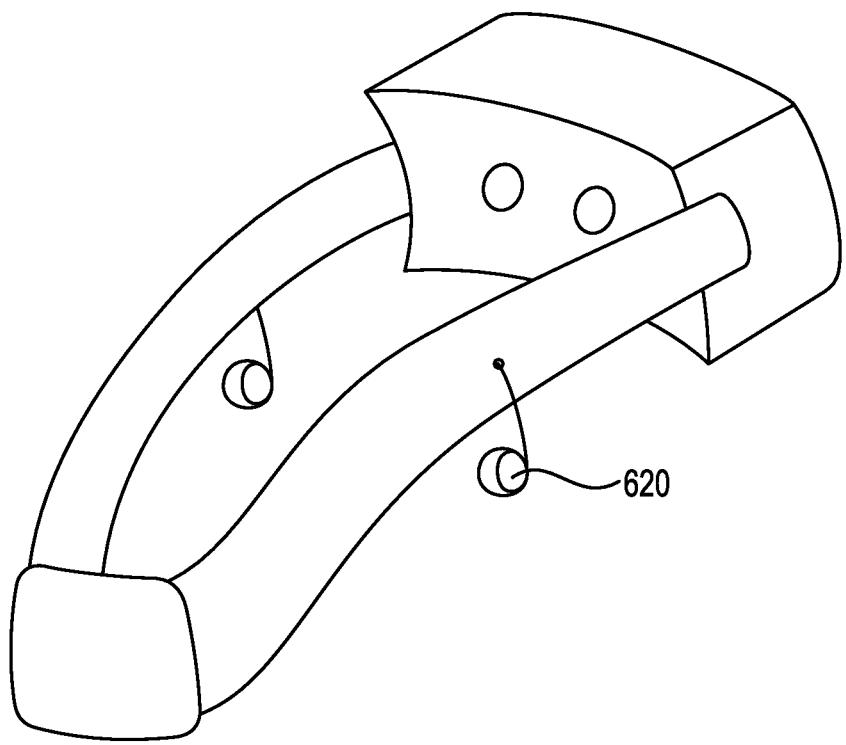
FIG. 31 illustrates similar headset to FIG. 30 with in-ear speakers for a user.

Referring now to FIG. 31, there is illustrated a mobile content delivery system with similar features as FIG. 30. The primary difference between the two is the use of in-ear speakers 620 compared to other designs that show over or even on ear speakers.

Figure 32:
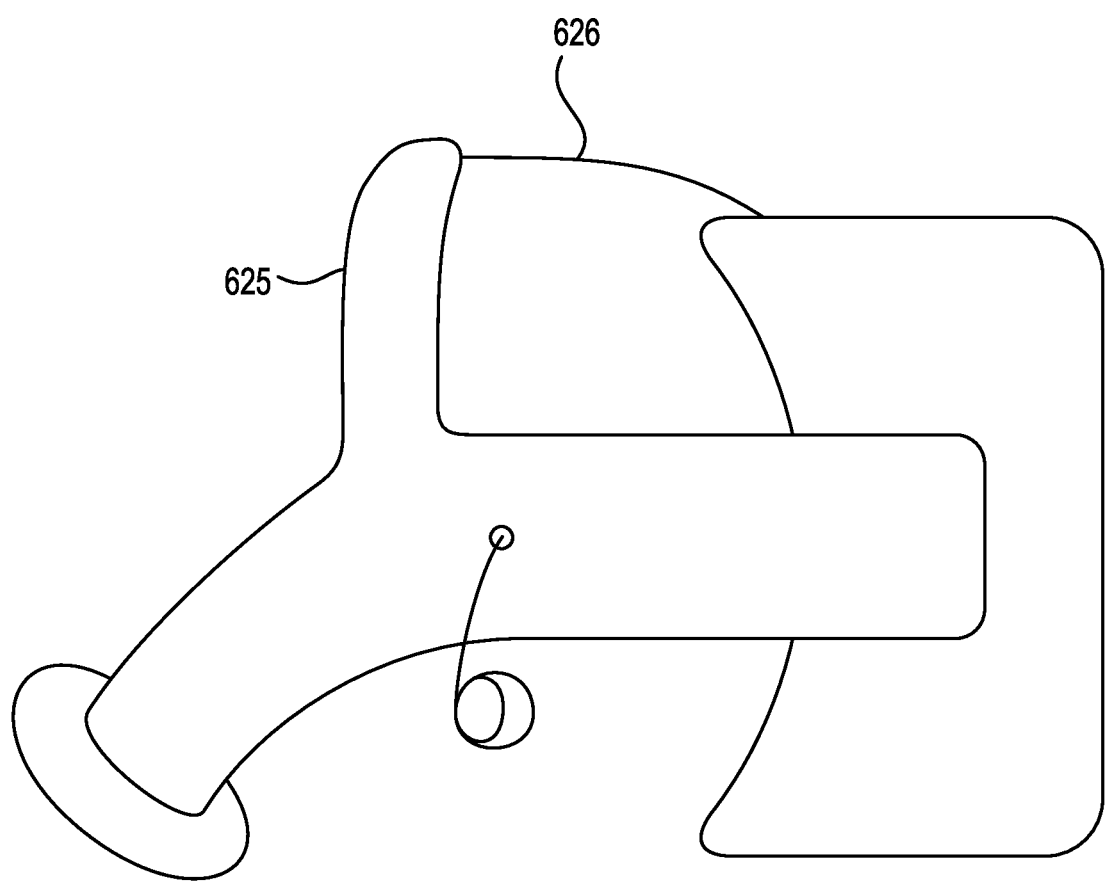
FIG. 32 illustrates a side view of a mobile content delivery headset that incorporates an over the head attachment to hold an eyepiece or viewing display in place.

FIG. 32 illustrates a mobile content delivery system that incorporates an over-the-head band 625, similar to over the head headphones. The benefit over other described embodiments is the ability to shorten the over-the-head eyepiece attachment 626 so it does not go all the way to the back of a user's head. This is especially beneficial for users with longer hair.

Figure 33:
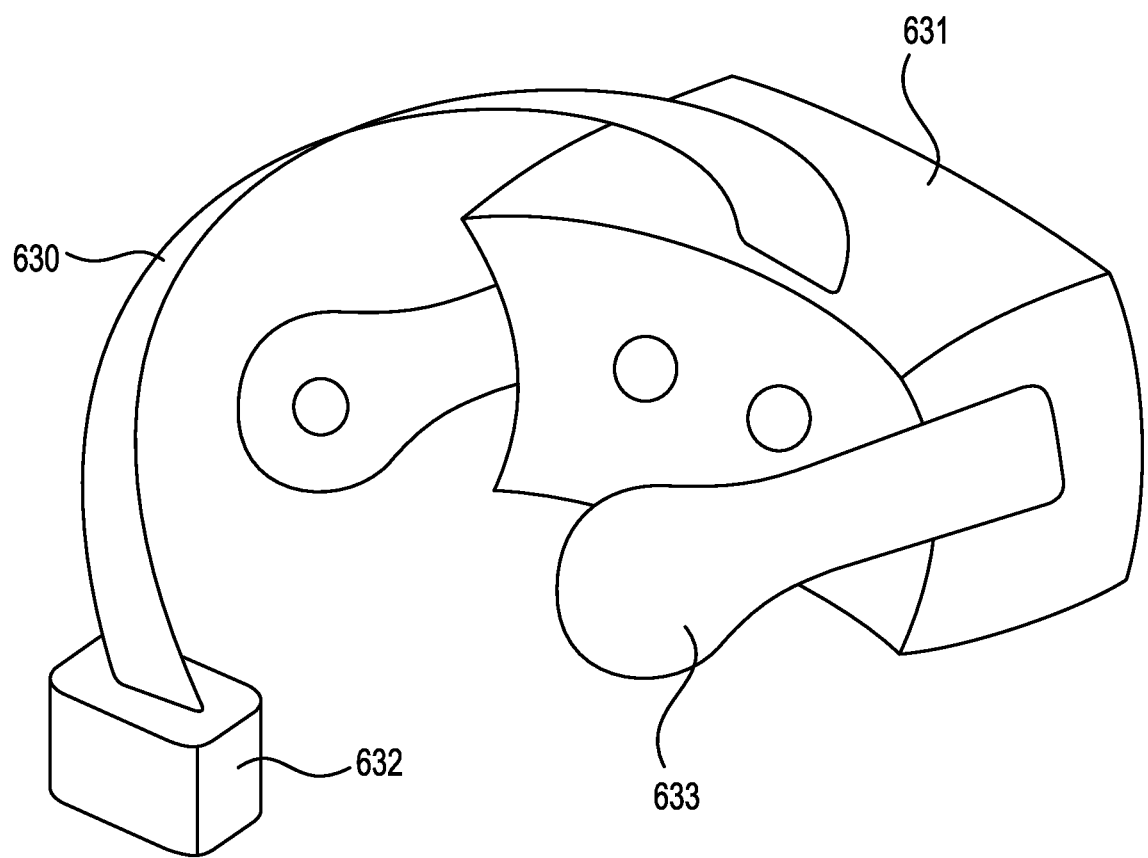
FIG. 33 illustrates a perspective view of a mobile content delivery headset with an over the top of the head design.

Referring now to FIG. 33, there is illustrated a mobile content delivery headset with an over-the-head attachment system 630 that holds an eyepiece 631 and tactile component 632 securely in place. Audio delivery arms 633 such as over, on or in-ear speakers are attached to and extend from the eyepiece.

Figure 34:
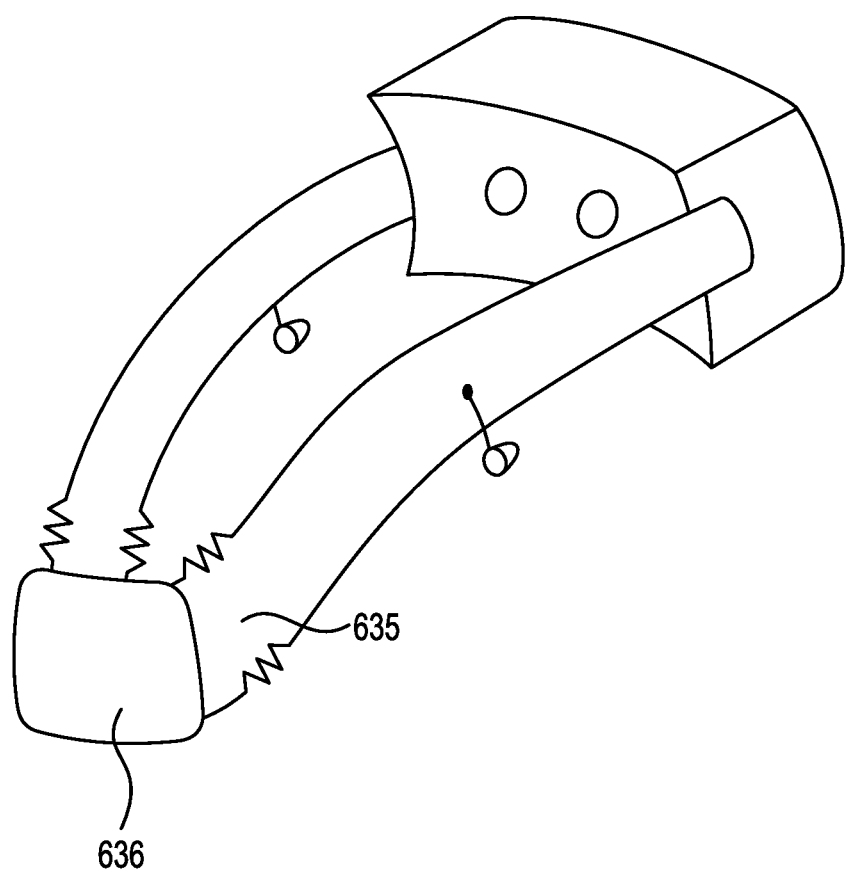
FIG. 34 illustrates a mobile content delivery headset with features that allow components to adjust, conform and move independent of each other.

FIG. 34 illustrates a mobile content delivery headset similar to other embodiments with the improvement being an adjustable feature 635 that allows components such as the tactile transducer 636 to move independently but fit snugly. Additional features include accordion or spring designs, stretchable materials such as elastic, sliding rails, and the like.

Figure 35:
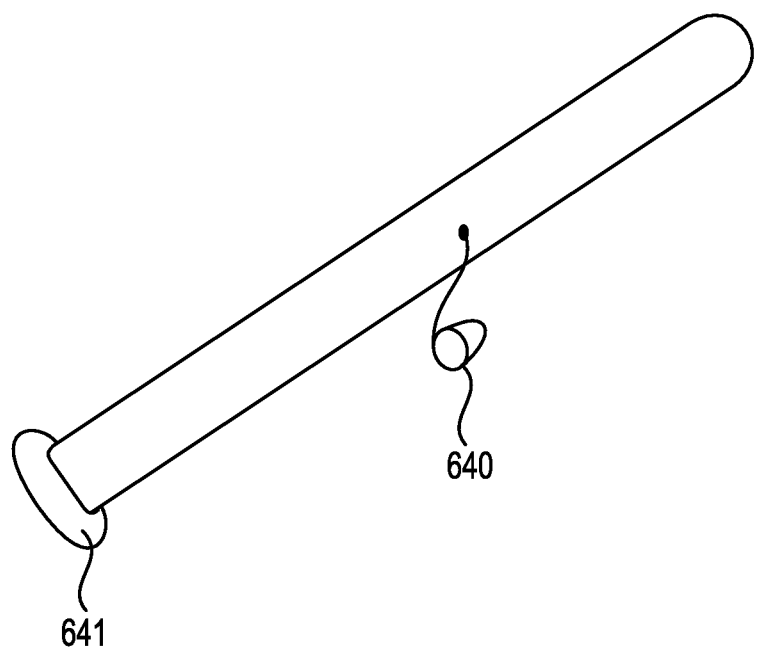
FIG. 35 illustrates a mobile content delivery headset, similar to FIG. 29, but without the eyepiece or viewing display.

Referring now to FIG. 35, there is illustrated a mobile content delivery headset, similar to FIG. 29, but without the eyepiece. The shape is similar to a headband or hairband and circumferential around the user's head to hold the audio delivery speakers 640 and tactile transducer 641 in place.

Figure 36:
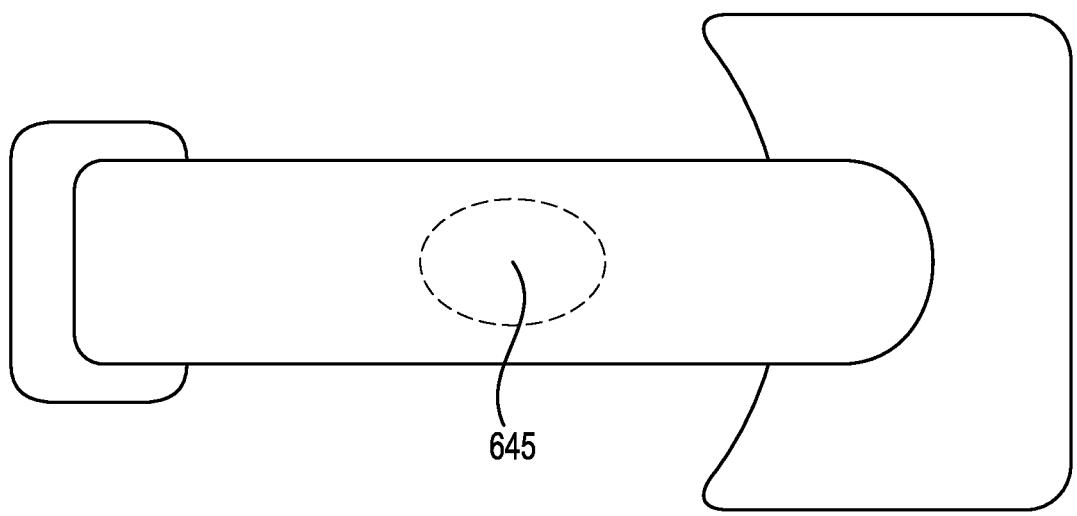
FIG. 36 illustrates a mobile content delivery headset with speakers directly over the ears.

FIG. 36 illustrates a mobile content delivery headset with speakers or similar transduction components placed inside the materials and worn directly over, on or near the user's ears 645. This feature is beneficial in that it simplifies the construction of the headset.

Referring now to FIGS. 37-54, the various embodiments described herein describe a wired or wireless headphone or headset system with various attachments and hooking configurations and methods. Construction materials are similar to other headphones or headsets, including plastic, metals, synthetics and softer materials such as mesh and foam. Attachment fixtures are shown herein on the rear and bottom of the headphone ear cup for attachment around the back of the neck, but it is envisioned the attachment mechanisms could be anywhere on the ear cup, such as on the front to attach glasses, virtual reality (VR) or augmented reality (AR) goggles, on the bottom to attach accessories, as well as on the headband for other types of attachments. Additionally, the headphone design described herein shows the attachment methods in one design, such as over the head, but it is envisioned that the methods and teachings could be incorporated into any type of headphone, headset or helmet design. Also, the attachment fixture molds are shown on the inside headphone mold, but it is envisioned that the fixtures could be secured on the outer ear cup or headband mold as well. Additionally, it is envisioned that the various attachment fixtures shown herein could be incorporated into the headphone mold, rather than a separate component, as well as part of an assembly that is wrapped around or affixed to the headphone mold. Also, the descriptions and images detail embodiments that attach to both left and right-side ear cups, but it is envisioned that accessories that attach to only one point of the headphone.

Figure 37:
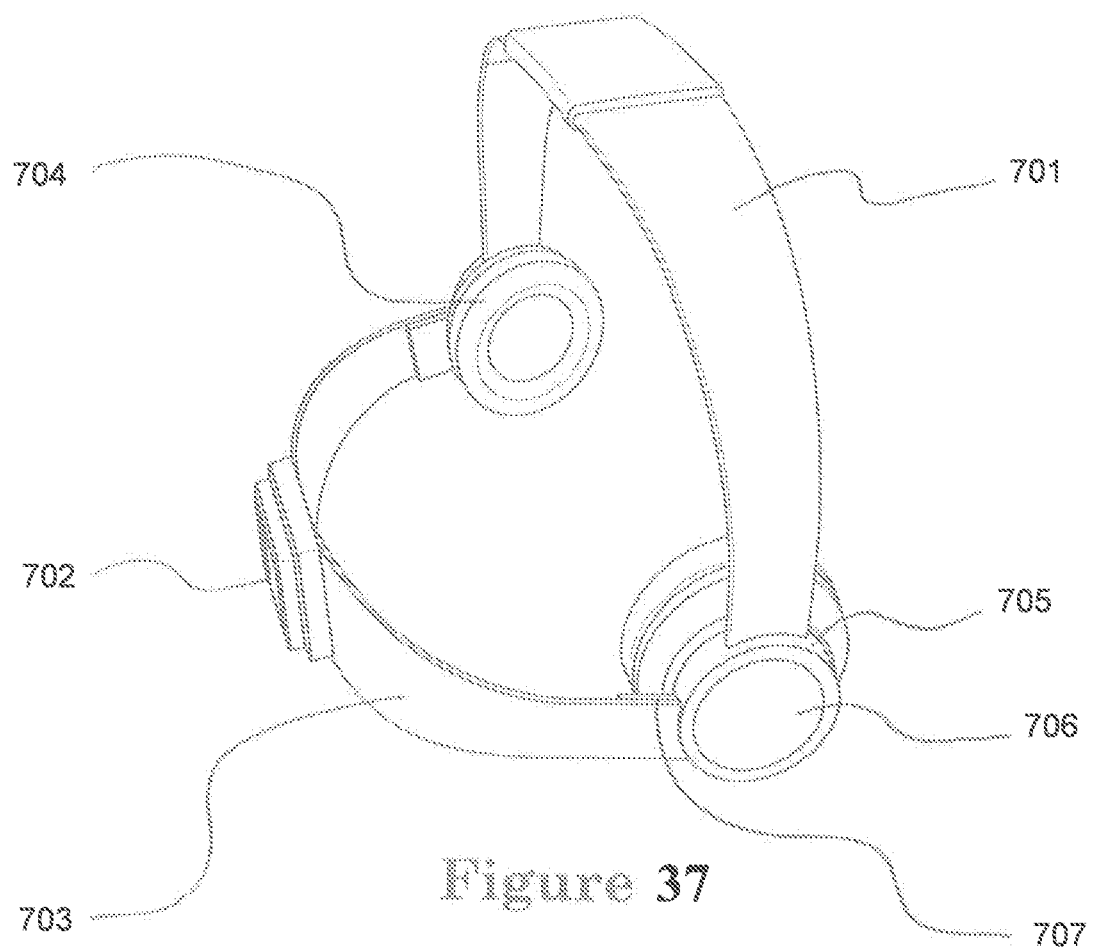
FIG. 37 illustrates a modular headphone system with an attachment to be disposed about a user's neck.

Now in more detail to FIG. 37 is described a headphone worn on or about the head with an attached component 702 held in place by attachment members 103. Similar to the other figures, the headphone type shown is over the head 701, but it is envisioned that other types of headphones could be used. The headphone has ear cups on each ear that comprise ear cushions 704, inner ear cup molds 705 and outer ear cup molds 706. The attached or attachable component can be various forms of stimulation such as visual or video, auditory, vibratory, electrical, thermal, olfactory or wind, as well as other types of accessories such as power, decorative, lighting or monitoring. The component can be held in place or worn in numerous places such as the back of the neck, on the head, and on the face.

The attachment members can be made from rigid, semi rigid, semi flexible or flexible materials. The attachment members connect to each headphone ear cup using various types of methods or fixtures 707. As shown, the attachment member connects to the back of each ear cup through a looping mechanism around a fixture in the headphone ear cup, which will be described below. The attachment members can connect directly to a component, can hold a component in a suspendable pouch-type method, and also hold a component in a particular position via rigid or bar-like methods.

Figure 38:
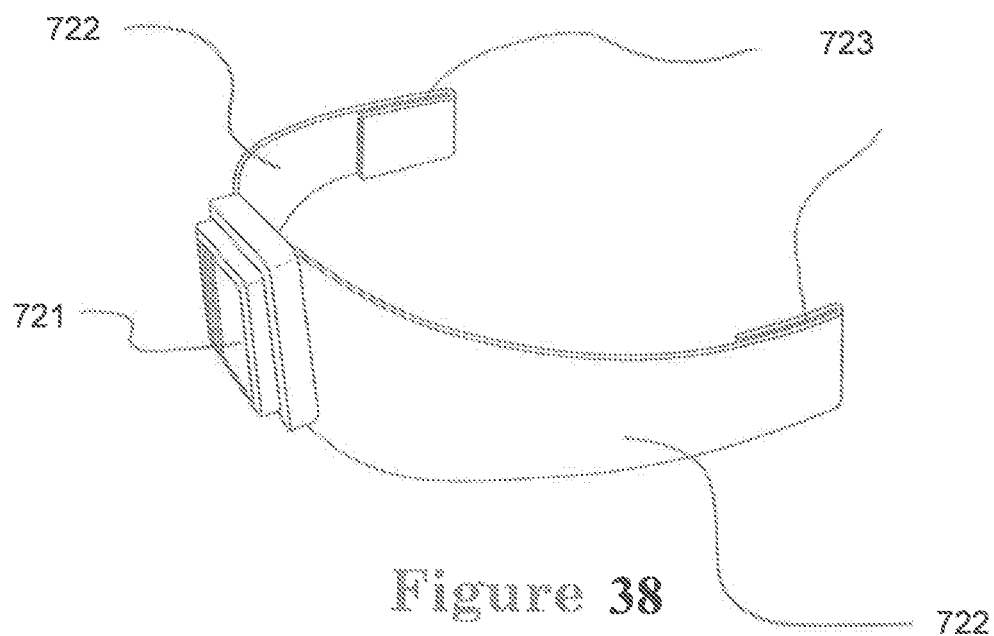
FIG. 38 illustrates a headphone attachment device for use with a headphone set.

Now in greater detail to FIG. 38 is described a representative component 721 with attachment members 722. The attachment members can be manufactured from a variety of soft and flexible materials, such as elastic or mesh, to allow the component to be worn comfortably in place, such as around the back of the neck or around the eyes. Additionally, the attachment members can be manufactured from more rigid materials such as plastic or metal, to hold the component securely in place. As an example, rigid mechanisms or arms could be inserted or attached to the front of the headphone and extended in front of the face or eyes of the user such as to attach a virtual or augmented reality eyepiece or projection device to it. The benefit of this approach is to create a modular headphone attachment system where the user can select from a variety of attachment members and attachable components to attach to their headphones. The attachment members can attach to the headphone ear cups on each end 723 by a variety of established methods such as Velcro®, latches, loops, pegs, rods, snaps, magnets, anchors, buckles or the like.

Figure 39:
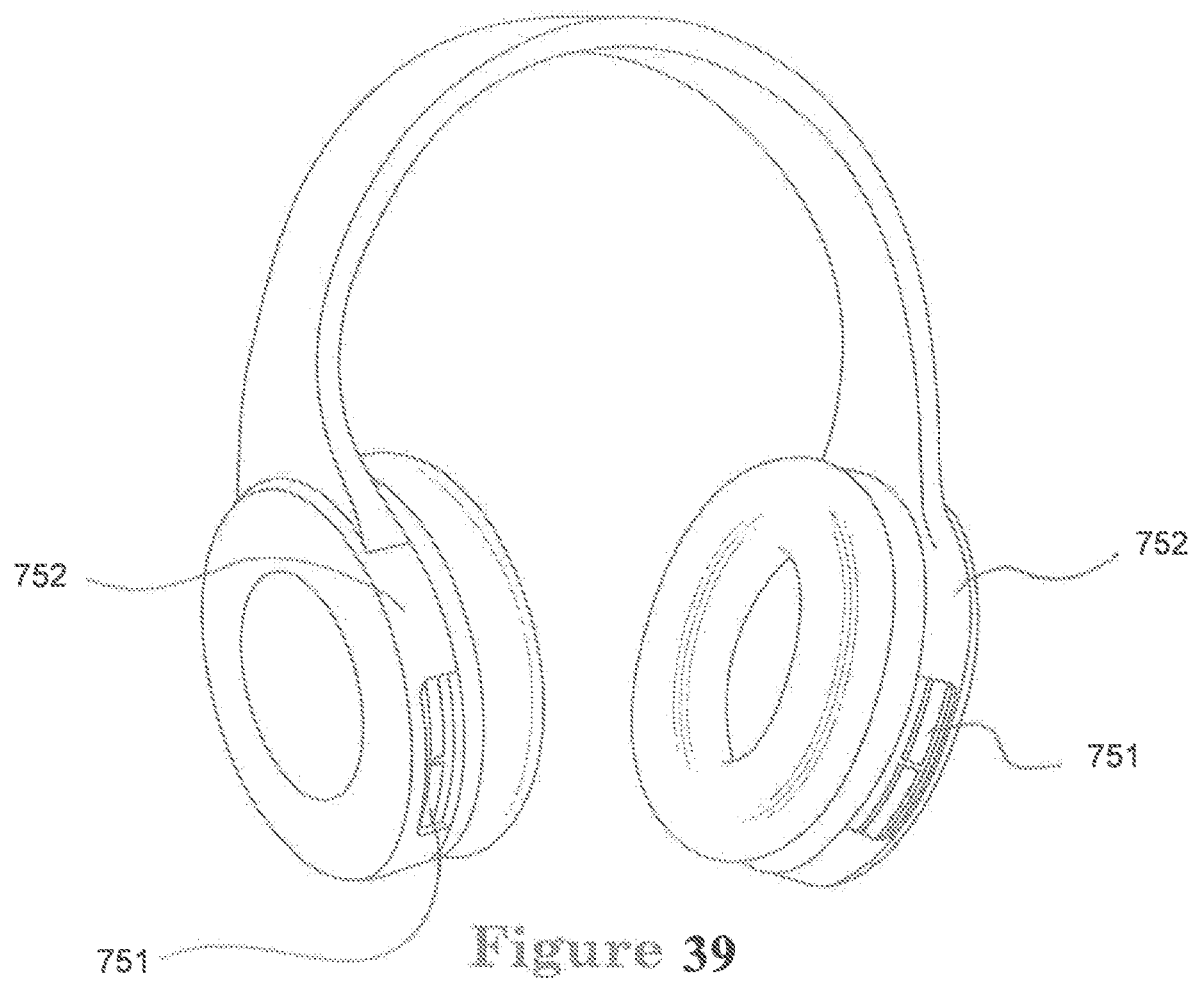
FIG. 39 illustrates a headphone with a set of attachment mechanisms or fixtures.

Now in greater detail to FIG. 39 is described a headphone with an incorporated component attachment system with attachment fixtures 751 in each ear cup mold. Here, the fixtures are shown as part of the inner headphone ear cup 752 but the fixtures or attachment configurations could be in other places on the headphone. The fixtures allow the user to attach various types of accessories, components or stimulation devices to the headphone system. Another benefit of such a design is the fixtures are recessed inside the mold, thus hiding the fixtures when not needed for component attachment. The fixtures are shown on the bottom of each ear cup so as to hold a component in place on the back of the neck, but it is envisioned they could be placed anywhere in or about the ear cup.

FIGS. 40 through 45 describe in greater detail different embodiments of a representative attachment system using modular fixtures that are a part of, in addition to, or attached to, headphones and headsets. While many types of fixtures are disclosed, it is envisioned other types, such as rod inserts, snaps and magnets, could be incorporated; therefore, the invention should also include these fixture or attachment methods. Construction materials of the attachment fixtures could include metal, plastic or similar hardened material that can support and hold the items attached to it.

Figure 40:
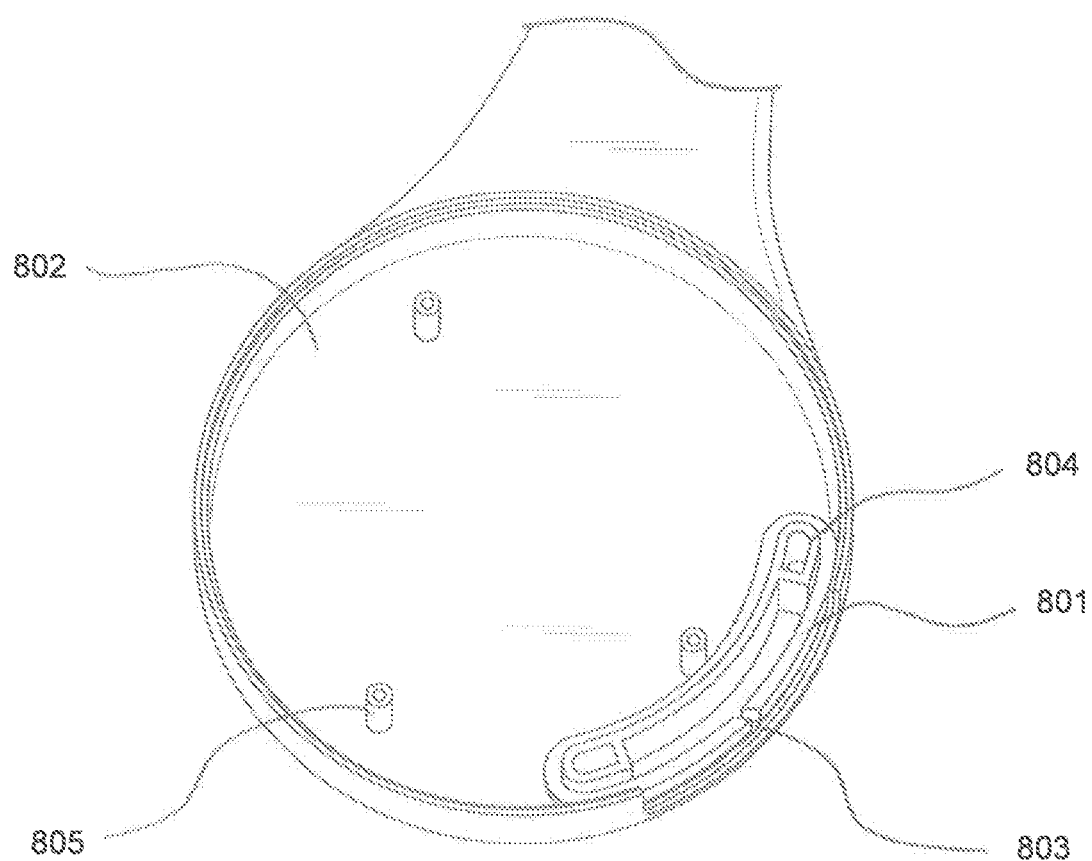
FIG. 40 illustrates a portion of a headphone attachment fixture with a slot in an ear cup.

FIG. 40 describes in greater detail one representative method for including an attachment fixture 801 in a headphone inner ear cup mold 802. The fixture shown has a slotted opening 803 to allow for easy attachment or removal of the attachment members, such as a loop of a stretchable band. The fixture can be molded in the ear cup, attached directly to the ear cup, and secured around predetermined molds in the ear cup 804. Construction materials of the attachment fixture can be strong and lightweight, such as plastic or metal. Screw holes 805 are shown that connect the inner and outer ear cup molds together.

Figure 41:
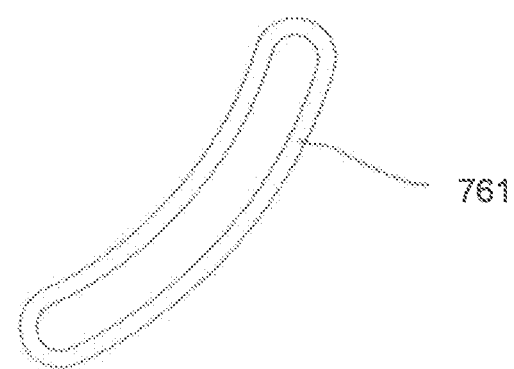
FIG. 41 illustrates a headphone attachment fixture for use in a headphone set that is in a closed configuration.

FIG. 41 describes an attachment fixture 761 by itself that is solid and has no slots. The attachment member can be looped through and passed around the fixture or can be connected via other methods such as Velcro, snaps or rings. The main benefit of this design is the secure attachment to the headphone.

Figure 42:
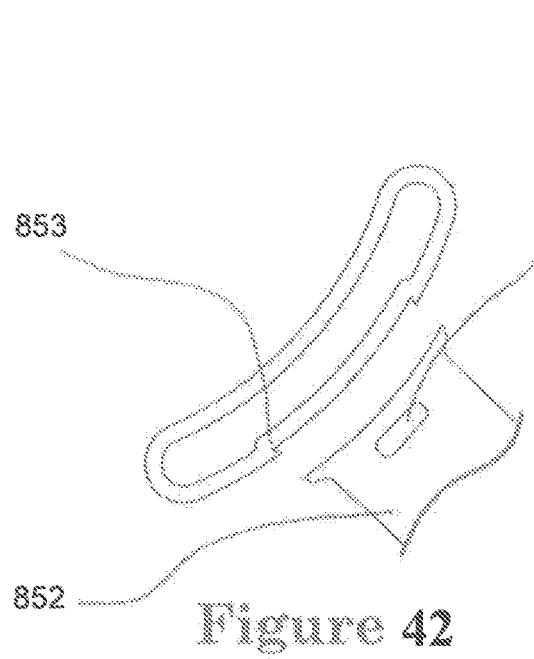
FIG. 42 illustrates a headphone attachment fixture or configuration for use in a headphone set with a depressible locking mechanism.

Now in greater detail to FIG. 42 is described an attachment fixture 853 to accommodate a depressible locking mechanism similar to those found on watchbands and other wearable products, as well as rigid members with depressible locking mechanisms that insert into receptor holes to lock the members into place. The user can depress a locking mechanism 851 on the end of the attachment member 852, to connect or disconnect it from the fixture. It is envisioned the locking mechanism can be on the headphone as well. It is also envisioned the mechanism could have a different shape but a similar functionality, such as a smaller fixture with a deeper mold to hold a rigid attachment rod, such as for virtual reality goggles, in place.

Figure 43:
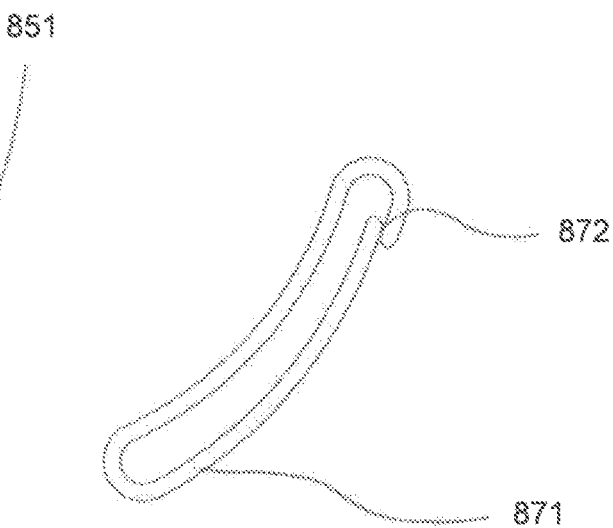
FIG. 43 illustrates a headphone attachment fixture for use in a headphone set with a hinged locking mechanism.
Figure 44:
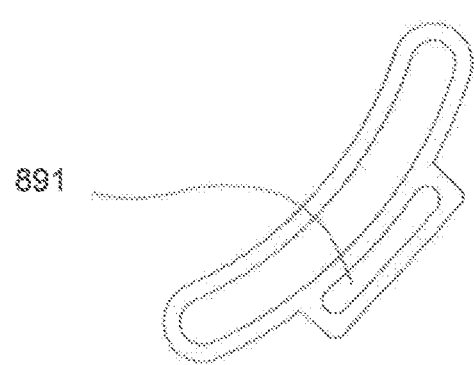
FIG. 44 illustrates a headphone attachment fixture for use in a headphone set with an extended closed loop.
Figure 45:
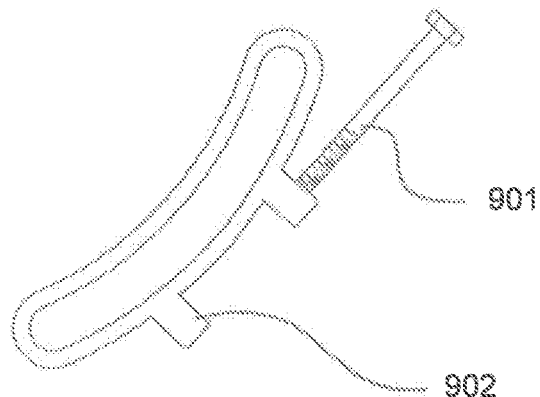
FIG. 45 illustrates a headphone attachment fixture for use in a headphone set with a screw locking mechanism.

FIG. 43 describes an attachment fixture with a hinge mechanism 871 and locking feature 872, similar to carabiner connectors that are used in camping. FIG. 44 describes an attachment fixture with a loop 891 that extends farther outside of the headphone ear cup mold than other described fixtures. The benefits of such a design are to allow for easier attachment to the headphone, as well as for larger or irregular shaped attachment members. In greater detail to FIG. 45 describes an attachment fixture with a removable screw or pin 901, similar to watchband or camping attachments, which can screw into the other side of the fixture 902 to secure the attachment member to the fixture.

Figure 46:
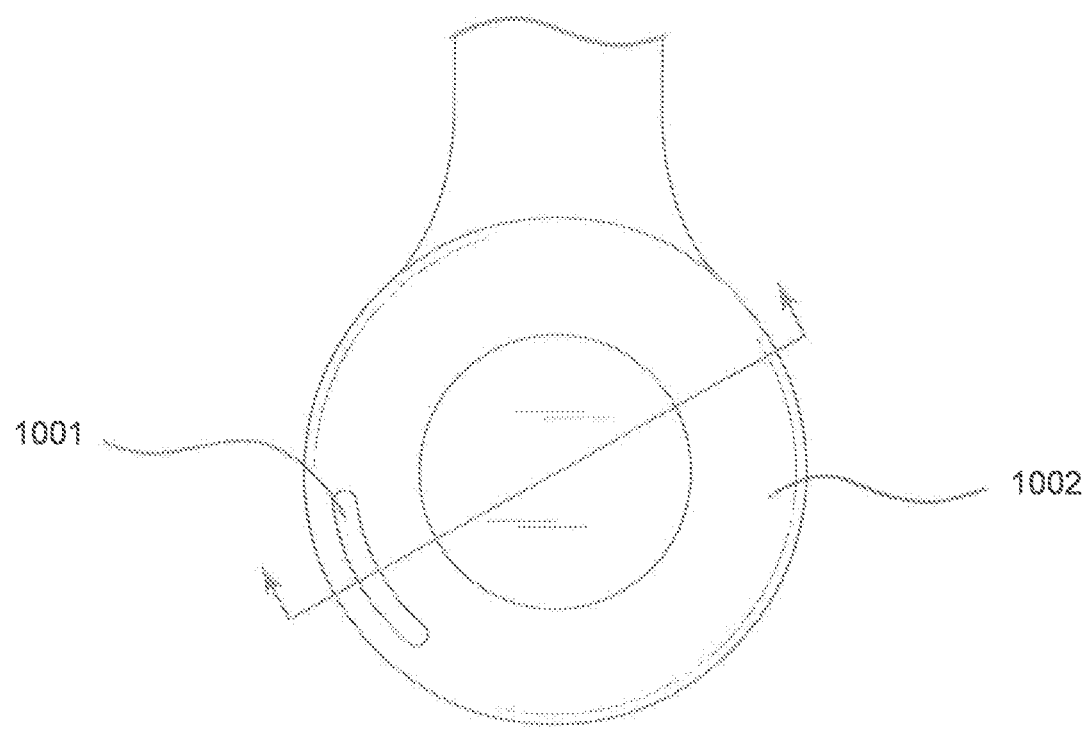
FIG. 46 illustrates an outside side view of an attachment slot located in a headphone ear cup.
Figure 47A:
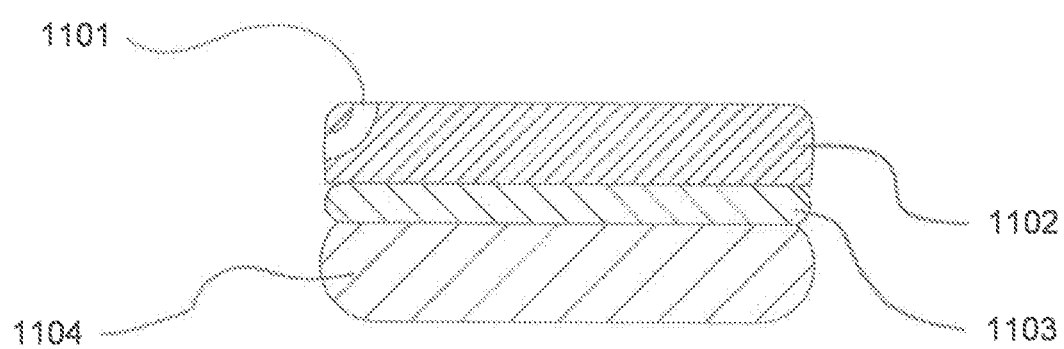
FIGS. 47A and 47B illustrate section side views of a headphone attachment mechanism located within a headphone set.
Figure 47B:
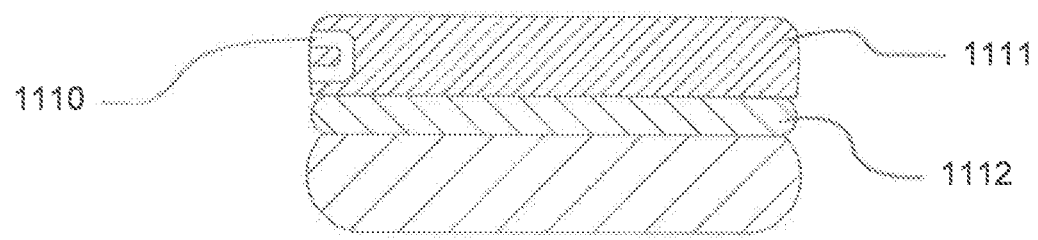

FIG. 46 describes how a slot or attachment fixture 1001 can be molded into or placed onto the headphone ear cup 1002 to allow various attachment members to connect to or pass through it. The benefit of this method is to eliminate the need for an additional or extra fixture piece like detailed above. Now in more detail to FIG. 47A is a section view of FIG. 46 showing how the slot or attachment fixture 1101 can be cut or molded where the attachment member can connect through the outer ear cup mold 1102. Section view of an inner ear cup mold 1103 and ear cushion 1104 are also shown, and it is envisioned that the attachment fixture mechanism can be included in these as well. Various forms of electronics and speaker components can reside in these ear cup molds. FIG. 47B shows in greater detail the section view of FIG. 46 where the slot or attachment fixture 1110 is cut or molded into the ear cup where the attachment member passes through an inner channel. This inner channel is shown in the outer ear cup mold 1111 but could be in the inner mold 1112.

Figure 48:
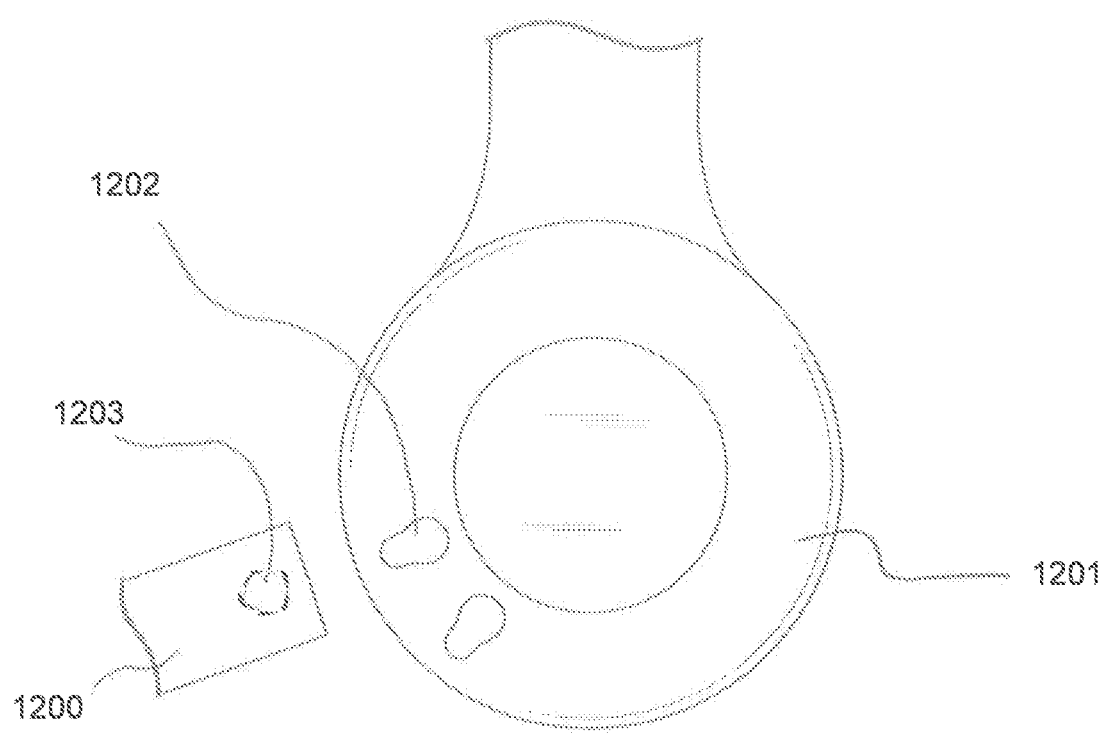
FIG. 48 illustrates a headphone attachment mechanism for use in a headphone set with slotted holes, magnets or apertures in the ear cup and a connection post or mechanism in an attachment band.
Figure 49:
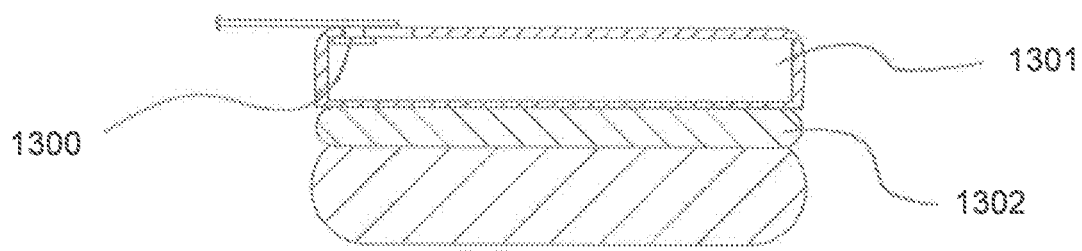
FIG. 49 illustrates a side section view of FIG. 48 with a male post inserted into slotted holes, magnets or apertures.

FIG. 48 describes in greater detail a different but similar method to connect an attachment member 1200 to a headphone or headphone ear cup 1201. Female holes, snaps, magnets or slots 1202 are molded or placed into the headphone ear cup and the opposite or male counterpart or post 1203 is placed on the end of the attachment member. The female slots are shown in one position on the headphone, but it is envisioned the slots could be placed anywhere on the headphone assembly. FIG. 49 describes in greater detail how the male post 1300 described in FIG. 12 is slid into, snapped, magnetized and connected to the female hole on the headphone, shown on the outer ear cup 1301 to secure the attachment member in place, but could be on the inner mold 1302 as well.

Figure 50:
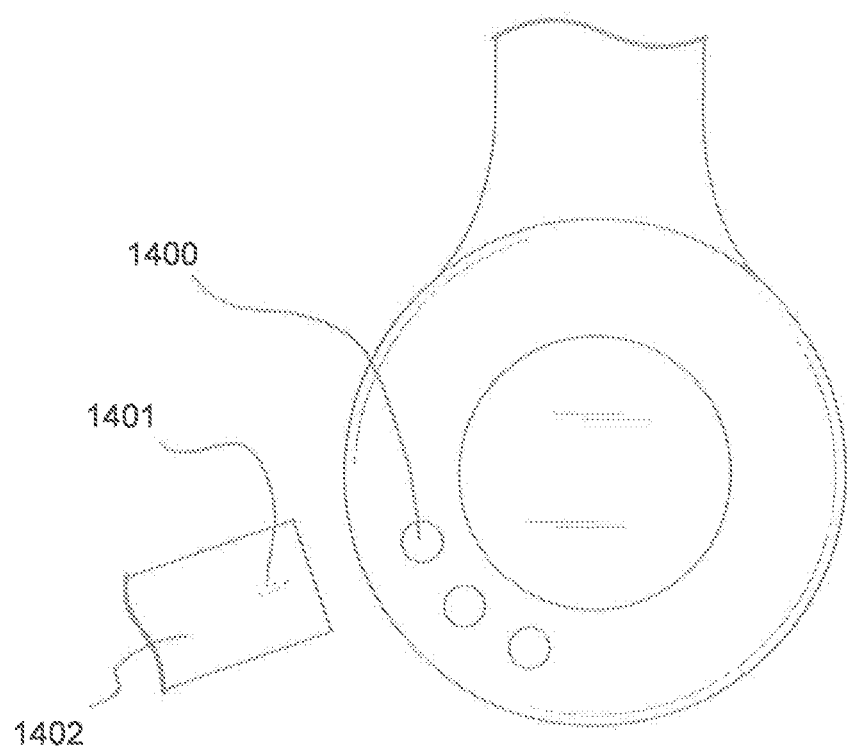
FIG. 50 illustrates a headphone attachment method with a plurality of male posts in an ear cup and female connection slots in an attachment band.
Figure 51:
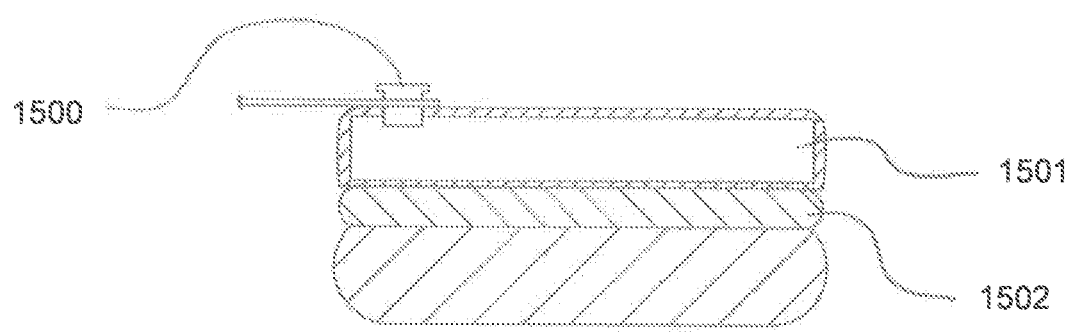
FIG. 51 illustrates a side section view of FIG. 50 with at least one female slot connected to at least one male post.

FIG. 50 describes a similar headphone attachment method to FIGS. 48 and 49. Here, the male posts 1400 are molded into the headphone ear cup mold and the female counterpart or slot 1401 is placed in the component attachment member 1402. FIG. 51 describes in greater detail how the female slot on the attachment member is secured to the male post 1500 on the headphone ear cup. The male posts are shown on the outside of the outer ear cup 1501 but it is envisioned they could be on the inner portion of the outer ear cup or in the inner cup 1502.

Figure 52:
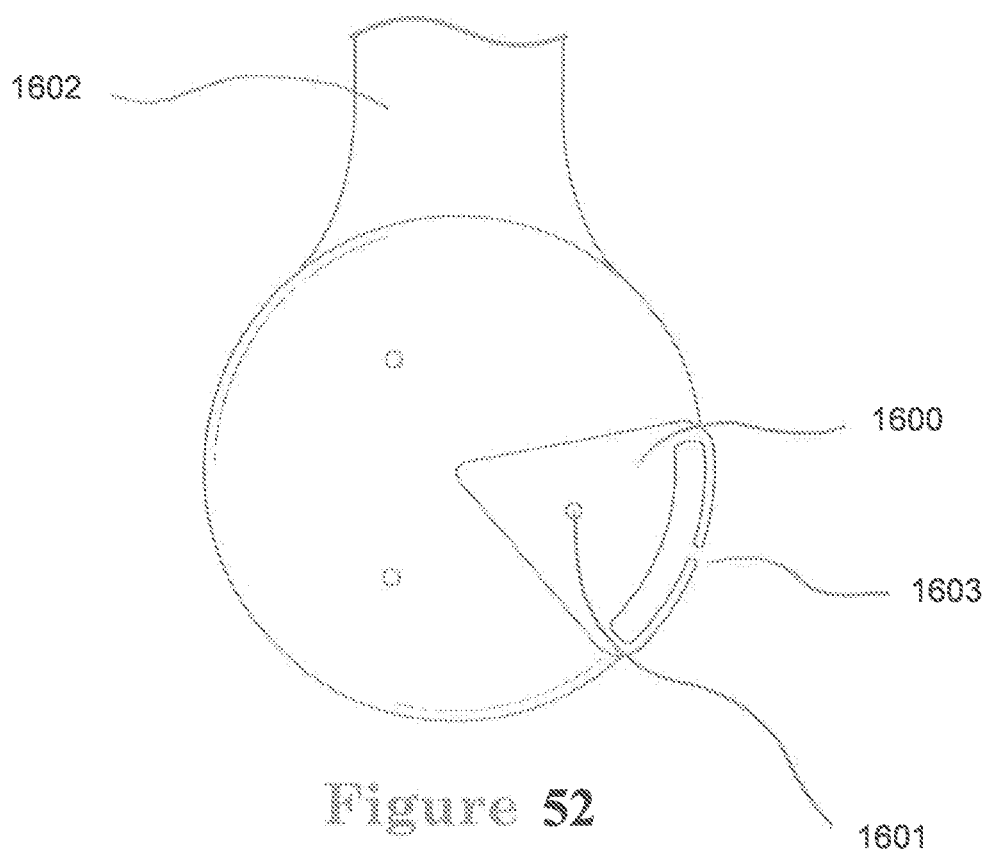
FIG. 52 illustrates a headphone attachment fixture disposed within an ear cup mold having a slotted opening.

Now in greater detail to FIG. 52, a headphone attachment method similar to FIG. 4 is shown. In this embodiment, rather than placing the fixture 1600 around the ear cup mold to secure in place, the fixture, here shown with a slot 1603 but could be shaped like other methods described herein, is larger and is attached directly to the ear cup via a screw 1601 or similar attachment method. Similar to other Figures, it is envisioned that the fixtures could be included in the outer or inner headphone ear cup, or in the headphone headband 1602.

Figure 53:
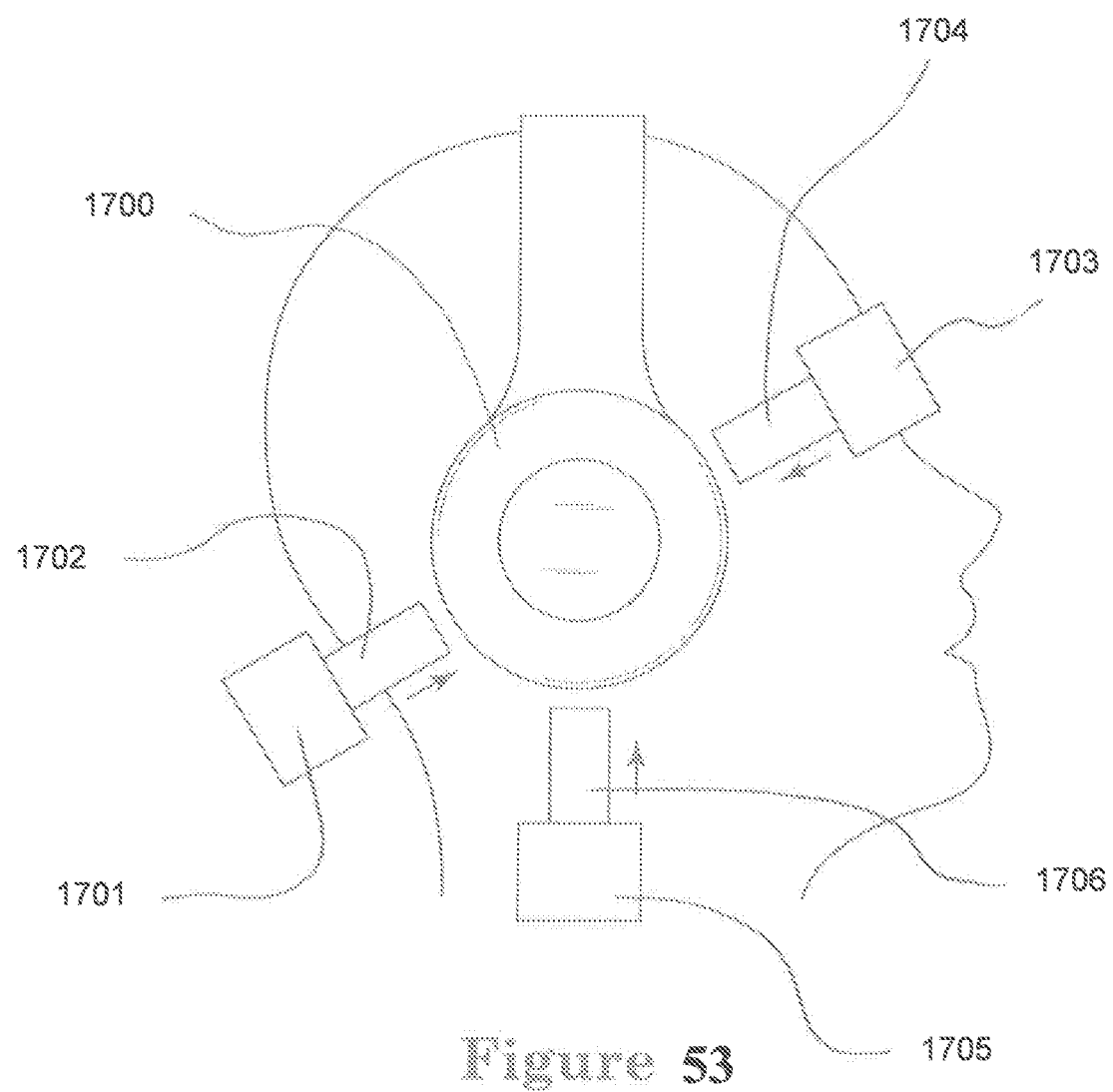
FIGS. 53 and 54 illustrate modular headphone systems, where

Now in greater detail to FIG. 53 is shown a representative view of a modular headphone attachment system with various components and attachment members connecting to headphones in various receptacle positions on and around the headphone ear cups through the fixtures described herein 1700. Neck-based components 1701 can be worn around the back of the head and neck with attachment members 1702. Such components could include but are not limited to stimulation or monitoring devices, and power or lighting accessories. As an example use, a mobile user can attach a device, with methods described similar to above, that contains and releases olfactory smells that correlate to content being played through their headphone, similar to rides at amusement parks such as "Soaring over California" at Disney®.

Face or forehead-worn components 1703 can be worn on or about the eyes, around the forehead or in front of the face with flexible or rigid attachment members 1704. Such components could include but are not limited to virtual or augmented reality glasses or video projection devices, lighting accessories, cameras, fans, eye covers, forehead monitoring or stimulation devices. One example use is a user wanting to join a virtual cycling training class can insert a video projection or augmented reality device into the front of our headphones to play content that displays in front of them similar to Peloton® but without the fixed screen. The benefit is that through augmented lenses, content can be projected in front of the user that mimics virtual riders passing in front of near them while riding. A rider can listen to an instructor through the headphone ear speakers and hear the cars going past them. Additionally, with a tactile unit on the neck, users can feel the virtual content in real time of going over bumps in the road or getting bumped by other riders.

While not shown here, it is also envisioned to provide a headphone system with channels in each ear cup facing to the front of the user's face that facilitate easy placement of reading glasses. The main benefit of this embodiment of the invention is to relieve the pressure that existing over or on ear headphone styles put on users who wear glasses with arms that rest between the top of the ear and the head. By placing a channel in the headphone or headphone ear cup so the user can insert the arms of their glasses inside them, the user can eliminate the squeeze and uncomfortable feeling caused by the pressure of traditional headphone ear cups on the arms around the ears.

Other components 1705 can connect to the bottom of the ear cups with various types of attachment members 1706. Such components could include but are not limited to decorative or lighting accessories, camera devices or power accessories. As an example, in surgery, a doctor in training could wear the headphones to receive audio instruction from another surgeon, attach a video recording accessory on one ear and a lighting accessory on the other to display the surgical procedure to the observing physician. The benefit is through a single head-worn system, content can be seen, recorded, shared and commented on with many participants at one time.

Figure 54:
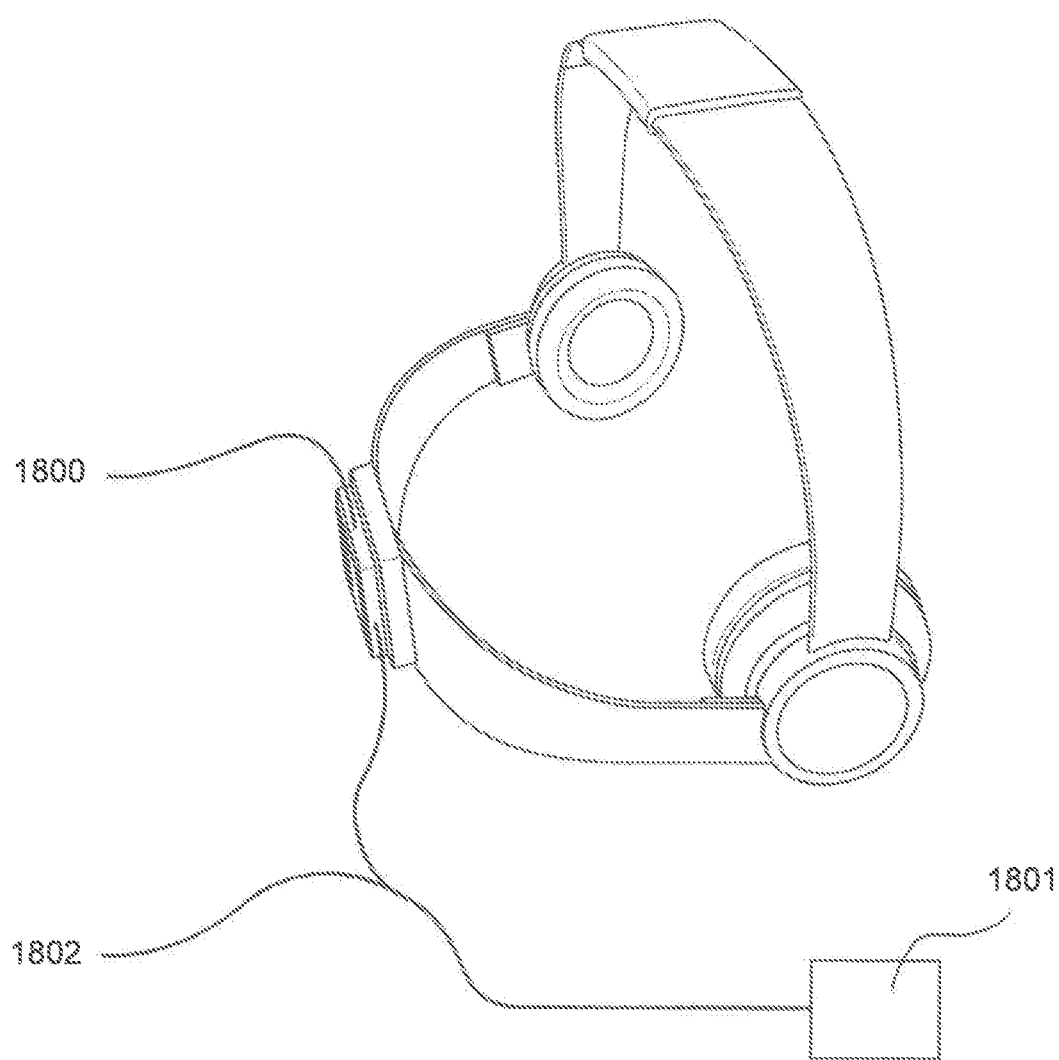

FIG. 54 describes a modular headphone attachment system with a component 1800 that is attached to headphones and connected to other external devices 1801 via wires or cables 1802, or wirelessly and remotely. While we describe an external device connecting to a component wrapped on the neck, it is envisioned the device could connect or interact with components attached to other areas of the headphone. These external devices could include but are not limited to power sources, computers, diagnostic machines, fitness or wellness equipment, rehabilitation equipment, training equipment, or other types of control units such as mobile devices.

One representative embodiment of a treatment application is a patient, such as a child, undergoing a surgical procedure and instead of using a sedative to relax them, placing a modular headphone system that is connected to an outside source of content. The patient can select the type of content they wish to use as a distraction, and the types of stimulative accessories, such as vibration, video, olfactory or thermal, to connect to the audio receptor in the headphones to help them relax. The benefit being is that the patient does not need to be administered drugs before, during or after the procedure.

Another example use of this embodiment is a remote medical provider can assess, diagnose and deliver various forms of wearable therapy to the user who is wearing the headphone with an attached diagnostic and therapeutic delivery component. This way, the patients can be in their homes or other location and can receive non-invasive therapies from doctors in remote locations. Another example of this embodiment is the user can receive instructional content from an outside source, which is delivered through the headphone system with an attached vibratory component on the neck and a virtual reality headset on the eyes, which simultaneously sends a wireless vibratory signal to a handheld golf or baseball swing trainer. The result is a multimodal training system that activates the brain and body in multiple ways at the same time.

Referring now to FIGS. 55-58, in a related embodiment, there is provided in-ear style transducers in which there is placed a vibration transducer, vibration speaker or similar transduction output method inside the housing of in-earphones or hearing aids that are worn in each ear canal, so when music, audio and other forms of digital content is played through them, they deliver low frequency tactile vibration output, in addition to audio output, to the user. Sound consists of vibration that can be heard and felt by the body. Current earphones and hearing aids have very small speakers that can only play music and sound that can be heard. However, if you strike a tuning fork and hold the fork end next to your ear, you can hear the audio vibration, and if you gently place the straight end into your ear canal, you can feel the tactile vibration. By adding vibration transducers, vibration speakers or similar transduction output devices into each earphone or hearing aid housing and placing the housing into the ears, the user will also be able to feel the tactile vibrations in the sound output. There are several advantages for the user: experience music like they are at a live event; they can experience movies like they are at a theater; they can feel like they are sitting in a vibration gaming chair wherever they are; if they have hearing loss in low frequencies, they can feel and hear the sound output as most hearing aids only deliver frequencies down to 125 Hz; they can use with vibration-based content as a bimodal (hear, feel) restorative wearable that activates the brain to help relax, improve balance and reduce pain; they can have balance activated through vibrational content that's delivered when the accelerometer in the earphones detects a fall;

they can have relaxing vibrational content delivered when the heart rate sensor detects stress; they can work with other software, such as live entertainment events, to deliver the feeling of bass; they can stimulate both the auditory and peripheral sensory systems at the same time to reduce pain and relieve anxiety; as well as many other uses.

Figure 55:
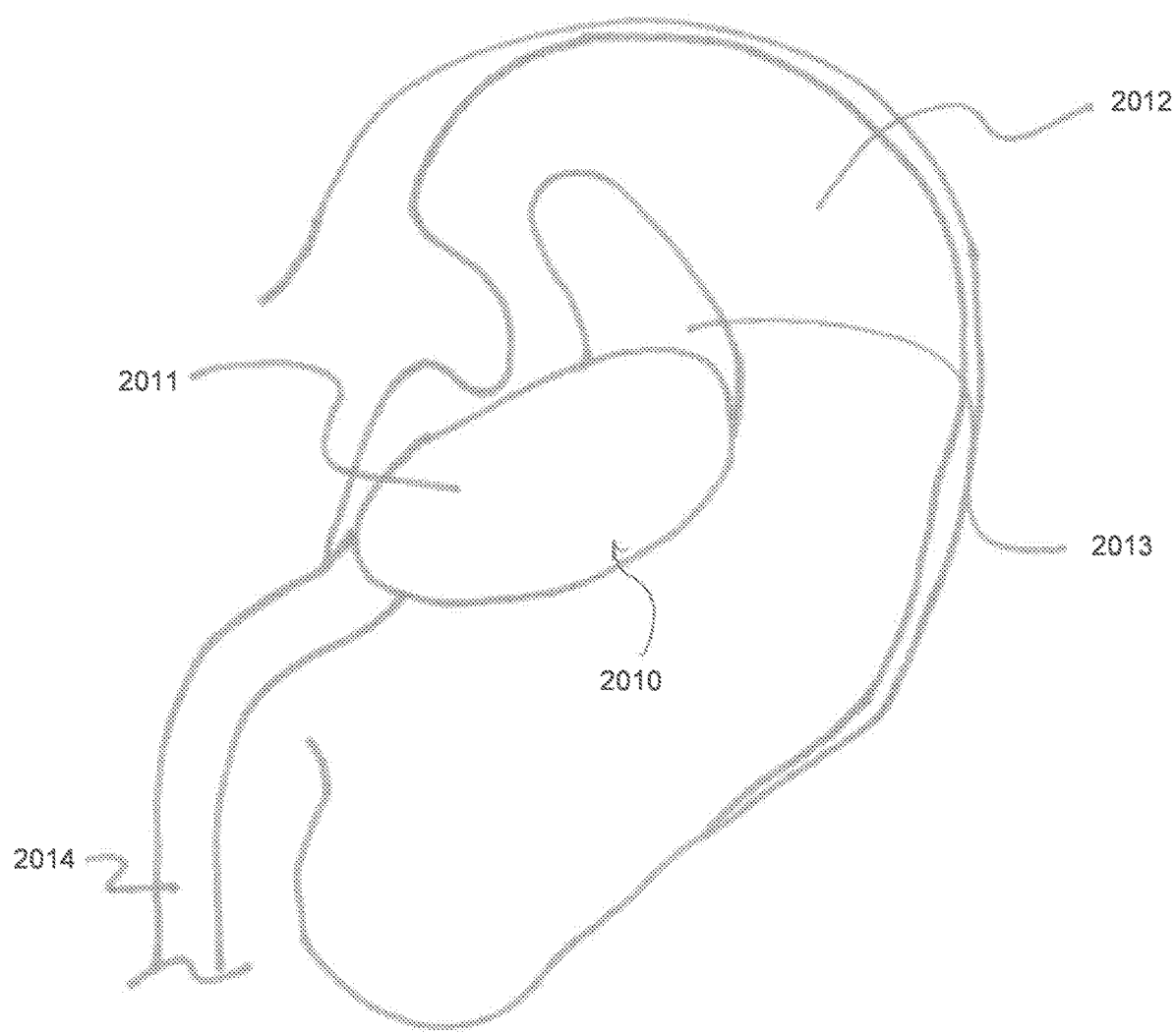
FIGS. 55-57 illustrate an in-ear wireless audio assembly according to the teachings herein using vibrational transduction technology to enhance hearing.

Specifically, FIG. 55 illustrates a side view of the left ear 2012 with an earphone device 2010 inserted inside the ear or ear canal 2013. The shape of the device 2010 is for illustrative purposes only and can resemble any shape of currently available earphones or hearing aids. In this example embodiment, an outer shell 2011 of earphone device 2010 includes control buttons or lights on the surface and includes electronics integrated inside. There could also include various methods to hold the earphone in place inside the ear 2013. The device 2010 could be connected via wires 2014 or alternatively via wireless connections (Bluetooth or RF).

Figure 56:
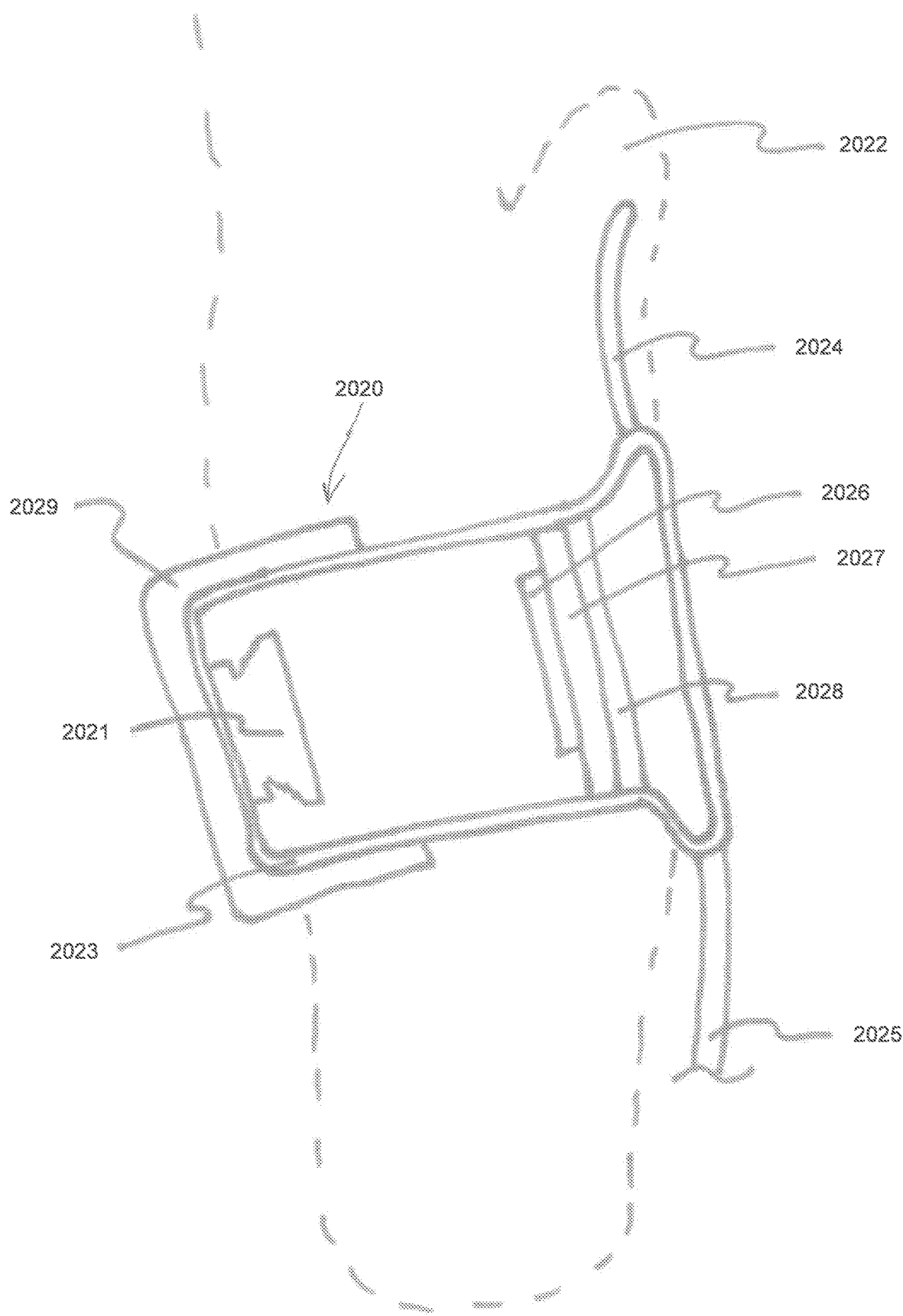

FIG. 56 illustrates a representative cut away view of earphone device 2020 located inside a user's ear/ear canal 2022. The vibration speaker, transducer or similar vibratory output method or device 2021 is attached directly to the outer shell or housing 2023 so that when sound is played and the transducer is activated, the outer shell 2023 transmits the vibration to the user so he/she can feel the vibrations inside the ear canal 2022. It is envisioned that the earphone device 2020 would have an outer layer 2029 made from a softer and more pliable material (such as silicone) to securely and comfortably hold it in place. Other components are included (not shown in detailed but housed by housing 2023) such as control board electronics 2028, battery 2027 and additional speakers 2026, in addition to heart rate assessments, accelerometers, and other diagnostic components, could also be included. In this example embodiment, earphone device 2020 is held in place with structures or elongate members extending from a base 2024 (or could be an over the ear attachment member) and can be connected to or driven by wires or cables 2025.

Figure 57:
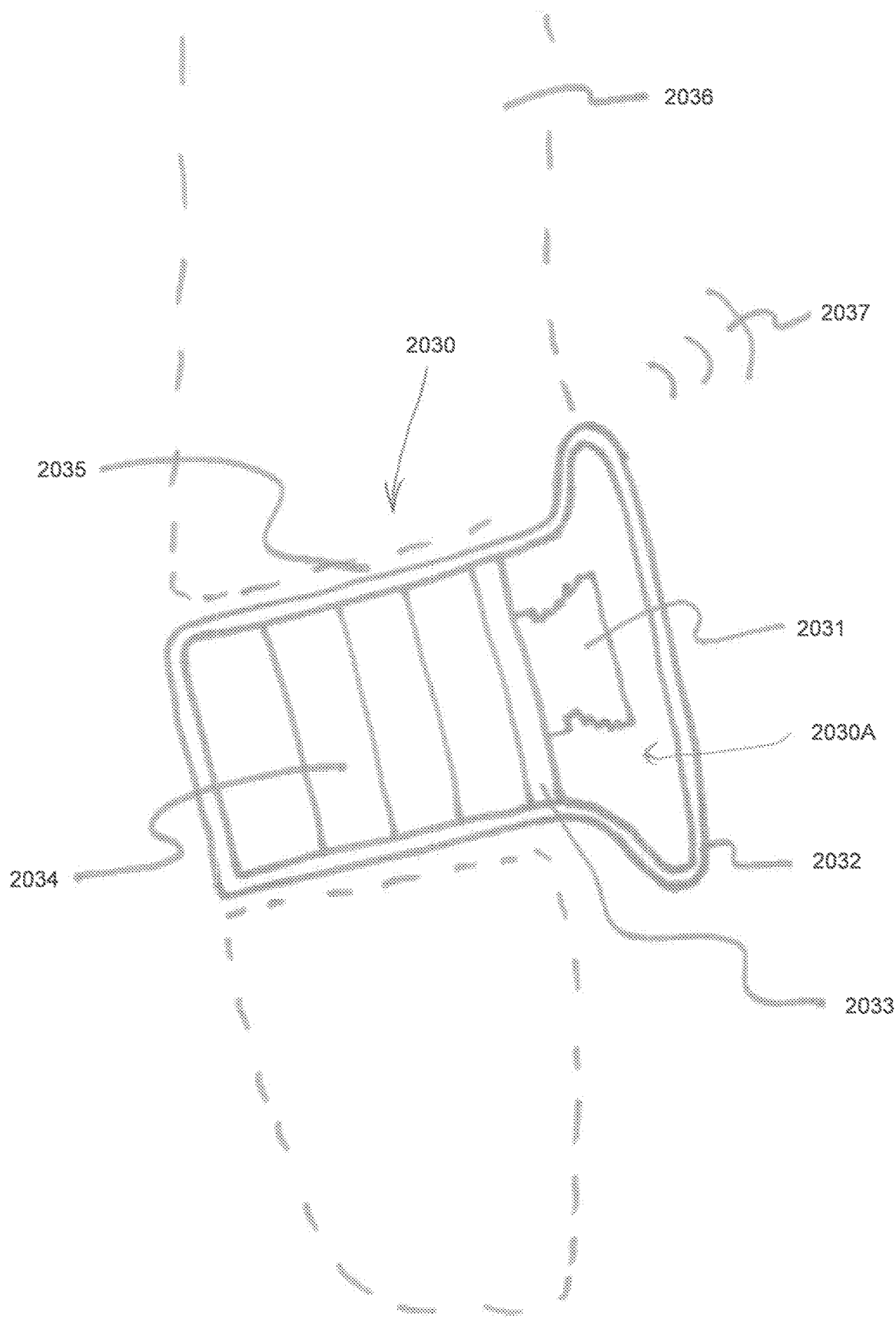

FIG. 57 illustrates a cut away view of a different earphone device 2030 embodiment where the vibration transducer 2031 is placed in an outer portion 2030A of device 2030 to allow for more room for transducer 2031. The transducer can still be secured directly to the outer housing 2032 through attachment to an internal section of the housing 2033. The other electronics and components (not shown in detailed), such as battery and speaker components 2034 can be placed in the end of the earphone device 2030, which is placed inside the ear canal 2035 of the ear 2036. It is also envisioned that the earphones can remotely or wirelessly communicate via RF or Bluetooth waves 2037 with other devices or software.

The following patents and publications are incorporated herein by reference in their entireties: U.S. Publication Nos. 2012/0253236 A1; US 2015/0038886; and US 2017/0135896; and International Publication No. WO 2013/122870 A1.

The foregoing specific embodiments of the present invention as set forth in the specification herein are for illustrative purposes only. Various deviations and modifications may be made within the spirit and scope of the invention without departing from the main theme thereof.

What is claimed is:

1. A wearable audio and vibrational delivery output apparatus comprising:
   (a) a headphone set adapted to be placed about a head and ears of a user including ear cups configured to be placed about the ears;
   (b) a housing comprising at least one vibration speaker or vibration transduction component, the at least one vibration speaker or vibration transduction component adapted to be positioned on a back of the user's neck and on an upper spine of the user;
   (c) right and left attachment members each comprising a proximal portion directly or indirectly connected to the housing, and a distal portion adapted to be attached to a fixture on an outer surface of each of the ear cups of the headphone set, wherein the attachment members comprise a non-rigid material adapted to provide better isolation of low frequency vibrations from the at least one vibration speaker or vibration transduction component to the ears of the user; and
   (d) at least one of an augmented reality (AR) accessory, a virtual reality (VR) accessory and a mixed reality (MR) accessory attachable to the outer surface of each of the ear cups, wherein each of the AR, VR and MR accessories are adapted to provide at least video or visual images to the user.

2. The apparatus of claim 1 wherein each of the right and left attachment members are adapted to be permanently affixed to the respective ear cups.

3. The apparatus of claim 1 wherein each of the respective ear cups is adapted to be releasably coupled to each of the right and left attachment members via the fixture on the outer surface of each of the ear cups.

4. The apparatus of claim 3 wherein each of the ear cups is adapted to be disassembled for releasing and re-engaging each of the attachment members.

5. The apparatus of claim 2 wherein each of the attachment members include at least one cord loop and a tensioning member adapted to adjust tensioning of the housing against the user's neck, wherein the tensioning member includes at least one dial or attachment disc adapted to turn clockwise or counterclockwise to cause shortening or lengthening of the at least one cord loop.

6. The apparatus of claim 1 wherein the virtual reality accessory includes a VR headset.

7. The apparatus of claim 1 wherein the virtual reality accessory is selected from a group consisting of VR goggles, a VR helmet, a display screen, a lens and lenses.

8. The apparatus of claim 1 wherein the augmented reality accessory includes AR wearable glasses or goggles.

9. The apparatus of claim 1 wherein the augmented reality accessory is selected from a group consisting of an AR eye piece, a AR video projection device, an AR lens or lenses, a helmet and an AR olfactory device.

10. The apparatus of claim 1 wherein the ear cups and the at least one vibration speaker or vibration transduction component are each adapted to receive a wired or wireless signal from an audio output device, wherein the ear cups provide audio sensory stimulation and the at least one vibration speaker or vibration transduction component provides tactile vibrational stimulation.

11. The apparatus of claim 1 wherein the ear cups and the at least one vibration speaker or vibration transduction component are each adapted to receive a wired or wireless signal from a signal output device adapted to provide multiple signals, wherein the ear cups provide audio sensory stimulation and the at least one vibration speaker or vibration transduction component provides tactile vibrational stimulation while the AR accessory is activated.

12. The apparatus of claim 1 wherein the ear cups and the at least one vibration speaker or vibration transduction component are each adapted to receive a wired or wireless signal from a signal output device adapted to provide multiple signals, wherein the ear cups provide audio sensory stimulation and the at least one vibration speaker or vibration transduction component provides tactile vibrational stimulation while the VR accessory is activated.

* * * * *